(12) United States Patent
Furuya et al.

(10) Patent No.: US 8,404,861 B2
(45) Date of Patent: Mar. 26, 2013

(54) SUBSTITUTED PYRAZOLECARBOXYLIC ACID ANILIDE DERIVATIVE OR SALT THEREOF, INTERMEDIATE THEREOF, AGENT FOR AGRICULTURAL AND HORTICULTURAL USE, AND USE THEREOF

(75) Inventors: Takashi Furuya, Kawachinagano (JP); Hideo Kanno, Kawachinagano (JP); Kozo Machiya, Machida (JP); Akiyuki Suwa, Kawachinagano (JP); Noriaki Yasokawa, Kawachinagano (JP); Shinsuke Fujioka, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 588 days.

(21) Appl. No.: 11/990,282

(22) PCT Filed: Aug. 11, 2006

(86) PCT No.: PCT/JP2006/316198
§ 371 (c)(1),
(2), (4) Date: Mar. 14, 2008

(87) PCT Pub. No.: WO2007/020986
PCT Pub. Date: Feb. 22, 2007

(65) Prior Publication Data
US 2009/0105325 A1 Apr. 23, 2009

(30) Foreign Application Priority Data

Aug. 12, 2005 (JP) .................................. 2005-234405
Nov. 7, 2005 (JP) .................................. 2005-322531
Apr. 18, 2006 (JP) .................................. 2006-114937

(51) Int. Cl.
*C07D 231/14* (2006.01)
(52) U.S. Cl. .................................. 548/374.1
(58) Field of Classification Search .................. 514/406; 548/374.1
See application file for complete search history.

(56) References Cited

U.S. PATENT DOCUMENTS

| | | | |
|---|---|---|---|
| 6,316,503 B1 | 11/2001 | Li et al. | |
| 7,459,477 B2 * | 12/2008 | Furuya et al. | 514/406 |
| 2002/0198399 A1 | 12/2002 | Onishi et al. | |
| 2003/0187233 A1 | 10/2003 | Onishi et al. | |
| 2003/0204104 A1 | 10/2003 | Onishi et al. | |
| 2003/0236412 A1 | 12/2003 | Martins et al. | |
| 2004/0116744 A1 | 6/2004 | Furuya et al. | |
| 2005/0113567 A1 | 5/2005 | Onishi et al. | |
| 2007/0027154 A1 | 2/2007 | Yoshida et al. | |
| 2008/0064708 A1 | 3/2008 | Furuya et al. | |

FOREIGN PATENT DOCUMENTS

| | | |
|---|---|---|
| CL | 2042 2005 | 8/2005 |
| JP | 2001-122836 | 5/2001 |
| JP | 2002-539155 | 11/2002 |
| JP | 2003-48878 | 2/2003 |
| JP | 2003048878 A * | 2/2003 |
| JP | 2003-518110 | 6/2003 |
| JP | 2004-189738 | 7/2004 |
| JP | 2004-269515 | 9/2004 |
| JP | 2006-290883 | 10/2006 |
| WO | 01/56962 | 8/2001 |
| WO | WO 02096882 A1 * | 12/2002 |
| WO | 2005/021488 | 3/2005 |
| WO | 2005/115994 | 12/2005 |
| WO | 2006/015866 | 2/2006 |

OTHER PUBLICATIONS

International Search Report issued Nov. 14, 2006 in the International (PCT) Application PCT/JP2006/316198 of which the present application is the U.S. National Stage.

* cited by examiner

*Primary Examiner* — Joseph Kosack
*Assistant Examiner* — Matthew Coughlin
(74) *Attorney, Agent, or Firm* — Wenderoth, Lind & Ponack, L.L.P.

(57) ABSTRACT

The substituted pyrazolecarboxanilide derivatives represented by of the formula (I)

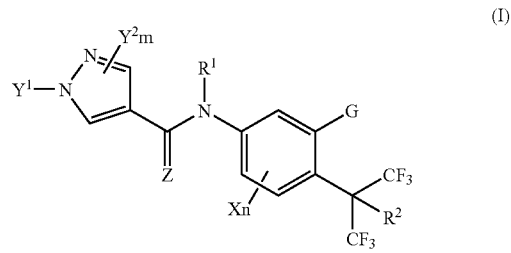

wherein $R^1$ is H, alkyl, alkylcarbonyl, alkenylcarbonyl, cycloalkyl, phenylalkyl, phenylcarbonyl and the like; $R^2$ is H, halogen, alkyl, CN, OH, alkoxy, phenoxy, phenylthio, phenylsulfonyl and the like; G is alkyl, alkenyl, alkynyl, cycloalkyl, $C_3$-$C_{10}$ cycloalkenyl and the like; Z is O or S; X is H, halogen, CN, $NO_2$, alkyl and the like; $Y^1$ is H, alkyl, alkenyl, phenyl, alkoxyalkyl and the like; $Y^2$ is H, halogen, CN, $NO_2$, OH, mercapto, amino, carboxyl, $C_1$-$C_6$ alkyl, phenyl, phenoxy, heterocycle and the like, m is 1 or 2; and n is 1-3, and salts thereof exhibit a superior effect as agrohorticultural insecticides or acaricides.

10 Claims, No Drawings

SUBSTITUTED PYRAZOLECARBOXYLIC ACID ANILIDE DERIVATIVE OR SALT THEREOF, INTERMEDIATE THEREOF, AGENT FOR AGRICULTURAL AND HORTICULTURAL USE, AND USE THEREOF

TECHNICAL FIELD

The present invention relates to substituted pyrazolecarboxanilide derivatives or salts thereof, intermediates thereof, and agrohorticultural agents, particularly insecticides or acaricides, containing said compounds as an active ingredient and method for use thereof.

BACKGROUND ART

Conventionally, substituted pyrazolecarboxamide derivatives similar to the present invention are known to be useful as agrohorticultural insecticides, fungicides or acaricides (e.g., JP-A-2003-48878, JP-A-2004-189738 and JP-A-2004-269515). In JP-A-2003-48878, the substituted pyrazolecarboxanilide derivatives are disclosed. However, the substituents in the aniline moiety are mostly limited to the 2-position substituents, the 3-position substituent is methyl group alone, and the compound described in the present invention, wherein alkyl group having 2 or more carbon atoms is introduced into the 3-position is not included even in its compound list. Moreover, the 3-position methyl form concretely disclosed therein does not show an acaricide activity. In JP-A-2004-189738, substituted pyrazolecarboxanilide derivatives are disclosed. However, the substituents in the aniline moiety are limited to alkoxy group, alkylthio group and alkylamino group, and the compound described in the present invention, wherein alkyl group having 2 or more carbon atoms is directly introduced into the 3-position is not included even in its compound list. In JP-A-2004-269515, substituted pyrazolecarboxamide derivatives are disclosed. However, only an amide compound with heterocyclyl amine is disclosed, and the substituted pyrazolecarboxanilide derivatives of the present invention are not disclosed.

DISCLOSURE OF THE INVENTION

In crop manufacturing in agricultural and horticultural fields, damages caused by insect pests are still serious, and development of novel agrohorticultural agents, particularly development of insecticides and acaricides is desired due to generation of insect pests resistant to known agents, and the like. Since various labor saving farm works are required due to increasing numbers of the aged farm working population, creation of agrohorticultural agents with properties suitable for such labor saving farm works, particularly insecticides and acaricides, is also demanded.

The present inventors have continued extensive studies on development of novel agrohorticultural agents, particularly insecticides and acaricides and have found, as the result, that among broad range of compounds described in the aforementioned prior document, a substituted pyrazolecarboxanilide derivative represented by the formula (I), in which a pyrazole ring is selected as the heterocyclic carboxylic acid moiety and a specific substituent is introduced into the aniline moiety at 3-position, showed excellent control effect as acaricides, not predicted at all from the content described in the aforementioned prior art references. Further, the inventors have found that an intermediate of said compound, i.e. a substituted aniline derivatives represented by the formula (II), and 1,3-dimethyl-5-trifluoromethylpyrazole-4-carboxylic acid or salt thereof were novel compounds unknown in prior references, and were useful as intermediates for manufacturing various derivatives having physiological activities such as pharmaceuticals, pesticides and the like, and thus completed the present invention.

Accordingly, the present invention relates to substituted pyrazolecarboxanilide derivatives represented by the formula (I):

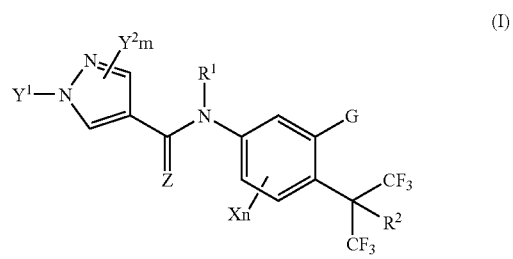

wherein
$R^1$ is 1a) a hydrogen atom, 2a) a $C_1$-$C_8$ alkyl group, 3a) a halo $C_1$-$C_6$ alkyl group, 4a) a $C_1$-$C_6$ alkylcarbonyl group, 5a) a halo $C_1$-$C_6$ alkylcarbonyl group, 6a) a $C_2$-$C_6$ alkenylcarbonyl group, 7a) a halo $C_2$-$C_6$ alkenylcarbonyl group, 8a) a $C_1$-$C_6$ alkylcarbonyl $C_1$-$C_6$ alkyl group, 9a) a $C_3$-$C_6$ cycloalkyl group, 10a) a halo $C_3$-$C_6$ cycloalkyl group, 11a) a $C_3$-$C_6$ cycloalkyl $C_1$-$C_6$ alkyl group, 12a) a halo $C_3$-$C_6$ cycloalkyl $C_1$-$C_6$ alkyl group, 13a) a $C_2$-$C_6$ alkenyl group, 14a) a halo $C_2$-$C_6$ alkenyl group, 15a) a $C_2$-$C_6$ alkynyl group, 16a) a halo $C_2$-$C_6$ alkynyl group, 17a) a $C_1$-$C_{10}$ alkoxy $C_1$-$C_6$ alkyl group, 18a) a halo $C_1$-$C_6$ alkoxy $C_1$-$C_6$ alkyl group, 19a) a $C_2$-$C_6$ alkenyloxy $C_1$-$C_6$ alkyl group, 20a) a $C_1$-$C_6$ alkoxy $C_1$-$C_6$ alkoxy $C_1$-$C_6$ alkyl group, 21a) a $C_1$-$C_6$ alkylthio $C_1$-$C_6$ alkyl group, 22a) a halo $C_1$-$C_6$ alkylthio $C_1$-$C_6$ alkyl group, 23a) a $C_1$-$C_6$ alkylsulfinyl $C_1$-$C_6$ alkyl group, 24a) a halo $C_1$-$C_6$ alkylsulfinyl $C_1$-$C_6$ alkyl group, 25a) a $C_1$-$C_6$ alkylsulfonyl $C_1$-$C_6$ alkyl group, 26a) a halo $C_1$-$C_6$ alkylsulfonyl $C_1$-$C_6$ alkyl group, 27a) a mono $C_1$-$C_6$ alkylamino $C_1$-$C_6$ alkyl group, 28a) a di $C_1$-$C_6$ alkylamino $C_1$-$C_6$ alkyl group wherein the alkyl groups are the same or different, 29a) a phenyl $C_1$-$C_6$ alkoxy $C_1$-$C_6$ alkyl group, 30a) a substituted phenyl $C_1$-$C_6$ alkoxy $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 31a) a $C_1$-$C_{16}$ alkoxycarbonyl group, 32a) a $C_1$-$C_6$ alkoxy $C_1$-$C_6$ alkoxycarbonyl group, 33a) a halo $C_1$-$C_6$ alkoxycarbonyl group, 34a) a $C_2$-$C_6$ alkenyloxycarbonyl group, 35a) a $C_1$-$C_6$ alkylthiocarbonyl group, 36a) a mono $C_1$-$C_6$ alkylaminocarbonyl group, 37a) a di $C_1$-$C_6$ alkylaminocarbonyl group wherein the alkyl groups are the same or different, 38a) a $C_1$-$C_6$ alkoxycarbonyl $C_1$-$C_6$ alkyl group, 39a) a $C_1$-$C_6$ alkylsulfonyl group, 40a) a halo $C_1$-$C_6$ alkylsulfonyl group, 41a) a cyano $C_1$-$C_6$ alkyl group, 42a) a phenyl $C_1$-$C_6$ alkyl group, 43a) a substituted phenyl $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 44a) a phenylcarbonyl group, 45a) a substituted phenylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 46a) a heterocyclylcarbonyl group, 47a) a substituted heterocyclylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 48a) a phenoxycarbonyl group, 49a) a substituted phenoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 50a) a phenoxy $C_1$-$C_6$ alkylcarbonyl group, 51a) a substituted phenoxy $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 52a) a phenylsulfonyl group, 53a) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 54a) a di $C_1$-$C_6$ alkylphosphono group wherein the alkyl groups are the same or different, 55a) a di $C_1$-$C_6$ alkylphosphonothio group wherein the alkyl groups are the same or different, 56a) a N—$C_1$-$C_6$ alkyl-N—$C_1$-$C_6$ alkoxycarbonylaminothio group, 57a) a N—$C_1$-$C_6$ alkyl-N—$C_1$-$C_6$ alkoxycarbonyl $C_1$-$C_6$ alkylaminothio group, 58a) a di $C_1$-$C_6$ alkylaminothio group wherein the alkyl groups are the same or different, 59a) a $C_3$-$C_6$ cycloalkylcarbonyl group, 60a) a halo $C_3$-$C_6$ cycloalkylcarbonyl group, 61a) a $C_1$-$C_6$ alkyl $C_3$-$C_6$ cycloalkylcarbonyl group, 62a) a halo $C_1$-$C_6$ alkyl $C_3$-$C_6$ cycloalkylcarbonyl group, 63a) a phenyl $C_1$-$C_6$ alkylcarbonyl group, 64a) a substituted phenyl $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 65a) a phenyl $C_3$-$C_6$ cycloalkylcarbonyl group, 66a) a substituted phenyl $C_3$-$C_6$ cycloalkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 67a) a $C_3$-$C_6$ cycloalkyl $C_1$-$C_6$ alkylcarbonyl group, 68a) a $C_1$-$C_6$ alkoxy $C_1$-$C_6$ alkylcarbonyl group, 69a) a halo $C_3$-$C_6$ cycloalkyl $C_1$-$C_6$ alkylcarbonyl group, 70a) a phenoxy $C_1$-$C_6$ alkoxycarbonyl group, 71a) a substituted phenoxy $C_1$-$C_6$ alkoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 72a) a $C_1$-$C_6$ alkylcarbonyloxy $C_1$-$C_6$ alkyl group, 73a) a $C_1$-$C_6$ alkylcarbonyl $C_1$-$C_6$ alkylcarbonyl group, or 74a) a $C_1$-$C_6$ alkoxycarbonyl $C_1$-$C_6$ alkylcarbonyl group;

$R^2$ is 1b) a hydrogen atom, 2b) a halogen atom, 3b) a $C_1$-$C_6$ alkyl group, 4b) a halo $C_1$-$C_6$ alkyl group, 5b) a cyano group, 6b) a hydroxy group, 7b) a $C_1$-$C_6$ alkoxy group, 8b) a halo $C_1$-$C_6$ alkoxy group, 9b) a $C_1$-$C_6$ alkoxy $C_1$-$C_3$ alkoxy group, 10b) a halo $C_1$-$C_6$ alkoxy $C_1$-$C_3$ alkoxy group, 11b) a $C_1$-$C_6$ alkylthio $C_1$-$C_3$ alkoxy group, 12b) a halo $C_1$-$C_6$ alkylthio $C_1$-$C_3$ alkoxy group, 13b) a $C_1$-$C_6$ alkylsulfinyl $C_1$-$C_3$ alkoxy group, 14b) a halo $C_1$-$C_6$ alkylsulfinyl $C_1$-$C_3$ alkoxy group, 15b) a $C_1$-$C_6$ alkylsulfonyl $C_1$-$C_3$ alkoxy group, 16b) a halo $C_1$-$C_6$ alkylsulfonyl $C_1$-$C_3$ alkoxy group, 17b) a mono $C_1$-$C_6$ alkylamino $C_1$-$C_3$ alkoxy group, 18b) a di $C_1$-$C_6$ alkylamino $C_1$-$C_3$ alkoxy group wherein the alkyl groups are the same or different, 19b) a $C_1$-$C_6$ alkylthio group, 20b) a halo $C_1$-$C_6$ alkylthio group, 21b) a $C_1$-$C_6$ alkylsulfinyl group, 22b) a halo $C_1$-$C_6$ alkylsulfinyl group, 23b) a $C_1$-$C_6$ alkylsulfonyl group, 24b) a halo $C_1$-$C_6$ alkylsulfonyl group, 25b) an amino group, 26b) a mono $C_1$-$C_6$ alkylamino group, 27b) a di $C_1$-$C_6$ alkylamino group wherein the alkyl groups are the same or different, 28b) a phenoxy group, 29b) a substituted phenoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 30b) a phenylthio group, 31b) a substituted phenylthio group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 32b) a phenylsulfinyl group, 33b) a substituted phenylsulfinyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 34b) a phenylsulfonyl group, 35b) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 36b) a phenyl $C_1$-$C_6$ alkoxy group, or 37b) a substituted phenyl $C_1$-$C_6$ alkoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group;

G is 1c) a $C_2$-$C_{10}$ alkyl group, 2c) a halo $C_2$-$C_{10}$ alkyl group, 3c) a $C_3$-$C_{10}$ alkenyl group, 4c) a halo $C_3$-$C_{10}$ alkenyl group, 5c) a $C_3$-$C_{10}$ alkynyl group, 6c) a halo $C_3$-$C_{10}$ alkynyl group, 7c) a $C_3$-$C_{10}$ cycloalkyl group, 8c) a substituted $C_3$-$C_{10}$ cycloalkyl group having, on the ring, one or more, the same or different substituents selected from a) a halogen atom, b) a $C_1$-$C_6$ alkyl group, and c) a halo $C_1$-$C_6$ alkyl group, 9c) a $C_3$-$C_{10}$ cycloalkenyl group, 10c) a substituted $C_3$-$C_{10}$ cycloalkenyl group having, on the ring, one or more, the same or different substituents selected from a) a halogen atom, b) a $C_1$-$C_6$ alkyl group, and c) a halo $C_1$-$C_6$ alkyl group, 11c) a $C_3$-$C_8$ cycloalkyl $C_1$-$C_6$ alkyl group, or 12c) a halo $C_3$-$C_8$ cycloalkyl $C_1$-$C_6$ alkyl group;

Z is an oxygen atom or a sulfur atom;

X may be the same or different and is 1d) a hydrogen atom, 2d) a halogen atom, 3d) a cyano group, 4d) a nitro group, 5d) a $C_1$-$C_6$ alkyl group, or 6d) a halo $C_1$-$C_6$ alkyl group;

$Y^1$ is 1e) a hydrogen atom, 2e) a $C_1$-$C_6$ alkyl group, 3e) a halo $C_1$-$C_6$ alkyl group, 4e) a $C_2$-$C_6$ alkenyl group, 5e) a halo $C_2$-$C_6$ alkenyl group, 6e) a $C_2$-$C_6$ alkynyl group, 7e) a halo $C_2$-$C_6$ alkynyl group, 8e) a $C_1$-$C_6$ alkoxy $C_1$-$C_6$ alkoxy $C_1$-$C_6$ alkyl group, 9e) a hydroxy $C_1$-$C_6$ alkyl group, 10e) a $C_1$-$C_6$ alkylcarbonyloxy $C_1$-$C_6$ alkyl group, 11e) a $C_3$-$C_6$ cycloalkyl group, 12e) a halo $C_3$-$C_6$ cycloalkyl group, 13e) a $C_3$-$C_6$ cycloalkyl $C_1$-$C_6$ alkyl group, 14e) a halo $C_3$-$C_6$ cycloalkyl $C_1$-$C_6$ alkyl group, 15e) a $C_1$-$C_6$ alkylsulfonyl group, 16e) a halo $C_1$-$C_6$ alkylsulfonyl group, 17e) a $C_1$-$C_6$ alkylthio $C_1$-$C_6$ alkyl group, 18e) a halo $C_1$-$C_6$ alkylthio $C_1$-$C_6$ alkyl group, 19e) a $C_1$-$C_6$ alkylsulfinyl $C_1$-$C_6$ alkyl group, 20e) a halo $C_1$-$C_6$ alkylsulfinyl $C_1$-$C_6$ alkyl group, 21e) a $C_1$-$C_6$ alkylsulfonyl $C_1$-$C_6$ alkyl group, 22e) a halo $C_1$-$C_6$ alkylsulfonyl $C_1$-$C_6$ alkyl group, 23e) a mono $C_1$-$C_6$ alkylamino $C_1$-$C_6$ alkyl group, 24e) a di $C_1$-$C_6$ alkylamino $C_1$-$C_6$ alkyl group wherein the alkyl groups are the same or different, 25e) a phenyl group, 26e) a substituted phenyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group;

$Y^2$ may be the same or different and is 1f) a hydrogen atom, 2f) a halogen atom, 3f) a cyano group, 4f) a nitro group, 5f) a hydroxyl group, 6f) a mercapto group, 7f) an amino group, 8f) a carboxyl group, 9f) a $C_1$-$C_6$ alkyl group, 10f) a halo $C_1$-$C_6$ alkyl group, 11f) a $C_2$-$C_6$ alkenyl group, 12f) a halo $C_2$-$C_6$ alkenyl group, 13f) a $C_2$-$C_6$ alkynyl group, 14f) a halo $C_2$-$C_6$ alkynyl group, 15f) a tri $C_1$-$C_6$ alkylsilyl $C_2$-$C_6$ alkynyl group wherein the alkyl groups are the same or different, 16f) a phenyl $C_2$-$C_6$ alkynyl group, 17f) a $C_1$-$C_6$ alkoxy $C_1$-$C_6$ alkoxy $C_1$-$C_6$ alkyl group, 18f) a hydroxy $C_1$-$C_6$ alkyl group, 19f) a $C_1$-$C_6$ alkylcarbonyloxy $C_1$-$C_6$ alkyl group, 20f) a $C_3$-$C_6$ cycloalkyl group, 21f) a halo $C_3$-$C_6$ cycloalkyl group, 22f) a $C_3$-$C_6$ cycloalkyl $C_1$-$C_6$ alkyl group, 23f) a halo $C_3$-$C_6$ cycloalkyl $C_1$-$C_6$ alkyl group, 24f) a $C_1$-$C_6$ alkoxy group, 25f) a halo $C_1$-$C_6$ alkoxy group, 26f) a $C_1$-$C_6$ alkoxy $C_1$-$C_6$ alkoxy group, 27f) a halo $C_1$-$C_6$ alkoxy $C_1$-$C_6$ alkoxy group, 28f) a phenyl $C_1$-$C_6$ alkoxy group, 29f) a $C_1$-$C_6$ alkoxy $C_1$-$C_6$ alkyl group, 30f) a halo $C_1$-$C_6$ alkoxy $C_1$-$C_6$ alkyl group, 31f) a $C_1$-$C_6$ alkylthio group, 32f) a halo $C_1$-$C_6$ alkylthio group, 33f) a $C_1$-$C_6$ alkylsulfinyl group, 34f) a halo $C_1$-$C_6$ alkylsulfinyl group, 35f) a $C_1$-$C_6$ alkylsulfonyl group, 36f) a halo $C_1$-$C_6$ alkylsulfonyl group, 37f) a $C_1$-$C_6$ alkylthio $C_1$-$C_6$ alkyl group, 38f) a halo $C_1$-$C_6$ alkylthio $C_1$-$C_6$ alkyl group, 39f) a $C_1$-$C_6$ alkylsulfinyl $C_1$-$C_6$ alkyl group, 40f) a halo $C_1$-$C_6$ alkylsulfinyl $C_1$-$C_6$ alkyl group, 41f) a $C_1$-$C_6$ alkylsulfonyl $C_1$-$C_6$ alkyl group, 42f) a halo $C_1$-$C_6$ alkylsulfonyl $C_1$-$C_6$ alkyl group, 43f) a mono $C_1$-$C_6$ alkylamino group, 44f) a di $C_1$-$C_6$ alkylamino group wherein the alkyl groups are the same or different, 45f) a phenylamino group, 46f) a mono $C_1$-$C_6$ alkylamino $C_1$-$C_6$ alkyl group, 47f) a di $C_1$-$C_6$ alkylamino $C_1$-$C_6$ alkyl group wherein the alkyl groups are the same or different, 48f) a phenyl group, 49f) a substituted phenyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 50f) a phenoxy group, 51f) a substituted phenoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 52f) a heterocyclic group, or 53f) a substituted heterocyclic group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group;

m is 1 or 2; and n is an integer of 1-3, salts thereof and agrohorticultural agents containing the compound as an active ingredient, and methods of use thereof.

In addition, the present invention also relates to substituted aniline derivatives represented by the formula (II), which are intermediates therefor:

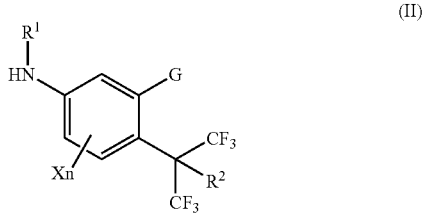

(II)

wherein $R^1$ is 1a) a hydrogen atom, 2a) a $C_1$-$C_8$ alkyl group, 3a) a halo $C_1$-$C_6$ alkyl group, 4a) a $C_1$-$C_6$ alkylcarbonyl group, 5a) a halo $C_1$-$C_6$ alkylcarbonyl group, 6a) a $C_2$-$C_6$ alkenylcarbonyl group, 7a) a halo $C_2$-$C_6$ alkenylcarbonyl group, 8a) a $C_1$-$C_6$ alkylcarbonyl $C_1$-$C_6$ alkyl group, 9a) a $C_3$-$C_6$ cycloalkyl group, 10a) a halo $C_3$-$C_6$ cycloalkyl group, 11a) a $C_3$-$C_6$ cycloalkyl $C_1$-$C_6$ alkyl group, 12a) a halo $C_3$-$C_6$ cycloalkyl $C_1$-$C_6$ alkyl group, 13a) a $C_2$-$C_6$ alkenyl group, 14a) a halo $C_2$-$C_6$ alkenyl group, 15a) a $C_2$-$C_6$ alkynyl group, 16a) a halo $C_2$-$C_6$ alkynyl group, 17a) a $C_1$-$C_{10}$ alkoxy $C_1$-$C_6$ alkyl group, 18a) a halo $C_1$-$C_6$ alkoxy $C_1$-$C_6$ alkyl group, 19a) a $C_2$-$C_6$ alkenyloxy $C_1$-$C_6$ alkyl group, 20a) a $C_1$-$C_6$ alkoxy $C_1$-$C_6$ alkoxy $C_1$-$C_6$ alkyl group, 21a) a $C_1$-$C_6$ alkylthio $C_1$-$C_6$ alkyl group, 22a) a halo $C_1$-$C_6$ alkylthio $C_1$-$C_6$ alkyl group, 23a) a $C_1$-$C_6$ alkylsulfinyl $C_1$-$C_6$ alkyl group, 24a) a halo $C_1$-$C_6$ alkylsulfinyl $C_1$-$C_6$ alkyl group, 25a) a $C_1$-$C_6$ alkylsulfonyl $C_1$-$C_6$ alkyl group, 26a) a halo $C_1$-$C_6$ alkylsulfonyl $C_1$-$C_6$ alkyl group, 27a) a mono $C_1$-$C_6$ alkylamino $C_1$-$C_6$ alkyl group, 28a) a di $C_1$-$C_6$ alkylamino $C_1$-$C_6$ alkyl group wherein the alkyl groups are the same or different, 29a) a phenyl $C_1$-$C_6$ alkoxy $C_1$-$C_6$ alkyl group, 30a) a substituted phenyl $C_1$-$C_6$ alkoxy $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 31a) a $C_1$-$C_{16}$ alkoxycarbonyl group, 32a) a $C_1$-$C_6$ alkoxy $C_1$-$C_6$ alkoxycarbonyl group, 33a) a halo $C_1$-$C_6$ alkoxycarbonyl group, 34a) a $C_2$-$C_6$ alkenyloxycarbonyl group, 35a) a $C_1$-$C_6$ alkylthiocarbonyl group, 36a) a mono $C_1$-$C_6$ alkylaminocarbonyl group, 37a) a di $C_1$-$C_6$ alkylaminocarbonyl group wherein the alkyl groups are the same or different, 38a) a $C_1$-$C_6$ alkoxycarbonyl $C_1$-$C_6$ alkyl group, 39a) a $C_1$-$C_6$ alkylsulfonyl group, 40a) a halo $C_1$-$C_6$ alkylsulfonyl group, 41a) a cyano $C_1$-$C_6$ alkyl group, 42a) a phenyl $C_1$-$C_6$ alkyl group, 43a) a substituted phenyl $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 44a) a phenylcarbonyl group, 45a) a substituted phenylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 46a) a heterocyclylcarbonyl group, 47a) a substituted heterocyclylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 48a) a phenoxycarbonyl group, 49a) a substituted phenoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 50a) a phenoxy $C_1$-$C_6$ alkylcarbonyl group, 51a) a substituted phenoxy $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 52a) a phenylsulfonyl group, 53a) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 54a) a di $C_1$-$C_6$ alkylphosphono group wherein the alkyl groups are the same or different, 55a) a di $C_1$-$C_6$ alkylphosphonothio group wherein the alkyl groups are the same or different, 56a) a N—$C_1$-$C_6$ alkyl-N—$C_1$-$C_6$ alkoxycarbonylaminothio group, 57a) a N—$C_1$-$C_6$ alkyl-N—$C_1$-$C_6$ alkoxycarbonyl $C_1$-$C_6$ alkylaminothio group, 58a) a di $C_1$-$C_6$ alkylaminothio group wherein the alkyl groups are the same or different, 59a) a $C_3$-$C_6$ cycloalkylcarbonyl group, 60a) a halo $C_3$-$C_6$ cycloalkylcarbonyl group, 61a) a $C_1$-$C_6$ alkyl $C_3$-$C_6$ cycloalkylcarbonyl group, 62a) a halo $C_1$-$C_6$ alkyl $C_3$-$C_6$ cycloalkylcarbonyl group, 63a) a phenyl $C_1$-$C_6$ alkylcarbonyl group, 64a) a substituted phenyl $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 65a) a phenyl $C_3$-$C_6$ cycloalkylcarbonyl group, 66a) a substituted phenyl $C_3$-$C_6$ cycloalkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 67a) a $C_3$-$C_6$ cycloalkyl $C_1$-$C_6$ alkylcarbonyl group, 68a) a $C_1$-$C_6$ alkoxy $C_1$-$C_6$ alkylcarbonyl group, 69a) a halo $C_3$-$C_6$ cycloalkyl $C_1$-$C_6$ alkylcarbonyl group, 70a) a phenoxy $C_1$-$C_6$ alkoxycarbonyl group, 71a) a substituted phenoxy $C_1$-$C_6$ alkoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 72a) a $C_1$-$C_6$ alkylcarbonyloxy $C_1$-$C_6$ alkyl group, 73a) a $C_1$-$C_6$ alkylcarbonyl $C_1$-$C_6$ alkylcarbonyl group, or 74a) a $C_1$-$C_6$ alkoxycarbonyl $C_1$-$C_6$ alkylcarbonyl group;

$R^2$ is 1b) a hydrogen atom, 2b) a halogen atom, 3b) a $C_1$-$C_6$ alkyl group, 4b) a halo $C_1$-$C_6$ alkyl group, 5b) a cyano group, 6b) a hydroxy group, 7b) a $C_1$-$C_6$ alkoxy group, 8b) a halo $C_1$-$C_6$ alkoxy group, 9b) a $C_1$-$C_6$ alkoxy $C_1$-$C_3$ alkoxy group, 10b) a halo $C_1$-$C_6$ alkoxy $C_1$-$C_3$ alkoxy group, 11b) a $C_1$-$C_6$ alkylthio $C_1$-$C_3$ alkoxy group, 12b) a halo $C_1$-$C_6$ alkylthio $C_1$-$C_3$ alkoxy group, 13b) a $C_1$-$C_6$ alkylsulfinyl $C_1$-$C_3$ alkoxy group, 14b) a halo $C_1$-$C_6$ alkylsulfinyl $C_1$-$C_3$ alkoxy group, 15b) a $C_1$-$C_6$ alkylsulfonyl $C_1$-$C_3$ alkoxy group, 16b) a halo $C_1$-$C_6$ alkylsulfonyl $C_1$-$C_3$ alkoxy group, 17b) a mono $C_1$-$C_6$ alkylamino $C_1$-$C_3$ alkoxy group, 18b) a di $C_1$-$C_6$ alkylamino $C_1$-$C_3$ alkoxy group wherein the alkyl groups are the same or different, 19b) a $C_1$-$C_6$ alkylthio group, 20b) a halo $C_1$-$C_6$ alkylthio group, 21b) a $C_1$-$C_6$ alkylsulfinyl group, 22b) a halo $C_1$-$C_6$ alkylsulfinyl group, 23b) a $C_1$-$C_6$ alkylsulfonyl group, 24b) a halo $C_1$-$C_6$ alkylsulfonyl group, 25b) an amino group, 26b) a mono $C_1$-$C_6$ alkylamino group, 27b) a di $C_1$-$C_6$ alkylamino group wherein the alkyl groups are the same or different, 28b) a phenoxy group, 29b) a substituted phenoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 30b) a phenylthio group, 31b) a substituted phenylthio group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 32b) a phenylsulfinyl group, 33b) a substituted phenylsulfinyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 34b) a phenylsulfonyl group, 35b) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 36b) a phenyl $C_1$-$C_6$ alkoxy group, or 37b) a substituted phenyl $C_1$-$C_6$ alkoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group;

G is 1c) a $C_2$-$C_{10}$ alkyl group, 2c) a halo $C_2$-$C_{10}$ alkyl group, 3c) a $C_3$-$C_{10}$ alkenyl group, 4c) a halo $C_3$-$C_{10}$ alkenyl group, 5c) a $C_3$-$C_{10}$ alkynyl group, 6c) a halo $C_3$-$C_{10}$ alkynyl group, 7c) a $C_3$-$C_{10}$ cycloalkyl group, 8c) a substituted $C_3$-$C_{10}$ cycloalkyl group having, on the ring, one or more, the same or different substituents selected from a) a halogen atom, b) a $C_1$-$C_6$ alkyl group, and c) a halo $C_1$-$C_6$ alkyl group, 9c) a $C_3$-$C_{10}$ cycloalkenyl group, 10c) a substituted $C_3$-$C_{10}$ cycloalkenyl group having, on the ring, one or more, the same or different substituents selected from a) a halogen atom, b) a $C_1$-$C_6$ alkyl group, and c) a halo $C_1$-$C_6$ alkyl group, 11c) a $C_3$-$C_8$ cycloalkyl $C_1$-$C_6$ alkyl group, or 12c) a halo $C_3$-$C_8$ cycloalkyl $C_1$-$C_6$ alkyl group;

X may be the same or different and is 1d) a hydrogen atom, 2d) a halogen atom, 3d) a cyano group, 4d) a nitro group, 5d) a $C_1$-$C_6$ alkyl group, or 6d) a halo $C_1$-$C_6$ alkyl group;

n is an integer of 1-3, salts thereof and 1,3-dimethyl-5-trifluoromethylpyrazole-4-carboxylic acid and a salt thereof.

BEST MODE FOR EMBODYING THE INVENTION

In the definitions of a substituted pyrazolecarboxanilide derivative of the formula (I) and a substituted aniline derivative of the formula (II) of the present invention, "halo", "$C_1$-$C_6$ alkyl", "$C_1$-$C_6$ alkoxyl", "$C_2$-$C_6$ alkenyl", "$C_2$-$C_6$ alkynyl" or "a heterocyclic group", and the like in each of substituents has the following meaning.

The "halo" or "halogen atom" means a chlorine atom, a bromine atom, an iodine atom or a fluorine atom.

The "$C_1$-$C_6$ alkyl" is linear or branched chain alkyl having 1 to 6 carbon atoms, such as methyl, ethyl, n-propyl, i-propyl, n-butyl, i-butyl, s-butyl, t-butyl, n-pentyl, isopentyl, neopentyl, t-pentyl, 2-methylbutyl, 1-ethylpropyl, n-hexyl, 2-ethylbutyl and the like.

The "$C_1$-$C_8$ alkyl" is linear or branched chain alkyl having 1 to 8 carbon atoms, such as methyl, ethyl, n-propyl, i-propyl, n-butyl, i-butyl, s-butyl, t-butyl, n-pentyl, isopentyl, neopentyl, t-pentyl, 2-methylbutyl, 1-ethylpropyl, n-hexyl, 2-ethylbutyl, n-heptyl, n-octyl, 2-ethylhexyl and the like.

The "$C_2$-$C_{10}$ alkyl" is linear or branched chain alkyl having 2 to 10 carbon atoms, such as ethyl, n-propyl, i-propyl, n-butyl, i-butyl, s-butyl, t-butyl, n-pentyl, isopentyl, neopentyl, t-pentyl, 2-methylbutyl, n-hexyl, 2-ethylbutyl, 1-ethylpropyl, n-heptyl, n-octyl, 2-ethylhexyl, n-nonyl, n-decyl and the like.

The "$C_3$-$C_6$ cycloalkyl" is cyclic alkyl having 3 to 6 carbon atoms, such as cyclopropyl, cyclobutyl, cyclopentyl, cyclohexyl and the like.

The "$C_3$-$C_8$ cycloalkyl" is cyclic alkyl having 3 to 8 carbon atoms, such as cyclopropyl, cyclobutyl, cyclopentyl, cyclohexyl, cyclooctyl and the like.

The "$C_3$-$C_{10}$ cycloalkyl" is cyclic alkyl having 3 to 10 carbon atoms, such as cyclopropyl, cyclobutyl, cyclopentyl, cyclohexyl, cyclooctyl, cyclodecyl and the like.

The "$C_3$-$C_{10}$ cycloalkenyl" is cyclic alkenyl having 3 to 10 carbon atoms, such as cyclopropenyl, cyclobutenyl, cyclopentenyl, cyclohexenyl, cyclooctenyl, cyclodecenyl and the like.

The "$C_1$-$C_3$ alkoxy" is alkoxy wherein its alkyl moiety is linear or branched chain alkyl having 1 to 3 carbon atoms, such as methoxy, ethoxy, propoxy, isopropoxy and the like.

The "$C_1$-$C_6$ alkoxy" is alkoxy wherein its alkyl moiety is the above-mentioned "$C_1$-$C_6$ alkyl", such as methoxy, ethoxy, n-propoxy, i-propoxy, n-butoxy, isobutoxy, s-butoxy, t-butoxy, n-pentyloxy, isopentyloxy, neopentyloxy, t-pentyloxy, 2-methylbutoxy, 1-ethylpropoxy, hexyloxy, 2-ethylbutoxy and the like.

The "$C_1$-$C_{10}$ alkoxy" is alkoxy wherein its alkyl moiety is linear or branched chain alkyl having 1 to 10 carbon atoms, such as methoxy, ethoxy, n-propoxy, i-propoxy, n-butoxy, isobutoxy, s-butoxy, t-butoxy, n-pentyloxy, isopentyloxy, neopentyloxy, t-pentyloxy, 2-methylbutoxy, 1-ethylpropoxy, hexyloxy, 2-ethylbutoxy, n-heptyloxy, n-octyloxy, 2-ethylhexyloxy, n-nonyloxy, n-decyloxy and the like.

The "$C_1$-$C_{16}$ alkoxy" is alkoxy wherein its alkyl moiety is linear or branched chain alkyl having 1 to 16 carbon atoms, such as methoxy, ethoxy, n-propoxy, i-propoxy, n-butoxy, isobutoxy, s-butoxy, t-butoxy, n-pentyloxy, isopentyloxy, neopentyloxy, t-pentyloxy, 2-methylbutoxy, 1-ethylpropoxy, hexyloxy, 2-ethylbutoxy, n-heptyloxy, n-octyloxy, 2-ethylhexyloxy, n-nonyloxy, n-decyloxy, n-undecyloxy, n-dodecyloxy, n-tridecyloxy, n-tetradecyloxy, n-pentadecyloxy, n-hexadecyloxy and the like.

The "$C_2$-$C_6$ alkenyl" is linear or branched chain alkenyl having 2 to 6 carbon atoms, which has at least one double bond, such as vinyl, 1-propenyl, allyl, 1-butenyl, 2-butenyl, 3-butenyl, 2-pentenyl, 2-methyl-1-propenyl, 2,4-pentadienyl, 3-hexenyl and the like.

The "$C_3$-$C_{10}$ alkenyl" is linear or branched chain alkenyl having 3 to 10 carbon atoms, which has at least one double bond, such as 1-butenyl, 2-butenyl, 3-butenyl, 2-pentenyl, 2,4-pentadienyl, 3-hexenyl, 3-heptenyl, 3-octenyl, 3-nonenyl, 3-decenyl and the like.

The "$C_2$-$C_6$ alkynyl" is linear or branched chain alkynyl having 2 to 6 carbon atoms, which has at least one triple bond, such as ethynyl, 2-propynyl, 1-butynyl, 2-butynyl, 3-butynyl, 2-pentynyl, 3-hexynyl and the like.

The "$C_3$-$C_{10}$ alkynyl" is linear or branched chain alkynyl having 3 to 10 carbon atoms, which has at least one triple bond, such as 1-butynyl, 2-butynyl, 3-butynyl, 2-pentynyl, 3-hexynyl, 3-heptynyl, 3-octynyl, 3-nonynyl, 3-decynyl and the like.

The numbers in "$C_2$-$C_6$", "$C_3$-$C_{10}$" and the like shows the range of carbon atom numbers such as 2 to 6 carbon atoms and 3 to 10 carbon atoms.

Moreover, the above-mentioned definitions can apply to groups wherein the above-mentioned substituents are connected. For example, "halo $C_1$-$C_6$ alkyl" means linear or branched chain alkyl group having 1 to 6 carbon atoms, which is substituted by the same or different one or more halogen atoms, such as chloromethyl, 2-chloroethyl, 2,2,2-trichloroethyl, 3-chloropropyl, 2-chloro-1,1-dimethylethyl, 1-bromo- 1-methylethyl, difluoromethyl, trifluoromethyl, 2,2,2-trifluoroethyl, perfluorohexyl and the like.

"A heterocyclic group" and "A heterocyclyl" are 5- or 6-membered heterocyclic groups having one or more hetero atoms selected from an oxygen atom, a sulfur atom and a nitrogen atom including, for example, pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group and pyrazolyl group.

A salt of a substituted pyrazolecarboxanilide derivative represented by the formula (I) of the present invention includes a salt of an alkali metal (lithium, sodium, potassium, etc.); a salt of an alkaline earth metal (calcium, magnesium, etc.); an ammonium salt; and a salt of an organic amine (methylamine, triethylamine, diethanolamine, piperidine, pyridine, etc.), or an acid addition salt. The acid addition salt includes, for example, a carboxylate such as acetate, propionate, oxalate, trifluoroacetate, benzoate and the like; a sulfonate such as methanesulfonate, trifluoromethanesulfonate, p-toluenesulfonate and the like; an inorganic acid salt such as a hydrochloride, a sulfate, a nitrate, a carbonate and the like.

In the substituted pyrazolecarboxanilide derivatives represented by the formula (I) of the present invention, $R^1$ is preferably 1a) a hydrogen atom, 2a) a $C_1$-$C_6$ alkyl group, 3a) a halo $C_1$-$C_6$ alkyl group, 4a) a $C_1$-$C_6$ alkylcarbonyl group, 5a) a halo $C_1$-$C_6$ alkylcarbonyl group, 6a) a $C_2$-$C_6$ alkenylcarbonyl group, 13a) a $C_2$-$C_6$ alkenyl group, 17a) a $C_1$-$C_{10}$ alkoxy $C_1$-$C_6$ alkyl group, 18a) a halo $C_1$-$C_6$ alkoxy $C_1$-$C_6$ alkyl group, 19a) a $C_2$-$C_6$ alkenyloxy $C_1$-$C_6$ alkyl group, 20a) a $C_1$-$C_6$ alkoxy $C_1$-$C_6$ alkoxy $C_1$-$C_6$ alkyl group, 29a) a phenyl $C_1$-$C_6$ alkoxy $C_1$-$C_6$ alkyl group, 30a) a substituted phenyl $C_1$-$C_6$ alkoxy $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 31a) a $C_1$-$C_{16}$ alkoxycarbonyl group, 32a) a $C_1$-$C_6$ alkoxy $C_1$-$C_6$ alkoxycarbonyl group, 33a) a halo $C_1$-$C_6$ alkoxycarbonyl group, 34a) a $C_2$-$C_6$ alkenyloxycarbonyl group, 35a) a $C_1$-$C_6$ alkylthiocarbonyl group, 42a) a phenyl $C_1$-$C_6$ alkyl group, 43a) a substituted phenyl $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 44a) a phenylcarbonyl group, 45a) a substituted phenylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 46a) a heterocyclylcarbonyl group, 47a) a substituted heterocyclylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 48a) a phenoxycarbonyl group, 49a) a substituted phenoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 50a) a phenoxy $C_1$-$C_6$ alkylcarbonyl group, 51a) a substituted phenoxy $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 52a) a phenylsulfonyl group, 53a) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 58a) a di $C_1$-$C_6$ alkylaminothio group wherein the alkyl groups are the same or different, 59a) a $C_3$-$C_6$ cycloalkylcarbonyl group, 61a) a $C_1$-$C_6$ alkyl $C_3$-$C_6$ cycloalkylcarbonyl group, 63a) a phenyl $C_1$-$C_6$ alkylcarbonyl group, 64a) a substituted phenyl $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 65a) a phenyl $C_3$-$C_6$ cycloalkylcarbonyl group, 66a) a substituted phenyl $C_3$-$C_6$ cycloalkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 68a) a $C_1$-$C_6$ alkoxy $C_1$-$C_6$ alkylcarbonyl group, 73a) a $C_1$-$C_6$ alkylcarbonyl $C_1$-$C_6$ alkylcarbonyl group, or 74a) a $C_1$-$C_6$ alkoxycarbonyl $C_1$-$C_6$ alkylcarbonyl group, and more preferably 1a) a hydrogen atom, 4a) a $C_1$-$C_6$ alkylcarbonyl group, 5a) a halo $C_1$-$C_6$ alkylcarbonyl group, 17a) a $C_1$-$C_{10}$ alkoxy $C_1$-$C_6$ alkyl group, 18a) a halo $C_1$-$C_6$ alkoxy $C_1$-$C_6$ alkyl group, 31a) a $C_1$-$C_{16}$ alkoxycarbonyl group, 33a) a halo $C_1$-$C_6$ alkoxycarbonyl group or 68a) a $C_1$-$C_6$ alkoxy $C_1$-$C_6$ alkylcarbonyl group.

$R^2$ is preferably 1b) a hydrogen atom, 2b) a halogen atom, 6b) a hydroxy group, 7b) a $C_1$-$C_6$ alkoxy group or 8b) a halo $C_1$-$C_6$ alkoxy group, and more preferably 1b) a hydrogen atom or 7b) a $C_1$-$C_6$ alkoxy group.

G is preferably 1c) a $C_2$-$C_{10}$ alkyl group, 3c) a $C_3$-$C_{10}$ alkenyl group, or 11c) a $C_3$-$C_8$ cycloalkyl $C_1$-$C_6$ alkyl group, and more preferably 1c) a $C_2$-$C_{10}$ alkyl group.

X is preferably 1d) a hydrogen atom, 2d) a halogen atom, or 5d) a $C_1$-$C_6$ alkyl group, and more preferably 1d) a hydrogen atom.

Z is preferably an oxygen atom.

$Y^1$ is preferably 2e) a $C_1$-$C_6$ alkyl group, 3e) a halo $C_1$-$C_6$ alkyl group, or 4e) a $C_2$-$C_6$ alkenyl group, and more preferably 2e) a $C_1$-$C_6$ alkyl group.

$Y^2$ is preferably 1f) a hydrogen atom, 2f) a halogen atom, 9f) a $C_1$-$C_6$ alkyl group, 10f) a halo $C_1$-$C_6$ alkyl group, or 31f) a $C_1$-$C_6$ alkylthio group, and more preferably 1f) a hydrogen atom, 2f) a halogen atom, 9f) a $C_1$-$C_6$ alkyl group, or 10f) a halo $C_1$-$C_6$ alkyl group.

m is preferably 2.

In addition, a salt of a substituted aniline derivative represented by the formula (II) is preferably an acid addition salt including, for example, a carboxylate such as acetate, propionate, oxalate, trifluoroacetate, benzoate and the like; a sulfonate such as methanesulfonate, trifluoromethanesulfonate, p-toluenesulfonate and the like; an inorganic acid salt such as a hydrochloride, a sulfate, a nitrate, a carbonate and the like.

A salt of 1,3-dimethyl-5-trifluoromethylpyrazole-4-carboxylic acid of the present invention includes a salt of an alkali metal (lithium, sodium, potassium, etc.); a salt of an alkaline earth metal (calcium, magnesium, etc.); an ammonium salt; and a salt of an organic amine (methylamine, triethylamine, diethanolamine, piperidine, pyridine, etc.).

A substituted pyrazolecarboxanilide derivative represented by the formula (I) or an intermediate thereof, i.e. a substituted aniline derivative represented by the formula (II), of the present invention may contain one or plural numbers of asymmetric centers in the structural formula, and further two or more optical isomers and diastereomers may be present. Consequently, the present invention entirely encompasses each optical isomer and the mixtures with any ratio thereof. In addition, a substituted pyrazolecarboxanilide derivative represented by the formula (I) of the present invention may have two types of geometric isomers derived from a C—C double bond in the structural formula. The present invention encompasses all of geometric isomers and the mixtures containing them in any ratio. Moreover, the present invention encompasses hydrates thereof.

Representative production methods for a substituted pyrazolecarboxanilide derivative represented by the formula (I) and a substituted aniline derivative represented by the formula (II), as an intermediate thereof are illustrated hereinbelow, but the present invention should not be construed as limiting thereto.

Production Method 1

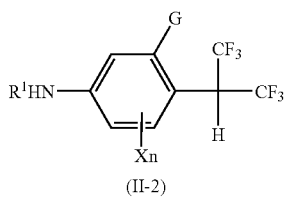

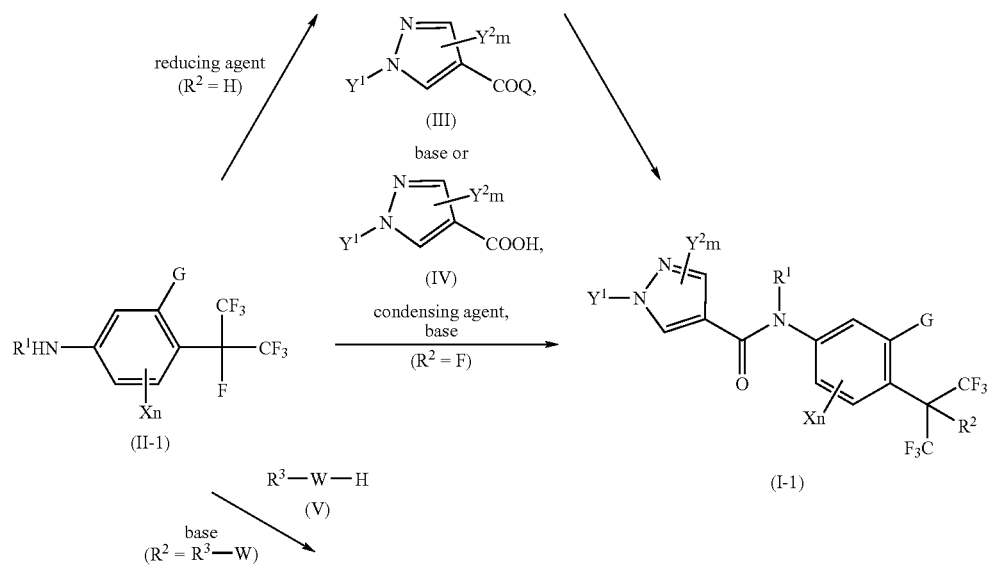

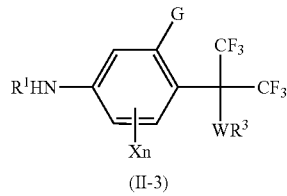

(II-3)

(wherein G, $R^1$, X, n, $Y^1$, $Y^2$ and m are as defined above; and $R^3$ is a hydrogen atom, a $C_1$-$C_6$ alkyl group, a halo $C_1$-$C_6$ alkyl group, a phenyl group, a substituted phenyl group or a phenyl $C_1$-$C_4$ alkyl group; W is —O—, —S— or —N($R^4$)—, wherein $R^4$ is a hydrogen atom, a $C_1$-$C_6$ alkyl group, a halo $C_1$-$C_6$ alkyl group, a phenyl group, a substituted phenyl group or a phenyl $C_1$-$C_4$ alkyl group; and Q is a halogen atom or a $C_1$-$C_6$ alkoxyl group).

Among a substituted pyrazolecarboxanilide derivative represented by the formula (I), a substituted pyrazolecarboxanilide derivative (I-1) wherein Z is O, and $R^2$ is a hydrogen atom, a fluorine atom or $WR^3$ wherein W and $R^3$ are as defined above can be produced by reacting an aniline derivative represented by the formulas (II-1) to (II-3) with a pyrazolecarboxylic halide or a pyrazolecarboxylate ester represented by the formula (III) in the presence or absence of a base in an inert solvent, or by reacting an aniline derivative represented by the formulas (II-1) to (II-3) with a pyrazolecarboxylic acid represented by the formula (IV) in the presence of a condensing agent, in the presence or absence of a base, in an inert solvent, and any usual production methods for amides may be applicable.

An aniline derivative represented by the formula (II-2) can be produced by reducing an aniline derivative represented by the formula (II-1) in the presence of a reducing agent, in an inert solvent.

An aniline derivative represented by the formula (II-3) can be produced by reacting an aniline derivative represented by the formula (II-1) with an alcohol derivative, a thiol derivative or an amine derivative represented by the formula (V), in the presence or absence of a base in an inert solvent.

The Formula (II-1)→the Formula (II-2)

An example of a reducing agent to be used in the present reaction includes metal hydrides such as lithium aluminum hydride, lithium borohydride, sodium borohydride, diisobutyl aluminum hydride, sodium bis(2-methoxyethoxy)aluminum hydride and the like, metal such as lithium and the like or metal salts, and the like. The amount of the reducing agent to be used may be selected, as appropriate, in the range from equivalent to excess amount relative to an aniline derivative represented by the formula (II-1).

An example of an inert solvent to be used in the present reaction, which may be any one as long as it does not significantly inhibit progress of the present reaction, includes aromatic hydrocarbons such as benzene, toluene, xylene and the like; halogenated hydrocarbons such as methylene chloride, chloroform, carbon tetrachloride and the like; halogenated aromatic hydrocarbons such as chlorobenzene, dichlorobenzene and the like; straight chain or cyclic ethers such as diethyl ether, dioxane, tetrahydrofuran and the like, or dimethylsulfoxide and the like and these inert solvents can be used alone or in combination of two or more kinds.

Reaction temperature may be in the range from room temperature to boiling temperature of an inert solvent to be used and reaction time may be in the range from several minutes to 50 hours, while depending on reaction scale and reaction temperature.

After completion of the reaction, desired compound may be isolated from the reaction mixture by a conventional method and the desired compound can be produced by purification using recrystallization or column chromatography, etc, if necessary. The desired compound may also be subjected to subsequent reaction step without isolation from the reaction mixture.

The formula (II-1)→the Formula (II-3)

An example of a base to be used in the present reaction includes metal hydrides such as lithium hydride, sodium hydride, potassium hydride and the like; metal alcoholates such as sodium methoxide, sodium ethoxide, potassium tert-butoxide and the like; and alkyl metals such as n-butyl lithium, sec-butyl lithium, tert-butyl lithium and the like. The amount of the base to be used may be selected, as appropriate, in the range from equivalent to excess amount relative to an aniline derivative represented by the formula (II-1).

As an example of an inert solvent to be used in the present reaction, which may be any one as long as it does not significantly inhibit progress of the present reaction, includes aromatic hydrocarbons such as benzene, toluene, xylene and the like; alcohols such as methanol, ethanol and the like; straight chain or cyclic ethers such as diethyl ether, 1,2-dimethoxyethane, dioxane, tetrahydrofuran and the like, and the like and these inert solvents can be used alone or in combination of two or more kinds.

Reaction temperature may be in the range from –70° C. to boiling temperature of an inert solvent to be used and reaction time may be in the range from several minutes to 50 hours, while depending on reaction scale and reaction temperature.

After completion of the reaction, desired compound may be isolated from the reaction mixture by a conventional method and the desired compound can be produced by purification using recrystallization or column chromatography, etc, if necessary. The desired compound may also be subjected to subsequent reaction step without isolation from the reaction mixture.

The Formula (II-1), (II-2) or (II-3)→the Formula (I-1)

An example of a condensing agent to be used in the present reaction includes diethyl cyanophosphate (DEPC), carbonyldiimidazole (CDI), 1,3-dicyclohexylcarbodiimide (DCC), chloroformates, 2-chloro-1-methylpyridinium iodide and the like.

As a base to be used in the present reaction, an inorganic base or an organic base is included and an example of an inorganic base includes alkali metal hydroxides such as sodium hydroxide, potassium hydroxide and the like; alkali metal hydrides such as sodium hydride, potassium hydride and the like; alkali metal salts of alcohol such as sodium ethoxide, potassium tert-butoxide and the like; carbonates such as sodium carbonate, potassium carbonate, sodium hydrogen carbonate and the like; and an example of organic bases includes triethylamine, pyridine, DBU and the like. The amount of the base to be used may be selected in the range from equivalent to excess amount relative to a pyrazolecarboxylic acid derivative represented by the formula (III) or (IV).

An example of an inert solvent to be used in the present reaction, which may be any one as long as it does not significantly inhibit progress of the present reaction, includes aromatic hydrocarbons such as benzene, toluene, xylene and the like; halogenated hydrocarbons such as methylene chloride, chloroform, carbon tetrachloride and the like; halogenated aromatic hydrocarbons such as chlorobenzene, dichlorobenzene and the like; straight chain or cyclic ethers such as diethyl ether, dioxane, tetrahydrofuran and the like; esters such as ethyl acetate and the like; amides such as dimethylformamide, dimethylacetamide and the like; dimethylsulfoxide; 1,3-dimethyl-2-imidazolidinone; acetone, methyl ethyl ketone and the like. These inert solvents can be used alone or in combination of two or more kinds.

As the present reaction is an equimolar reaction, each reactant may be used in equal mole, however, any of the reactants may also be used in excess. Reaction temperature may be in the range from room temperature to boiling temperature of an inert solvent to be used and reaction time may be in the range from several minutes to 48 hours, while depending on reaction scale and reaction temperature.

After completion of the reaction, desired compound may be isolated from the reaction mixture by a conventional method and the desired compound can be produced by purification using recrystallization or column chromatography, etc, if necessary.

An aniline derivative represented by the formula (II-1), as a raw material of the present reaction, can be produced in accordance with a production method disclosed in JP-A-11-302233, JP-A-2001-122836 or JP-A-2006-8675.

A pyrazolecarboxylic acid derivative represented by the formulas (III) or (IV) can be produced in accordance with several methods described in known literatures (for example, Aust. J. Chem., 1983, 36, 135-147, Synthesis, 1986, 753-755, JP-A-52-87168, JP-A-63-45264, JP-A-1-106866 and the like).

Production Method 2

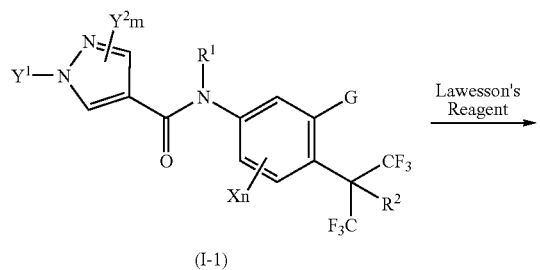

(I-1)

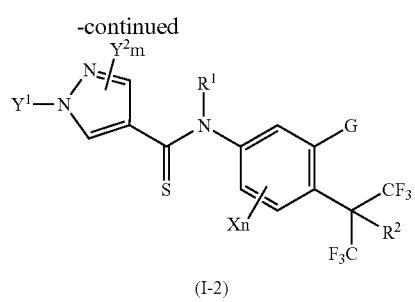

(I-2)

(wherein G, $R^1$, $R^2$, X, n, $Y^1$, $Y^2$ and m are as defined above).

Among substituted pyrazolecarboxanilide derivatives represented by the formula (I), a substituted pyrazolecarboxanilide derivative (I-2) wherein Z is S can be produced by reacting an anilide derivative represented by (I-1) with Lawesson's Reagent in accordance with a known method (Tetrahedron Lett., 21 (42), 4061 (1980)).

Production Method 3

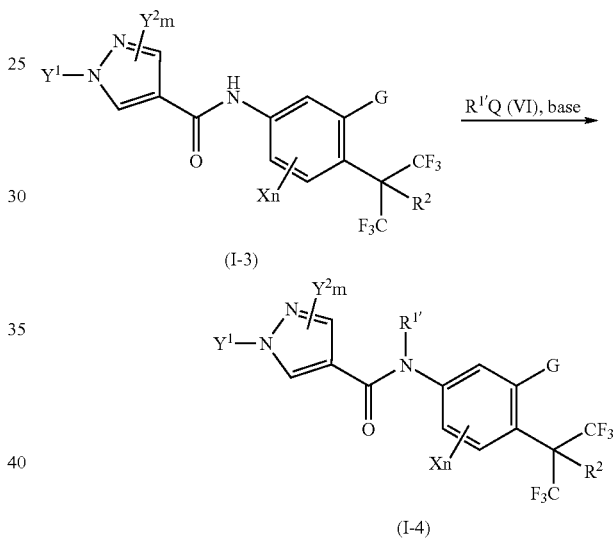

(wherein G, $R^2$, X, n, $Y^1$, $Y^2$, m and Q are as defined above and $R^{1'}$ is as defined above except a hydrogen atom).

Among substituted pyrazolecarboxanilide derivatives represented by the formula (I), a substituted pyrazolecarboxanilide derivative (I-4) wherein $R^1$ is other than a hydrogen atom can be produced by reacting an amide derivative represented by the formula (I-3) with a halide derivative or an ester derivative represented by the formula (VI), in the presence or absence of a base, in an inert solvent.

As an example of a base to be used in the present reaction includes metal hydroxides such as sodium hydroxide, potassium hydroxide and the like; carbonates such as sodium carbonate, potassium carbonate, sodium hydrogen carbonate and the like; metal hydrides such as lithium hydride, sodium hydride, potassium hydride and the like; metal alcoholates such as sodium methoxide, sodium ethoxide, potassium tert-butoxide and the like; alkyl metals such as n-butyl lithium, sec-butyl lithium, tert-butyl lithium and the like. The amount of the base to be used may be selected, as appropriate, in the range from equivalent to excess amount relative to an amide derivative represented by the formula (I-3).

An example of an inert solvent to be used in the present reaction, which may be any one as long as it does not significantly inhibit progress of the present reaction, includes aromatic hydrocarbons such as benzene, toluene, xylene and the like; alcohols such as methanol, ethanol and the like; straight chain or cyclic ethers such as diethyl ether, 1,2-dimethoxyethane, dioxane, tetrahydrofuran and the like; amides such as dimethylformamide, dimethylacetamide and the like; dimethylsulfoxide; 1,3-dimethyl-2-imidazolidinone and the like. These inert solvents can be used alone or in combination of two or more kinds.

Reaction temperature may be in the range from −70° C. to boiling temperature of an inert solvent to be used and reaction time may be in the range from several minutes to 50 hours, while depending on reaction scale and reaction temperature.

After completion of the reaction, desired compound may be isolated from the reaction mixture by a conventional method and the desired compound can be produced by purification using recrystallization or column chromatography, etc, if necessary.

Production Method 4

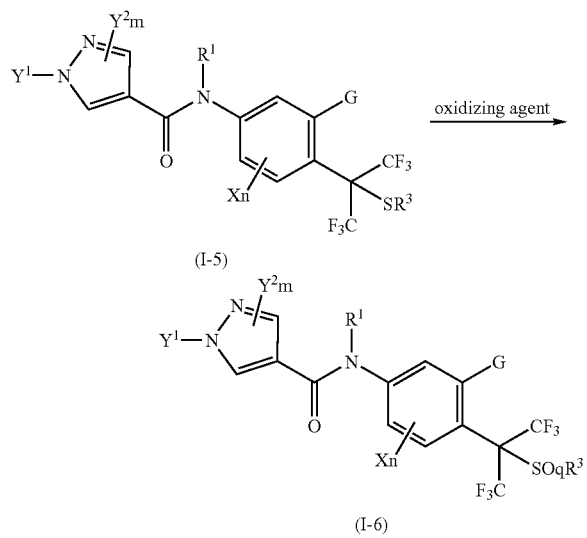

(wherein G, $R^1$, $R^3$, X, n, $Y^1$, $Y^2$ and m are as defined above, and q is 1 or 2).

A substituted pyrazolecarboxanilide derivatives represented by the formula (I-6) can be produced by reacting a sulfide derivative represented by the formula (I-5) which can be produced in Production method 1 with an oxidizing agent in the presence of an inert solvent An example of an inert solvent to be used in the present reaction includes halogenated hydrocarbons such as methylene chloride, chloroform and the like; aromatic hydrocarbons such as toluene, xylene and the like; halogenated aromatic hydrocarbons such as fluorobenzene, chlorobenzene, dichlorobenzene and the like; acids such as acetic acid and the like; alcohols such as methanol, ethanol, propanol and the like.

An example of an oxidizing agent includes m-peroxychlorobenzoic acid, peracetic acid, potassium metaperiodate, potassium hydrogen persulphate (Oxone), hydrogen peroxide and the like. The amount of the oxidizing agent to be used may be selected, as appropriate, in the range of 0.5 to 3 equivalents relative to a sulfide derivative represented by the formula (I-5).

Reaction temperature may be in the range from −50° C. to boiling temperature of an inert solvent to be used and reaction time may be in the range from several minutes to 24 hours, while depending on reaction scale and reaction temperature.

After completion of the reaction, desired compound may be isolated from the reaction mixture by a conventional method and the desired compound can be produced by purification using recrystallization or column chromatography, etc, if necessary.

Typical compounds of substituted pyrazolecarboxanilide derivatives represented by the formula (I) are exemplified in Table 1 and Table 2, and typical compounds of substituted aniline derivatives represented by the formula (II) are exemplified in Table 3, and an substituted pyrazolecarboxylic acid derivative represented by the formula (IV) is exemplified in Table 4, however, the present invention should not be construed as limiting to these.

In "property" column of Table 1 and Table 2, melting point (° C.) or refractive index ($n_D$(° C.)) is shown and for compounds described as amorphous or paste, $^1$H-NMR data thereof were shown in Table 5. In the Tables, "n-" is normal, and "i-" is iso, "t-" is tertiary, "c-" is cyclo, "Me" is a methyl group, "Et" is an ethyl group, "Pr" is a propyl group, "Bu" is a butyl group, "Pen" is a pentyl group, "Hex" is a hexyl group, "Ph" is a phenyl group, "Bn" is a benzyl group, "Ac" is an acetyl group and "Pyr" is a pyrazinyl group.

TABLE 1

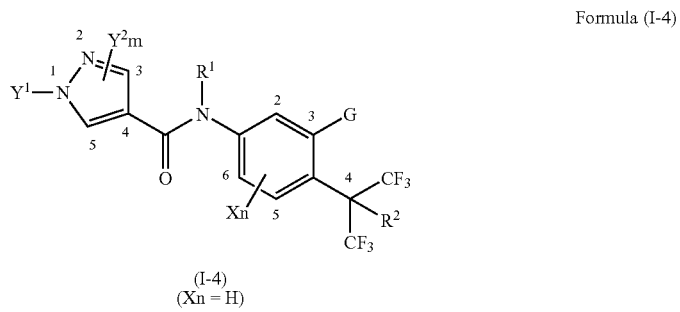

Formula (I-4)

(I-4)
(Xn = H)

| No. | G | $Y^1$ | $Y^2_m$ | $R^1$ | $R^2$ | Property |
|---|---|---|---|---|---|---|
| 1-1 | Et | Me | 3,5-Me$_2$ | H | H | 72-75 |
| 1-2 | Et | Me | 3,5-Me$_2$ | Ac | H | |
| 1-3 | Et | Me | 3,5-Me$_2$ | H | OMe | 129-131 |
| 1-4 | Et | Me | 3,5-Me$_2$ | Ac | OMe | 1.5028(25.4) |
| 1-5 | Et | Me | 3,5-Me$_2$ | COEt | OMe | |
| 1-6 | Et | Me | 3,5-Me$_2$ | CO-c-Pr | OMe | 118.8-121.6 |

TABLE 1-continued

Formula (I-4)

$$\text{(I-4)}$$
$$(Xn = H)$$

| No. | G | Y$^1$ | Y$^2_m$ | R$^1$ | R$^2$ | Property |
|---|---|---|---|---|---|---|
| 1-7 | Et | Me | 3,5-Me$_2$ | CH$_2$OMe | OMe | |
| 1-8 | Et | Me | 3,5-Me$_2$ | CH$_2$OEt | OMe | 1.4889(24.2) |
| 1-9 | Et | Me | 3,5-Me$_2$ | COOMe | OMe | |
| 1-10 | Et | Me | 3,5-Me$_2$ | COOEt | OMe | 77.2-79.2 |
| 1-11 | Et | Me | 3,5-Me$_2$ | COO-n-Pr | OMe | |
| 1-12 | Et | Me | 3,5-Me$_2$ | COO-i-Bu | OMe | 1.4895(25.4) |
| 1-13 | Et | Me | 3,5-Me$_2$ | H | OEt | 110-113 |
| 1-14 | Et | Me | 3,5-Me$_2$ | Ac | OEt | |
| 1-15 | Et | Me | 3,5-Me$_2$ | COEt | OEt | 90-91 |
| 1-16 | Et | Me | 3,5-Me$_2$ | CO-c-Pr | OEt | 119-120 |
| 1-17 | Et | Me | 3,5-Me$_2$ | CH$_2$OMe | OEt | |
| 1-18 | Et | Me | 3,5-Me$_2$ | CH$_2$OEt | OEt | |
| 1-19 | Et | Me | 3,5-Me$_2$ | COOMe | OEt | |
| 1-20 | Et | Me | 3,5-Me$_2$ | COOEt | OEt | |
| 1-21 | Et | Me | 3,5-Me$_2$ | COO-n-Pr | OEt | |
| 1-22 | Et | Me | 3,5-Me$_2$ | COO-i-Bu | OEt | |
| 1-23 | Et | Me | 3-CF$_3$-5-Me | H | H | 1.4768(21.8) |
| 1-24 | Et | Me | 3-CF$_3$-5-Me | Ac | H | 132-134 |
| 1-25 | Et | Me | 3-CF$_3$-5-Me | H | OMe | 57-60 |
| 1-26 | Et | Me | 3-CF$_3$-5-Me | Ac | OMe | 1.4736(24.6) |
| 1-27 | Et | Me | 3-CF$_3$-5-Me | COEt | OMe | 134-135 |
| 1-28 | Et | Me | 3-CF$_3$-5-Me | CO-c-Pr | OMe | 1.4830(26.2) |
| 1-29 | Et | Me | 3-CF$_3$-5-Me | CH$_2$OMe | OMe | |
| 1-30 | Et | Me | 3-CF$_3$-5-Me | CH$_2$OEt | OMe | |
| 1-31 | Et | Me | 3-CF$_3$-5-Me | COOMe | OMe | 128-130 |
| 1-32 | Et | Me | 3-CF$_3$-5-Me | COOEt | OMe | 1.4697(25.9) |
| 1-33 | Et | Me | 3-CF$_3$-5-Me | COO-n-Pr | OMe | |
| 1-34 | Et | Me | 3-CF$_3$-5-Me | COO-i-Bu | OMe | 1.4681(26.2) |
| 1-35 | Et | Me | 3-CF$_3$-5-Me | H | OEt | 142-145 |
| 1-36 | Et | Me | 3-CF$_3$-5-Me | Ac | OEt | 1.4720(24.5) |
| 1-37 | Et | Me | 3-CF$_3$-5-Me | COEt | OEt | 1.4710(26.9) |
| 1-38 | Et | Me | 3-CF$_3$-5-Me | CO-c-Pr | OEt | |
| 1-39 | Et | Me | 3-CF$_3$-5-Me | CH$_2$OMe | OEt | |
| 1-40 | Et | Me | 3-CF$_3$-5-Me | CH$_2$OEt | OEt | |
| 1-41 | Et | Me | 3-CF$_3$-5-Me | COOMe | OEt | |
| 1-42 | Et | Me | 3-CF$_3$-5-Me | COOEt | OEt | |
| 1-43 | Et | Me | 3-CF$_3$-5-Me | COO-n-Pr | OEt | |
| 1-44 | Et | Me | 3-CF$_3$-5-Me | COO-i-Bu | OEt | |
| 1-45 | n-Pr | Me | 3,5-Me$_2$ | H | H | 167-168 |
| 1-46 | n-Pr | Me | 3,5-Me$_2$ | Ac | H | |
| 1-47 | n-Pr | Me | 3,5-Me$_2$ | H | OMe | 184-185 |
| 1-48 | n-Pr | Me | 3,5-Me$_2$ | Ac | OMe | 1.4953(25.0) |
| 1-49 | n-Pr | Me | 3,5-Me$_2$ | COEt | OMe | 1.4982(34.2) |
| 1-50 | n-Pr | Me | 3,5-Me$_2$ | CO-c-Pr | OMe | |
| 1-51 | n-Pr | Me | 3,5-Me$_2$ | CH$_2$OMe | OMe | 1.4979(22.1) |
| 1-52 | n-Pr | Me | 3,5-Me$_2$ | CH$_2$OEt | OMe | 1.4942(22.7) |
| 1-53 | n-Pr | Me | 3,5-Me$_2$ | COOMe | OMe | 1.4980(22.7) |
| 1-54 | n-Pr | Me | 3,5-Me$_2$ | COOEt | OMe | 1.4952(23.0) |
| 1-55 | n-Pr | Me | 3,5-Me$_2$ | COO-n-Pr | OMe | |
| 1-56 | n-Pr | Me | 3,5-Me$_2$ | COO-i-Bu | OMe | 1.4933(23.2) |
| 1-57 | n-Pr | Me | 3,5-Me$_2$ | H | OEt | 178-179 |
| 1-58 | n-Pr | Me | 3,5-Me$_2$ | Ac | OEt | |
| 1-59 | n-Pr | Me | 3,5-Me$_2$ | COEt | OEt | 1.4980(22.7) |
| 1-60 | n-Pr | Me | 3,5-Me$_2$ | CO-c-Pr | OEt | |
| 1-61 | n-Pr | Me | 3,5-Me$_2$ | CH$_2$OMe | OEt | |
| 1-62 | n-Pr | Me | 3,5-Me$_2$ | CH$_2$OEt | OEt | |
| 1-63 | n-Pr | Me | 3,5-Me$_2$ | COOMe | OEt | |
| 1-64 | n-Pr | Me | 3,5-Me$_2$ | COOEt | OEt | |
| 1-65 | n-Pr | Me | 3,5-Me$_2$ | COO-n-Pr | OEt | |
| 1-66 | n-Pr | Me | 3,5-Me$_2$ | COO-i-Bu | OEt | |
| 1-67 | n-Pr | Me | 3-CF$_3$-5-Me | H | H | 131-133 |
| 1-68 | n-Pr | Me | 3-CF$_3$-5-Me | Ac | H | |

TABLE 1-continued

Formula (I-4)

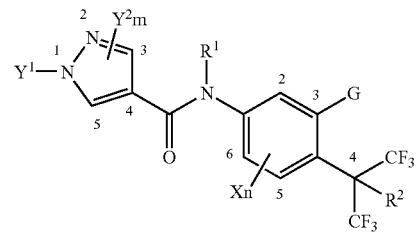

(I-4)
(Xn = H)

| No. | G | Y¹ | Y²_m | R¹ | R² | Property |
|---|---|---|---|---|---|---|
| 1-69 | n-Pr | Me | 3-CF₃-5-Me | H | OMe | 124 |
| 1-70 | n-Pr | Me | 3-CF₃-5-Me | Ac | OMe | 1.4711(25.6) |
| 1-71 | n-Pr | Me | 3-CF₃-5-Me | COEt | OMe | 1.4700(26.8) |
| 1-72 | n-Pr | Me | 3-CF₃-5-Me | CO-c-Pr | OMe | 1.4795(25.5) |
| 1-73 | n-Pr | Me | 3-CF₃-5-Me | CH₂OMe | OMe | |
| 1-74 | n-Pr | Me | 3-CF₃-5-Me | CH₂OEt | OMe | 1.4658(26.9) |
| 1-75 | n-Pr | Me | 3-CF₃-5-Me | COOMe | OMe | 126-128 |
| 1-76 | n-Pr | Me | 3-CF₃-5-Me | COOEt | OMe | 1.4671(26.9) |
| 1-77 | n-Pr | Me | 3-CF₃-5-Me | COO-n-Pr | OMe | |
| 1-78 | n-Pr | Me | 3-CF₃-5-Me | COO-i-Bu | OMe | 1.4645(26.9) |
| 1-79 | n-Pr | Me | 3-CF₃-5-Me | H | OEt | |
| 1-80 | n-Pr | Me | 3-CF₃-5-Me | Ac | OEt | |
| 1-81 | n-Pr | Me | 3-CF₃-5-Me | COEt | OEt | |
| 1-82 | n-Pr | Me | 3-CF₃-5-Me | CO-c-Pr | OEt | |
| 1-83 | n-Pr | Me | 3-CF₃-5-Me | CH₂OMe | OEt | |
| 1-84 | n-Pr | Me | 3-CF₃-5-Me | CH₂OEt | OEt | |
| 1-85 | n-Pr | Me | 3-CF₃-5-Me | COOMe | OEt | |
| 1-86 | n-Pr | Me | 3-CF₃-5-Me | COOEt | OEt | |
| 1-87 | n-Pr | Me | 3-CF₃-5-Me | COO-n-Pr | OEt | |
| 1-88 | n-Pr | Me | 3-CF₃-5-Me | COO-i-Bu | OEt | |
| 1-89 | n-Bu | Me | 3,5-Me₂ | H | H | 150-151.5 |
| 1-90 | n-Bu | Me | 3,5-Me₂ | Ac | H | |
| 1-91 | n-Bu | Me | 3,5-Me₂ | H | OMe | 196-197 |
| 1-92 | n-Bu | Me | 3,5-Me₂ | Ac | OMe | |
| 1-93 | n-Bu | Me | 3,5-Me₂ | H | OEt | |
| 1-94 | n-Bu | Me | 3,5-Me₂ | Ac | OEt | |
| 1-95 | n-Bu | Me | 3-CF₃-5-Me | H | H | 83-85 |
| 1-96 | n-Bu | Me | 3-CF₃-5-Me | Ac | H | |
| 1-97 | n-Bu | Me | 3-CF₃-5-Me | H | OMe | |
| 1-98 | n-Bu | Me | 3-CF₃-5-Me | Ac | OMe | |
| 1-99 | n-Bu | Me | 3-CF₃-5-Me | H | OEt | |
| 1-100 | n-Bu | Me | 3-CF₃-5-Me | Ac | OEt | |
| 1-101 | i-Bu | Me | 3-Me | H | H | 141-144 |
| 1-102 | i-Bu | Me | 3-Me | Et | OMe | 1.4916(23.7) |
| 1-103 | i-Bu | Me | 3-Me | Ac | OMe | 1.4961(26.4) |
| 1-104 | i-Bu | Me | 3-Me | COEt | OMe | 1.4973(26.2) |
| 1-105 | i-Bu | Me | 3-Me | CO-c-Pr | OMe | 1.5014(25.5) |
| 1-106 | i-Bu | Me | 3-Me | CO(4-Me-Ph) | OMe | amorphous |
| 1-107 | i-Bu | Me | 3-Me | CO(4-NO₂-Ph) | OMe | amorphous |
| 1-108 | i-Bu | Me | 3-Me | COOMe | OMe | 95.5-97.8 |
| 1-109 | i-Bu | Me | 3-Me | COOEt | OMe | 84.6-86.2 |
| 1-110 | i-Bu | Me | 3-Me | COO-n-Pr | OMe | 86.7-88.4 |
| 1-111 | i-Bu | Me | 3-Me | COO-i-Bu | OMe | 91.8-94.0 |
| 1-112 | i-Bu | Me | 3-Me | CH₂OMe | OMe | 1.4919(24.0) |
| 1-113 | i-Bu | Me | 3-Me | CH₂OEt | OMe | 1.4920(24.4) |
| 1-114 | i-Bu | Me | 3-CF₃ | H | H | 172-174 |
| 1-115 | i-Bu | Me | 3-CF₃ | Ac | H | |
| 1-116 | i-Bu | Me | 3-CF₃ | H | OMe | amorphous |
| 1-117 | i-Bu | Me | 3-CF₃ | Ac | OMe | |
| 1-118 | i-Bu | Me | 3-CF₃ | H | OEt | |
| 1-119 | i-Bu | Me | 3-CF₃ | Ac | OEt | |
| 1-120 | i-Bu | Et | 3-CF₃ | H | H | 175-176 |
| 1-121 | i-Bu | Me | 5-CF₃ | H | H | 155-156 |
| 1-122 | i-Bu | Me | 5-SMe | H | H | 107-110 |
| 1-123 | i-Bu | Me | 3,5-Me₂ | H | H | 148-151 |
| 1-124 | i-Bu | Me | 3,5-Me₂ | SO₂(4-F-Ph) | H | amorphous |
| 1-125 | i-Bu | Me | 3,5-Me₂ | Ac | H | 1.5021(22.5) |
| 1-126 | i-Bu | Me | 3,5-Me₂ | COEt | H | 143.1-148.8 |
| 1-127 | i-Bu | Me | 3,5-Me₂ | COPh | H | 51.3-65.3 |
| 1-128 | i-Bu | Me | 3,5-Me₂ | COCH₂CMe₃ | H | 1.4859(22.0) |
| 1-129 | i-Bu | Me | 3,5-Me₂ | CH₂OEt | H | 1.4882(23.8) |
| 1-130 | i-Bu | Me | 3,5-Me₂ | CH₂O(CH₂)₇Me | H | 1.4854(22.0) |

TABLE 1-continued

Formula (I-4)

(I-4)
(Xn = H)

| No. | G | Y¹ | Y²$_m$ | R¹ | R² | Property |
|---|---|---|---|---|---|---|
| 1-131 | i-Bu | Me | 3,5-Me$_2$ | CH$_2$O(CH$_2$)$_2$OMe | H | 1.4889(21.9) |
| 1-132 | i-Bu | Me | 3,5-Me$_2$ | CH$_2$OBn | H | 1.5212(21.9) |
| 1-133 | i-Bu | Me | 3,5-Me$_2$ | COOCH$_2$Cl | H | 121.1-124.8 |
| 1-134 | i-Bu | Me | 3,5-Me$_2$ | COOCH$_2$CCl$_3$ | H | 143.1-145.6 |
| 1-135 | i-Bu | Me | 3,5-Me$_2$ | COO(CH$_2$)$_2$CH$_2$Cl | H | 117.1-121.4 |
| 1-136 | i-Bu | Me | 3,5-Me$_2$ | COO-i-Bu | H | 122.2-138.0 |
| 1-137 | i-Bu | Me | 3,5-Me$_2$ | COO-t-Bu | H | 39.2 |
| 1-138 | i-Bu | Me | 3,5-Me$_2$ | COO(CH$_2$)$_2$OMe | H | 1.4750(23.5) |
| 1-139 | i-Bu | Me | 3,5-Me$_2$ | COO(CH$_2$)$_{15}$Me | H | 90.5-92.1 |
| 1-140 | i-Bu | Me | 3,5-Me$_2$ | Ac | OMe | 1.5016(23.3) |
| 1-141 | i-Bu | Me | 3,5-Me$_2$ | COEt | OMe | 1.4981(23.5) |
| 1-142 | i-Bu | Me | 3,5-Me$_2$ | CO-i-Pr | OMe | 82.5-83 |
| 1-143 | i-Bu | Me | 3,5-Me$_2$ | COPh | OMe | 1.5219(23.7) |
| 1-144 | i-Bu | Me | 3,5-Me$_2$ | CH$_2$OMe | OMe | 1.4944(23.1) |
| 1-145 | i-Bu | Me | 3,5-Me$_2$ | CH$_2$OEt | OMe | 1.4892(22.2) |
| 1-146 | i-Bu | Me | 3,5-Me$_2$ | CH$_2$O(CH$_2$)$_2$OMe | OMe | 1.4885(25.1) |
| 1-147 | i-Bu | Me | 3,5-Me$_2$ | COOMe | OMe | 1.4926(23.2) |
| 1-148 | i-Bu | Me | 3,5-Me$_2$ | COOEt | OMe | 1.4894(23.2) |
| 1-149 | i-Bu | Me | 3,5-Me$_2$ | COOCH$_2$Cl | OMe | 1.4941(21.5) |
| 1-150 | i-Bu | Me | 3,5-Me$_2$ | COO-n-Pr | OMe | 1.4928(22.2) |
| 1-151 | i-Bu | Me | 3,5-Me$_2$ | COO-i-Pr | OMe | 1.4884(23.0) |
| 1-152 | i-Bu | Me | 3,5-Me$_2$ | COO-i-Bu | OMe | 1.4829(22.3) |
| 1-153 | i-Bu | Me | 3,5-Me$_2$ | COOCH$_2$CMe$_3$ | OMe | 1.4864(23.0) |
| 1-154 | i-Bu | Me | 3,5-Me$_2$ | COO(CH$_2$)$_2$OMe | OMe | 1.4959(23.0) |
| 1-155 | i-Bu | Me | 3,5-Me$_2$ | H | OMe | 189-190 |
| 1-156 | i-Bu | Me | 3,5-Me$_2$ | Et | OMe | amorphous |
| 1-157 | i-Bu | Me | 3,5-Me$_2$ | CH$_2$CCl$_3$ | OMe | 1.4939(22.2) |
| 1-158 | i-Bu | Me | 3,5-Me$_2$ | Ac | OEt | 1.4940(26.4) |
| 1-159 | i-Bu | Me | 3,5-Me$_2$ | COEt | OEt | 1.4921(26.5) |
| 1-160 | i-Bu | Me | 3,5-Me$_2$ | CO-i-Pr | OEt | paste |
| 1-161 | i-Bu | Me | 3,5-Me$_2$ | COPh | OEt | |
| 1-162 | i-Bu | Me | 3,5-Me$_2$ | CH$_2$OMe | OEt | |
| 1-163 | i-Bu | Me | 3,5-Me$_2$ | CH$_2$OEt | OEt | |
| 1-164 | i-Bu | Me | 3,5-Me$_2$ | CH$_2$O(CH$_2$)$_2$OMe | OEt | |
| 1-165 | i-Bu | Me | 3,5-Me$_2$ | COOMe | OEt | |
| 1-166 | i-Bu | Me | 3,5-Me$_2$ | COOEt | OEt | |
| 1-167 | i-Bu | Me | 3,5-Me$_2$ | COOCH$_2$Cl | OEt | |
| 1-168 | i-Bu | Me | 3,5-Me$_2$ | COO-n-Pr | OEt | |
| 1-169 | i-Bu | Me | 3,5-Me$_2$ | COO-i-Pr | OEt | |
| 1-170 | i-Bu | Me | 3,5-Me$_2$ | COO-i-Bu | OEt | |
| 1-171 | i-Bu | Me | 3,5-Me$_2$ | COOCH$_2$CMe$_3$ | OEt | |
| 1-172 | i-Bu | Me | 3,5-Me$_2$ | COO(CH$_2$)$_2$OMe | OEt | |
| 1-173 | i-Bu | Me | 3,5-Me$_2$ | H | OEt | 165-166 |
| 1-174 | i-Bu | Me | 3,5-Me$_2$ | Et | OEt | |
| 1-175 | i-Bu | Me | 3,5-Me$_2$ | CH$_2$CCl$_3$ | OEt | |
| 1-176 | i-Bu | Et | 3,5-Me$_2$ | H | H | 127-128 |
| 1-177 | i-Bu | Me | 3,5-Me$_2$ | H | F | 136.5-137.5 |
| 1-178 | i-Bu | Me | 3,5-Me$_2$ | Et | H | 1.4904(25.7) |
| 1-179 | i-Bu | Me | 3-Me-5-F | H | H | 169.5-171 |
| 1-180 | i-Bu | Me | 3-Me-5-F | H | OMe | 135-137 |
| 1-181 | i-Bu | Me | 3-Me-5-F | Et | OMe | 1.4825(26.0) |
| 1-182 | i-Bu | Me | 3-Me-S-F | Ac | OMe | 86.4 |
| 1-183 | i-Bu | Me | 3-Me-5-F | COPh | OMe | 124.1-130.8 |
| 1-184 | i-Bu | Me | 3-Me-5-F | COOMe | OMe | 64.5-80.5 |
| 1-185 | i-Bu | Me | 3-Me-5-F | COO-i-Bu | OMe | 1.4789(23.7) |
| 1-186 | i-Bu | Me | 3-Me-5-F | COO(CH$_2$)$_2$OMe | OMe | 1.4857(22.3) |
| 1-187 | i-Bu | Me | 3-Me-5-F | CH$_2$OEt | OMe | 1.4804(23.8) |
| 1-188 | i-Bu | Me | 3-Me-5-Cl | H | H | 160-161 |
| 1-189 | i-Bu | Me | 3-Me-5-Cl | H | OMe | 144-146 |
| 1-190 | i-Bu | Me | 3-Me-5-Cl | Me | OMe | 1.4919(25.6) |
| 1-191 | i-Bu | Me | 3-Me-5-Cl | Et | OMe | 1.4938(26.0) |
| 1-192 | i-Bu | Me | 3-Me-5-Cl | CH$_2$OMe | OMe | 1.4961(26.0) |

TABLE 1-continued

Formula (I-4)

$$\text{(I-4)}$$
$$(Xn = H)$$

| No. | G | Y¹ | Y²ₘ | R¹ | R² | Property |
|---|---|---|---|---|---|---|
| 1-193 | i-Bu | Me | 3-Me-5-Cl | CH₂OEt | OMe | 1.4932(25.6) |
| 1-194 | i-Bu | Me | 3-Me-5-Cl | COOMe | OMe | 1.4883(25.6) |
| 1-195 | i-Bu | Me | 3-Me-5-Cl | COOEt | OMe | 1.4915(26.0) |
| 1-196 | i-Bu | Me | 3-Me-5-Cl | COO-i-Bu | OMe | 1.4850(25.6) |
| 1-197 | i-Bu | Me | 3-Me-5-Cl | COO(CH₂)₂OMe | OMe | 1.4946(26.0) |
| 1-198 | i-Bu | Me | 3-Me-5-Cl | Ac | OMe | 102.6-102.8 |
| 1-199 | i-Bu | Me | 3-Me-5-Cl | COEt | OMe | 101.8-104.2 |
| 1-200 | i-Bu | Me | 3-Me-5-Cl | COPh | OMe | 1.5210(26.0) |
| 1-201 | i-Bu | Et | 3-Me-5-Cl | H | H | 104.5-106 |
| 1-202 | i-Bu | Me | 3-Me-5-I | H | H | 152-153 |
| 1-203 | i-Bu | Me | 3-Me-5-CF₃ | H | OMe | 88-89 |
| 1-204 | i-Bu | Me | 3-Me-5-CF₃ | Ac | OMe | 1.4710(25.7) |
| 1-205 | i-Bu | Me | 3-Me-5-CF₃ | COOMe | OMe | 1.4672(25.7) |
| 1-206 | i-Bu | Me | 3-Me-5-CF₃ | CH₂OEt | OMe | 1.4652(25.7) |
| 1-207 | i-Bu | Me | 3-CF₃-5-Me | H | H | 1.4869(23.4) |
| 1-208 | i-Bu | Me | 3-CF₃-5-Me | Ac | H | 152-152.5 |
| 1-209 | i-Bu | Me | 3-CF₃-5-Me | COOMe | H | 148.5-150 |
| 1-210 | i-Bu | Me | 3-CF₃-5-Me | CH₂OEt | H | 1.4623(22.8) |
| 1-211 | i-Bu | Me | 3-CF₃-5-Me | H | OMe | 138-139 |
| 1-212 | i-Bu | Me | 3-CF₃-5-Me | COOMe | OMe | 1.4729(20.7) |
| 1-213 | i-Bu | Me | 3-CF₃-5-Me | COOEt | OMe | 1.4695(20.7) |
| 1-214 | i-Bu | Me | 3-CF₃-5-Me | COOCH₂CH=CH₂ | OMe | 1.4742(24.5) |
| 1-215 | i-Bu | Me | 3-CF₃-5-Me | COO(CH₂)₂Me | OMe | 1.4685(20.7) |
| 1-216 | i-Bu | Me | 3-CF₃-5-Me | COO(CH₂)₃Me | OMe | 1.4689(24.5) |
| 1-217 | i-Bu | Me | 3-CF₃-5-Me | COO-i-Bu | OMe | 1.4669(22.6) |
| 1-218 | i-Bu | Me | 3-CF₃-5-Me | COOPh | OMe | 50-55 |
| 1-219 | i-Bu | Me | 3-CF₃-5-Me | COO(CH₂)₂OMe | OMe | 1.4691(22.3) |
| 1-220 | i-Bu | Me | 3-CF₃-5-Me | COSMe | OMe | 1.4870(24.9) |
| 1-221 | i-Bu | Me | 3-CF₃-5-Me | COSEt | OMe | 1.4862(24.9) |
| 1-222 | i-Bu | Me | 3-CF₃-5-Me | CH₂OMe | OMe | 1.4669(22.4) |
| 1-223 | i-Bu | Me | 3-CF₃-5-Me | CH₂OEt | OMe | 108-110 |
| 1-224 | i-Bu | Me | 3-CF₃-5-Me | Ac | OMe | 1.4720(20.6) |
| 1-225 | i-Bu | Me | 3-CF₃-5-Me | CO-c-Pr | OMe | 1.4735(24.8) |
| 1-226 | i-Bu | Me | 3-CF₃-5-Me | H | OEt | |
| 1-227 | i-Bu | Me | 3-CF₃-5-Me | Ac | OEt | |
| 1-228 | i-Bu | Me | 3-CF₃-5-Cl | H | H | 136-137 |
| 1-229 | i-Bu | Me | 3-CF₃-5-Cl | Ac | H | |
| 1-230 | i-Bu | Me | 3-CF₃-5-Cl | H | OMe | 130-132 |
| 1-231 | i-Bu | Me | 3-CF₃-5-Cl | Ac | OMe | |
| 1-232 | i-Bu | Me | 3-CF₃-5-Cl | H | OEt | |
| 1-233 | i-Bu | Me | 3-CF₃-5-Cl | Ac | OEt | |
| 1-234 | (CH₂)₄Me | Me | 3,5-Me₂ | H | H | 128-130 |
| 1-235 | (CH₂)₄Me | Me | 3,5-Me₂ | Ac | H | |
| 1-236 | (CH₂)₄Me | Me | 3,5-Me₂ | H | OMe | |
| 1-237 | (CH₂)₄Me | Me | 3,5-Me₂ | Ac | OMe | |
| 1-238 | (CH₂)₄Me | Me | 3,5-Me₂ | H | OEt | |
| 1-239 | (CH₂)₄Me | Me | 3,5-Me₂ | Ac | OEt | |
| 1-240 | (CH₂)₄Me | Me | 3-CF₃-5-Me | H | H | |
| 1-241 | (CH₂)₄Me | Me | 3-CF₃-5-Me | Ac | H | |
| 1-242 | (CH₂)₄Me | Me | 3-CF₃-5-Me | H | OMe | |
| 1-243 | (CH₂)₄Me | Me | 3-CF₃-5-Me | Ac | OMe | |
| 1-244 | (CH₂)₄Me | Me | 3-CF₃-5-Me | H | OEt | |
| 1-245 | (CH₂)₄Me | Me | 3-CF₃-5-Me | Ac | OEt | |
| 1-246 | CH₂CMe₃ | Me | 3,5-Me₂ | H | H | 174-176 |
| 1-247 | CH₂CMe₃ | Me | 3,5-Me₂ | Ac | H | |
| 1-248 | CH₂CMe₃ | Me | 3,5-Me₂ | H | OMe | |
| 1-249 | CH₂CMe₃ | Me | 3,5-Me₂ | Ac | OMe | |
| 1-250 | CH₂CMe₃ | Me | 3,5-Me₂ | H | OEt | |
| 1-251 | CH₂CMe₃ | Me | 3,5-Me₂ | Ac | OEt | |
| 1-252 | CH₂CMe₃ | Me | 3-CF₃-5-Me | H | H | |
| 1-253 | CH₂CMe₃ | Me | 3-CF₃-5-Me | Ac | H | |
| 1-254 | CH₂CMe₃ | Me | 3-CF₃-5-Me | H | OMe | |

TABLE 1-continued

Formula (I-4)

(I-4)
(Xn = H)

| No. | G | Y¹ | Y²$_m$ | R¹ | R² | Property |
|---|---|---|---|---|---|---|
| 1-255 | CH$_2$CMe$_3$ | Me | 3-CF$_3$-5-Me | Ac | OMe | |
| 1-256 | CH$_2$CMe$_3$ | Me | 3-CF$_3$-5-Me | H | OEt | |
| 1-257 | CH$_2$CMe$_3$ | Me | 3-CF$_3$-5-Me | Ac | OEt | |
| 1-258 | CH$_2$CH(Me)Et | Me | 3,5-Me$_2$ | H | H | 67-70 |
| 1-259 | CH$_2$CH(Me)Et | Me | 3,5-Me$_2$ | Ac | H | |
| 1-260 | CH$_2$CH(Me)Et | Me | 3,5-Me$_2$ | H | OMe | 158-160 |
| 1-261 | CH$_2$CH(Me)Et | Me | 3,5-Me$_2$ | Ac | OMe | |
| 1-262 | CH$_2$CH(Me)Et | Me | 3,5-Me$_2$ | H | OEt | |
| 1-263 | CH$_2$CH(Me)Et | Me | 3,5-Me$_2$ | Ac | OEt | |
| 1-264 | CH$_2$CH(Me)Et | Me | 3-CF$_3$-5-Me | H | H | |
| 1-265 | CH$_2$CH(Me)Et | Me | 3-CF$_3$-5-Me | Ac | H | |
| 1-266 | CH$_2$CH(Me)Et | Me | 3-CF$_3$-5-Me | H | OMe | 143-144 |
| 1-267 | CH$_2$CH(Me)Et | Me | 3-CF$_3$-5-Me | Ac | OMe | |
| 1-268 | CH$_2$CH(Me)Et | Me | 3-CF$_3$-5-Me | H | OEt | |
| 1-269 | CH$_2$CH(Me)Et | Me | 3-CF$_3$-5-Me | Ac | OEt | |
| 1-270 | CH$_2$CHEt$_2$ | Me | 3,5-Me$_2$ | H | H | 67-70 |
| 1-271 | CH$_2$CHEt$_2$ | Me | 3,5-Me$_2$ | Ac | H | |
| 1-272 | CH$_2$CHEt$_2$ | Me | 3,5-Me$_2$ | H | OMe | |
| 1-273 | CH$_2$CHEt$_2$ | Me | 3,5-Me$_2$ | Ac | OMe | |
| 1-274 | CH$_2$CHEt$_2$ | Me | 3,5-Me$_2$ | H | OEt | |
| 1-275 | CH$_2$CHEt$_2$ | Me | 3,5-Me$_2$ | Ac | OEt | |
| 1-276 | CH$_2$CHEt$_2$ | Me | 3-CF$_3$-5-Me | H | H | |
| 1-277 | CH$_2$CHEt$_2$ | Me | 3-CF$_3$-5-Me | Ac | H | |
| 1-278 | CH$_2$CHEt$_2$ | Me | 3-CF$_3$-5-Me | H | OMe | |
| 1-279 | CH$_2$CHEt$_2$ | Me | 3-CF$_3$-5-Me | Ac | OMe | |
| 1-280 | CH$_2$CHEt$_2$ | Me | 3-CF$_3$-5-Me | H | OEt | |
| 1-281 | CH$_2$CHEt$_2$ | Me | 3-CF$_3$-5-Me | Ac | OEt | |
| 1-282 | (CH$_2$)$_2$CHMe$_2$ | Me | 3,5-Me$_2$ | H | H | 152-153 |
| 1-283 | (CH$_2$)$_2$CHMe$_2$ | Me | 3,5-Me$_2$ | Ac | H | |
| 1-284 | (CH$_2$)$_2$CHMe$_2$ | Me | 3,5-Me$_2$ | H | OMe | 166-167 |
| 1-285 | (CH$_2$)$_2$CHMe$_2$ | Me | 3,5-Me$_2$ | Ac | OMe | 1.4925(21.8) |
| 1-286 | (CH$_2$)$_2$CHMe$_2$ | Me | 3,5-Me$_2$ | H | OEt | |
| 1-287 | (CH$_2$)$_2$CHMe$_2$ | Me | 3,5-Me$_2$ | Ac | OEt | |
| 1-288 | (CH$_2$)$_2$CHMe$_2$ | Me | 3-CF$_3$-5-Me | H | H | |
| 1-289 | (CH$_2$)$_2$CHMe$_2$ | Me | 3-CF$_3$-5-Me | Ac | H | |
| 1-290 | (CH$_2$)$_2$CHMe$_2$ | Me | 3-CF$_3$-5-Me | H | OMe | 138-140 |
| 1-291 | (CH$_2$)$_2$CHrMe$_2$ | Me | 3-CF$_3$-5-Me | Ac | OMe | |
| 1-292 | (CH$_2$)$_2$CHMe$_2$ | Me | 3-CF$_3$-5-Me | H | OEt | |
| 1-293 | (CH$_2$)$_2$CHMe$_2$ | Me | 3-CF$_3$-5-Me | Ac | OEt | |
| 1-294 | (CH$_2$)$_7$Me | Me | 3,5-Me$_2$ | H | H | 1.5052(23.3) |
| 1-295 | (CH$_2$)$_7$Me | Me | 3,5-Me$_2$ | Ac | H | |
| 1-296 | (CH$_2$)$_7$Me | Me | 3,5-Me$_2$ | H | OMe | |
| 1-297 | (CH$_2$)$_7$Me | Me | 3,5-Me$_2$ | Ac | OMe | |
| 1-298 | (CH$_2$)$_7$Me | Me | 3,5-Me$_2$ | H | OEt | |
| 1-299 | (CH$_2$)$_7$Me | Me | 3,5-Me$_2$ | Ac | OEt | |
| 1-300 | (CH$_2$)$_7$Me | Me | 3-CF$_3$-5-Me | H | H | |
| 1-301 | (CH$_2$)$_7$Me | Me | 3-CF$_3$-5-Me | Ac | H | |
| 1-302 | (CH$_2$)$_7$Me | Me | 3-CF$_3$-5-Me | H | OMe | |
| 1-303 | (CH$_2$)$_7$Me | Me | 3-CF$_3$-5-Me | Ac | OMe | |
| 1-304 | (CH$_2$)$_7$Me | Me | 3-CF$_3$-5-Me | H | OEt | |
| 1-305 | (CH$_2$)$_7$Me | Me | 3-CF$_3$-5-Me | Ac | OEt | |
| 1-306 | n-Pr | Me | 3-Me-5-CF$_3$ | H | H | 141-143 |
| 1-307 | n-Pr | Me | 3-Me-5-CF$_3$ | H | OMe | 152-153 |
| 1-308 | n-Pr | Me | 3-Me-5-CF$_3$ | Ac | OMe | 1.4688(25.6) |
| 1-309 | n-Pr | Me | 3-Me-5-CF$_3$ | Ac | H | 112-113 |
| 1-310 | i-Bu | Me | 3-CF$_3$-5-Me | CH$_2$OMe | H | 1.4690(25.9) |
| 1-311 | i-Bu | Me | 3-Me-5-F | COOCH$_2$CH$_2$Cl | OMe | 1.4966(24.7) |
| 1-312 | i-Bu | Me | 3,5-Me$_2$ | COOCH$_2$CH$_2$Cl | OMe | 1.5039(24.8) |
| 1-313 | i-Bu | Me | 3,5-Me$_2$ | COCH$_2$CMe$_3$ | OMe | 1.4914(24.8) |
| 1-314 | i-Bu | Me | 3,5-Me$_2$ | CO-c-Pr | OMe | 1.5061(24.9) |
| 1-315 | i-Bu | Me | 3-CF$_3$-5-Me | COEt | H | 171-173 |
| 1-316 | i-Bu | ClCH$_2$CH$_2$ | 3,5-Me$_2$ | H | OMe | 170-171 |

TABLE 1-continued

Formula (I-4)

(I-4)
(Xn = H)

| No. | G | Y¹ | Y²ₘ | R¹ | R² | Property |
|---|---|---|---|---|---|---|
| 1-317 | i-Bu | ClCH₂CH₂ | 3,5-Me₂ | Ac | OMe | 1.4955(24.8) |
| 1-318 | i-Bu | Me | 3,5-Me₂ | CO-n-Pr | OMe | 1.4943(24.8) |
| 1-319 | i-Bu | Me | 3,5-Me₂ | CO-t-Bu | OMe | 113-115 |
| 1-320 | i-Bu | Me | 3,5-Me₂ | CO(4-MeO-Ph) | OMe | 1.5198(25.3) |
| 1-321 | i-Bu | Me | 3,5-Me₂ | CO(4-Me-Ph) | OMe | 1.5139(25.0) |
| 1-322 | i-Bu | Me | 3,5-Me₂ | CO(4-Cl-Ph) | OMe | 51-64 |
| 1-323 | n-Pr | Me | 3-Me-5-CF₃ | COEt | OMe | 1.4705(26.8) |
| 1-324 | i-Bu | Me | 3,5-Me₂ | CO(3-Cl-Ph) | OMe | 1.5266(25.4) |
| 1-325 | i-Bu | Me | 3,5-Me₂ | CO(3-Me-Ph) | OMe | 1.5182(25.5) |
| 1-326 | i-Bu | Me | 3,5-Me₂ | CO(3-Me-OPh) | OMe | 1.5165(26.5) |
| 1-327 | i-Bu | Me | 3,5-Me₂ | CO(2-Me-Ph) | OMe | 88-128 |
| 1-328 | i-Bu | Me | 3,5-Me₂ | CO(2-Cl-Ph) | OMe | 121-122 |
| 1-329 | i-Bu | Me | 3,5-Me₂ | CO(2-MeO-Ph) | OMe | 57-83 |
| 1-330 | i-Bu | Me | 3,5-Me₂ | COCH=CH₂ | OMe | 1.5088(24.5) |
| 1-331 | i-Bu | Me | 3,5-Me₂ | COCHClMe | OMe | amorphous |
| 1-332 | i-Bu | Me | 3,5-Me₂ | CO(3-Me-2-Pyr) | OMe | 52-64 |
| 1-333 | i-Bu | Me | 3,5-Me₂ | SNEt₂ | OMe | |
| 1-334 | i-Bu | Me | 3-CF₃-5-Me | CO-i-Pr | H | 161-163 |
| 1-335 | Et | Me | 3-CF₃-5-Me | CO-i-Pr | OMe | 1.4680(26.4) |
| 1-336 | i-Bu | Me | 3,5-Me₂ | CO-t-Pen | OMe | 95-96 |
| 1-337 | i-Bu | Me | 3,5-Me₂ | COCH₂OMe | OMe | 1.4939(26.5) |
| 1-338 | i-Bu | Me | 3,5-Me₂ | CO(4-CF₃-Ph) | OMe | 54 |
| 1-339 | i-Bu | Me | 3,5-Me₂ | COCH₂Ph | OMe | |
| 1-340 | i-Bu | Me | 3,5-Me₂ | COCH=CMe₂ | OMe | 1.5091(26.5) |
| 1-341 | i-Bu | Me | 3,5-Me₂ | COCH=CHMe | OMe | 1.5082(26.5) |
| 1-342 | i-Bu | Me | 3,5-Me₂ | COCH₂CH₂COOEt | OMe | 100-101 |
| 1-343 | n-Pr | Me | 3-CF₃-5-Me | COOCH₂CH=CH₂ | OMe | 1.4728(27.0) |
| 1-344 | n-Pr | Me | 3-CF₃-5-Me | CO-t-Bu | OMe | 1.4715(26.9) |
| 1-345 | n-Pr | Me | 3-CF₃-5-Me | CO-n-Pr | OMe | 1.4660(26.8) |
| 1-346 | Et | Me | 3-CF₃-5-Me | COOCH₂CH₂OMe | OMe | 1.4695(26.2) |
| 1-347 | Et | Me | 3-CF₃-5-Me | CO-t-Bu | OMe | 1.4730(26.2) |
| 1-348 | i-Bu | Me | 3,5-Me₂ | COCMe₂CH₂Cl | OMe | 1.5062(26.7) |
| 1-349 | i-Bu | Me | 3,5-Me₂ | CO-c-Pen | OMe | 1.5019(26.8) |
| 1-350 | i-Bu | CH=CH₂ | 3,5-Me₂ | H | OMe | 124-130 |
| 1-351 | i-Bu | CH=CH₂ | 3,5-Me₂ | CO-i-Pr | OMe | 1.5044(25.8) |
| 1-352 | i-Bu | Me | 3,5-Me₂ | CO(2,4-Cl₂-Ph) | OMe | 1.5220(26.1) |
| 1-353 | i-Bu | Me | 3,5-Me₂ | CO(3,4-Cl₂-Ph) | OMe | 53 |
| 1-354 | n-Pr | Me | 3,5-Me₂ | CO-i-Pr | OMe | 1.5075(25.1) |
| 1-355 | n-Pr | Me | 3-CF₃-5-Me | CO-i-Pr | OMe | 1.4741(25.8) |
| 1-356 | Et | Me | 3-CF₃-5-Me | COOCH₂CH=CH₂ | OMe | 1.4781(25.9) |
| 1-357 | n-Pr | Me | 3,5-Me₂ | CO-t-Bu | OMe | 1.4888(26.0) |
| 1-358 | n-Pr | Me | 3,5-Me₂ | CO(4-Cl-Ph) | OMe | 41 |
| 1-359 | Et | Me | 3,5-Me₂ | n-Pen | OMe | 1.4897(25.0) |
| 1-360 | Et | Me | 3,5-Me₂ | CH₂(4-F-Ph) | OMe | 107.9 |
| 1-361 | Et | Me | 3,5-Me₂ | CO-c-Bu | OMe | 1.4939(32.1) |
| 1-362 | Et | Me | 3,5-Me₂ | CO-i-Pr | OMe | 100.3-103.4 |
| 1-363 | Et | Me | 3,5-Me₂ | CO-s-Bu | OMe | 1.5031(22.9) |
| 1-364 | Et | Me | 3,5-Me₂ | CO-t-Bu | OMe | 108 |
| 1-365 | Et | Me | 3,5-Me₂ | COCMe₂Et | OMe | 1.4983(20.5) |
| 1-366 | Et | Me | 3,5-Me₂ | COCH₂OMe | OMe | 1.4958(21.6) |
| 1-367 | Et | Me | 3,5-Me₂ | COCHEt₂ | OMe | 1.4991(21.8) |
| 1-368 | Et | Me | 3,5-Me₂ | CO-c-Pen | OMe | 1.4977(30.5) |
| 1-369 | Et | Me | 3,5-Me₂ | CO-c-Hex | OMe | 1.4934(25.2) |
| 1-370 | Et | Me | 3,5-Me₂ | COCH₂OPh | OMe | amorphous |
| 1-371 | Et | Me | 3,5-Me₂ | COCH₂-t-Bu | OMe | 1.4962(32.1) |
| 1-372 | Et | Me | 3,5-Me₂ | CO(4-CF₃-Ph) | OMe | 1.5023(32.2) |
| 1-373 | Et | Me | 3,5-Me₂ | CO-C(cyclopropyl)-Ph | OMe | 1.4211(32.0) |

TABLE 1-continued

Formula (I-4)

(I-4)
(Xn = H)

| No. | G | Y¹ | Y²ₘ | R¹ | R² | Property |
|---|---|---|---|---|---|---|
| 1-374 | Et | Me | 3,5-Me₂ | CH₂OCH₂CH₂OMe | OMe | 1.4892(31.0) |
| 1-375 | Et | Me | 3,5-Me₂ | CH₂O-i-Pr | OMe | 1.4855(30.2) |
| 1-376 | Et | Me | 3,5-Me₂ | CH₂O-i-Bu | OMe | 1.4849(33.2) |
| 1-377 | Et | Me | 3,5-Me₂ | CH₂O-n-Pr | OMe | 1.4982(23.1) |
| 1-378 | Et | Me | 3,5-Me₂ | CH₂O-n-Bu | OMe | 1.4940(23.2) |
| 1-379 | Et | Me | 3,5-Me₂ | COOCH₂CCl₃ | OMe | 145.2-145.8 |
| 1-380 | Et | Me | 3,5-Me₂ | COO-n-Pen | OMe | 1.4960(20.2) |
| 1-381 | Et | Me | 3-CF₃-5-Me | COEt | H | 127-128 |
| 1-382 | Et | Me | 3-CF₃-5-Me | CO-c-Bu | OMe | 1.4818(19.1) |
| 1-383 | Et | Me | 3-CF₃-5-Me | CO-s-Bu | OMe | 1.4701(24.4) |
| 1-384 | Et | Me | 3-CF₃-5-Me | COCHEt₂ | OMe | 1.4724(24.3) |
| 1-385 | Et | Me | 3-CF₃-5-Me | CH₂O-n-Bu | OMe | 1.4670(23.7) |
| 1-386 | Et | Me | 3-CF₃-5-Me | CH₂O-i-Bu | OMe | 1.4659(21.8) |
| 1-387 | Et | Me | 3-CF₃-5-Me | CH₂O-n-Pr | OMe | 1.4672(21.8) |
| 1-388 | Et | Me | 3-Me-5-Cl | H | OMe | 127.3-128.5 |
| 1-389 | Et | Me | 3-Me-5-Cl | CO-i-Pr | OMe | 134.1-135.4 |
| 1-390 | Et | Me | 3-Me-5-Cl | CO-c-Bu | OMe | 136.1-137.2 |
| 1-391 | Et | Me | 3-Me-5-Cl | CO-t-Bu | OMe | 108.6-110.4 |
| 1-392 | Et | Me | 3-Me-5-Cl | COO-i-Bu | OMe | 1.4931(32.1) |
| 1-393 | Et | Me | 3-Me-5-Cl | CH₂O-i-Pr | OMe | 1.4884(30.5) |
| 1-394 | Et | Me | 3-Me-5-Cl | CH₂O-n-Bu | OMe | 1.4875(29.1) |
| 1-395 | Et | Me | 3-Me | H | OMe | 183.8-185.4 |
| 1-396 | Et | Me | 3-Me | CO-i-Pr | OMe | 114.4-114.9 |
| 1-397 | Et | Me | 3-Me | CO-c-Pen | OMe | 1.4975(31.0) |
| 1-398 | Et | Me | 3-Me | CH₂O-i-Pr | OMe | 1.4902(23.4) |
| 1-399 | Et | Me | 3,5-Me₂ | CO-n-Pr | OEt | 1.4932(23.0) |
| 1-400 | Et | Me | 3,5-Me₂ | CO-i-Pr | OEt | 80-81 |
| 1-401 | n-Pr | Me | 3,5-Me₂ | COOCH₂CH=CH₂ | OMe | 1.4841(23.7) |
| 1-402 | n-Pr | Me | 3,5-Me₂ | COOCH₂CHEt-n-Bu | OMe | 1.4894(23.8) |
| 1-403 | n-Pr | Me | 3,5-Me₂ | COCH₂OMe | OMe | paste |
| 1-404 | n-Pr | Me | 3,5-Me₂ | Me | OMe | 1.4983(22.0) |
| 1-405 | n-Pr | Me | 3,5-Me₂ | Et | OMe | 1.4970(20.0) |
| 1-406 | n-Pr | Me | 3,5-Me₂ | CH₂CH=CH₂ | OMe | 1.5019(23.2) |
| 1-407 | n-Pr | Me | 3,5-Me₂ | (CH₂)₇Me | OMe | 1.4880(23.5) |
| 1-408 | n-Pr | Me | 3-CF₃-5-Me | COOMe | H | 140-145 |
| 1-409 | n-Pr | Me | 3-CF₃-5-Me | COOEt | H | 129-130 |
| 1-410 | n-Pr | Me | 3-CF₃-5-Me | COEt | H | 140-145 |
| 1-411 | n-Pr | Me | 3-CF₃-5-Me | CO-i-Pr | H | 135-137 |
| 1-412 | n-Pr | Me | 3-CF₃-5-Me | CH₂O-n-Pr | OMe | 1.4673(21.8) |
| 1-413 | n-Pr | Me | 3-CF₃-5-Me | CH₂O-t-Bu | OMe | 1.4669(21.7) |
| 1-414 | i-Bu | Me | 3,5-Me₂ | Me | OMe | paste |
| 1-415 | i-Bu | Me | 3,5-Me₂ | n-Pr | OMe | paste |
| 1-416 | i-Bu | Me | 3,5-Me₂ | CH₂CH=CH₂ | OMe | 70-71 |
| 1-417 | i-Bu | Me | 3,5-Me₂ | CH₂(4-NO₂-Ph) | OMe | paste |
| 1-418 | i-Bu | Me | 3,5-Me₂ | CH₂Ph | OMe | 90-97 |
| 1-419 | i-Bu | Me | 3,5-Me₂ | CH₂(4-Me-Ph) | OMe | paste |
| 1-420 | i-Bu | Me | 3,5-Me₂ | CH₂O-n-Pr | OMe | 59-65 |
| 1-421 | i-Bu | Me | 3,5-Me₂ | CH₂O-n-Bu | OMe | paste |
| 1-422 | i-Bu | Me | 3,5-Me₂ | CH₂O-i-Pr | OMe | paste |
| 1-423 | i-Bu | Me | 3,5-Me₂ | CH₂O-i-Bu | OMe | 80-82 |
| 1-424 | i-Bu | Me | 3,5-Me₂ | CH₂O-t-Bu | OMe | paste |
| 1-425 | i-Bu | Me | 3,5-Me₂ | CH₂O-s-Bu | OMe | paste |
| 1-426 | i-Bu | Me | 3,5-Me₂ | CH₂OCH₂CF₃ | OMe | paste |
| 1-427 | i-Bu | Me | 3,5-Me₂ | CH₂OCH₂CH=CH₂ | OMe | paste |
| 1-428 | i-Bu | Me | 3,5-Me₂ | CH₂O(CH₂)₇Me | OMe | paste |
| 1-429 | i-Bu | Me | 3,5-Me₂ | CO-c-Bu | OMe | paste |
| 1-430 | i-Bu | Me | 3,5-Me₂ | CO-s-Bu | OMe | 106.1-107.8 |
| 1-431 | i-Bu | Me | 3,5-Me₂ | COCHEt₂ | OMe | 97.2-101.8 |
| 1-432 | i-Bu | Me | 3,5-Me₂ | COCMe₂Br | OMe | 93-106 |
| 1-433 | i-Bu | Me | 3,5-Me₂ | CO-c-Hex | OMe | 1.5035(24.7) |
| 1-434 | i-Bu | Me | 3,5-Me₂ | CH₂(2,4,6-Cl₃-Ph) | OMe | 64.2-66.7 |

TABLE 1-continued

Formula (I-4)

(I-4)
(Xn = H)

| No. | G | Y¹ | Y²_m | R¹ | R² | Property |
|---|---|---|---|---|---|---|
| 1-435 | i-Bu | Me | 3,5-Me₂ | ⊲CO | OMe | 1.4991(20.5) |
| 1-436 | i-Bu | Me | 3,5-Me₂ | COCHMeOMe | OMe | 1.4977(20.6) |
| 1-437 | i-Bu | Me | 3,5-Me₂ | COCMe₂OMe | OMe | 1.4906(23.6) |
| 1-438 | i-Bu | Me | 3,5-Me₂ | COOPh | OMe | 135.3-136.1 |
| 1-439 | i-Bu | Me | 3-Me-5-CF₃ | COO-i-Bu | OMe | 1.4733(21.2) |
| 1-440 | i-Bu | Me | 3-Me-5-CF₃ | CO-t-Bu | OMe | 1.4745(21.2) |
| 1-441 | i-Bu | Me | 3-Me-5-CF₃ | CO-i-Pr | OMe | 1.4722(32.1) |
| 1-442 | i-Bu | Me | 3-Me-5-CF₃ | CO-c-Pr | OMe | 1.4780(32.0) |
| 1-443 | i-Bu | Me | 3-CF₃-5-Me | COEt | OMe | 1.4727(24.1) |
| 1-444 | i-Bu | Me | 3-CF₃-5-Me | CO-i-Pr | OMe | 1.4720(24.2) |
| 1-445 | i-Bu | Me | 3-CF₃-5-Me | CH₂O-n-Pr | OMe | 1.4658(22.7) |
| 1-446 | i-Bu | Me | 3-CF₃-5-Me | CH₂O-n-Bu | OMe | 1.4670(22.5) |
| 1-447 | i-Bu | Me | 3-CF₃-5-Me | CH₂O-i-Bu | OMe | 1.4625(21.9) |
| 1-448 | i-Bu | Me | 3-Me-5-F | CO-t-Bu | OMe | amorphous |
| 1-449 | i-Bu | Me | 3-Me-5-Cl | CO-i-Pr | OMe | 124-124.4 |
| 1-450 | i-Bu | Me | 3-Me-5-Cl | CO-t-Bu | OMe | 1.4860(31.4) |
| 1-451 | i-Bu | Me | 3-Me-5-Cl | CO-c-Bu | OMe | 114-115.3 |
| 1-452 | i-Bu | Me | 3-Me-5-Cl | COCH₂OMe | OMe | amorphous |
| 1-453 | i-Bu | Me | 3-Me-5-Cl | CO-c-Pen | OMe | 136.2-137 |
| 1-454 | i-Bu | Me | 3-Me-5-Cl | CH₂O-n-Pr | OMe | 1.4887(31.6) |
| 1-455 | i-Bu | Me | 3-Me-5-Cl | CH₂O-i-Bu | OMe | 60.7-64.7 |
| 1-456 | i-Bu | Me | 3-Me | CO-i-Pr | OMe | 67.3-68.2 |
| 1-457 | i-Bu | Me | 3-Me | CO-t-Bu | OMe | 124.1-125.5 |
| 1-458 | i-Bu | Me | 3-Me | CO-s-Bu | OMe | 1.4914(32.0) |
| 1-459 | i-Bu | Me | 3-Me | CO-c-Bu | OMe | 83-88.6 |
| 1-460 | i-Bu | Me | 3-Me | CO-c-Pen | OMe | 1.4990(31.7) |
| 1-461 | i-Bu | Me | 3-Me | COCHEt₂ | OMe | 1.4905(28.5) |
| 1-462 | i-Bu | Me | 3-Me | CH₂O-i-Pr | OMe | 1.4817(31.7) |
| 1-463 | i-Bu | H | 3,5-Me₂ | H | OMe | 82.8-90.5 |
| 1-464 | i-Bu | Et | 3,5-Me₂ | H | OMe | 162-163 |
| 1-465 | i-Bu | CH₂CF₃ | 3,5-Me₂ | H | OMe | 176-177 |
| 1-466 | i-Bu | Me | 3,5-Me₂ | CO-i-Pr | F | 1.4860(22.7) |
| 1-467 | CH₂CHMeEt | Me | 3,5-Me₂ | COEt | OMe | 1.4929(20.1) |
| 1-468 | CH₂CHMeEt | Me | 3,5-Me₂ | CO-i-Pr | OMe | 1.4910(20.0) |
| 1-469 | n-Bu | Me | 3,5-Me₂ | COEt | OMe | 1.4895(20.6) |
| 1-470 | n-Bu | Me | 3,5-Me₂ | CO-i-Pr | OMe | 1.4835(18.9) |
| 1-471 | CH₂CH-c-Pen | Me | 3-CF₃5-Me | H | H | 200201 |
| 1-472 | CH₂CH₂CHMe₂ | Me | 3,5-Me₂ | COEt | OMe | 1.4960(20.5) |
| 1-473 | CH₂CH₂CHMe₂ | Me | 3,5-Me₂ | CO-i-Pr | OMe | 1.4950(21.6) |
| 1-474 | Et | i-Pr | 3,5-Me₂ | H | OEt | 173-174 |
| 1-475 | Et | i-Pr | 3,5-Me₂ | Ac | OEt | 88-89 |
| 1-476 | Et | Me | 3,5-Me₂ | H | O-n-Pr | 104-105 |
| 1-477 | Et | Me | 3,5-Me₂ | CO-n-Pr | O-n-Pr | 1.4833(33.0) |
| 1-478 | Et | Me | 3,5-Me₂ | CO-i-Pr | O-n-Pr | 1.4919(33.0) |
| 1-479 | Et | Me | 3,5-Me₂ | CO-t-Bu | O-n-Pr | 1.4848(32.0) |
| 1-480 | Et | Me | 3,5-Me₂ | CH₂OEt | O-n-Pr | 1.4729(23.5) |
| 1-481 | Et | Me | 3-I-5-Me | H | H | 134-135 |
| 1-482 | Et | Me | 3,5-Me₂ | COCHMeCOEt | OEt | |
| 1-483 | n-Pr | Me | 3,5-Me₂ | CO-n-Pr | OMe | 1.4959(31.2) |
| 1-484 | n-Pr | Me | 3,5-Me₂ | CO-s-Bu | OMe | 1.4960(32.3) |
| 1-485 | n-Pr | Me | 3,5-Me₂ | CO-c-Pen | OMe | 1.4880(29.0) |
| 1-486 | n-Pr | Me | 3,5-Me₂ | CH₂O-n-Pr | OMe | 1.4869(28.0) |
| 1-487 | n-Pr | Me | 3,5-Me₂ | CH₂O-i-Pr | OMe | 1.4819(29.3) |
| 1-488 | n-Pr | Me | 3-Me-5-Cl | H | OMe | 135.4-139.0 |
| 1-489 | n-Pr | Me | 3-Me-5-Cl | CO-i-Pr | OMe | 128.1-128.2 |
| 1-490 | n-Pr | Me | 3-Me-5-Cl | CO-s-Bu | OMe | 99.2-99.7 |
| 1-491 | n-Pr | Me | 3-Me-5-Cl | CO-c-Pr | OMe | 123.0-123.9 |

TABLE 1-continued

Formula (I-4)

![Structure of Formula (I-4)]

(I-4)
(Xn = H)

| No. | G | Y$^1$ | Y$^2_m$ | R$^1$ | R$^2$ | Property |
|---|---|---|---|---|---|---|
| 1-492 | n-Pr | Me | 3-Me 5-Cl | CO-c-Pen | OMe | 141.7-142.1 |
| 1-493 | n-Pr | Me | 3-Me-5-Cl | CH$_2$OEt | OMe | 1.4954(20.7) |
| 1-494 | n-Pr | Me | 3-I-5-Me | H | H | 183-185 |
| 1-495 | n-Pr | Me | 3-Me | H | OMe | 146.8-147.0 |
| 1-496 | n-Pr | Me | 3-Me | CO-i-Pr | OMe | 61.6-62.9 |
| 1-497 | n-Pr | Me | 3-Me | CO-s-Bu | OMe | 1.4960(22.2) |
| 1-498 | n-Pr | Me | 3-Me | CO-c-Pen | OMe | 1.4991(22.1) |
| 1-499 | n-Pr | Me | 3-Me | CH$_2$O-n-Pr | OMe | 1.4864(22.8) |
| 1-500 | n-Pr | Me | 3-Me | CH$_2$O-i-Pr | OMe | 1.4863(22.4) |
| 1-501 | n-Pr | Me | 3,5-Me$_2$ | CO-n-Pr | OEt | 1.4892(22.7) |
| 1-502 | n-Pr | Me | 3,5-Me$_2$ | CO-i-Pr | OEt | 1.4910(22.8) |
| 1-503 | n-Pr | Me | 3,5-Me$_2$ | H | O-n-Pr | 158-159.5 |
| 1-504 | n-Pr | Me | 3,5-Me$_2$ | COEt | O-n-Pr | 1.4975(20.5) |
| 1-505 | n-Pr | Me | 3,5-Me$_2$ | CO-n-Pr | O-n-Pr | 1.4940(20.5) |
| 1-506 | n-Pr | Me | 3,5-Me$_2$ | CO-i-Pr | O-n-Pr | 1.4960(20.6) |
| 1-507 | i-Bu | CH$_2$CF$_3$ | 3,5-Me$_2$ | COEt | OMe | 137-138 |
| 1-508 | i-Bu | CH$_2$CF$_3$ | 3,5-Me$_2$ | CO-i-Pr | OMe | |
| 1-509 | i-Bu | i-Pr | 3,5-Me$_2$ | H | OMe | 166-167 |
| 1-510 | i-Bu | i-Pr | 3,5-Me$_2$ | CO-i-Pr | OMe | 107-108 |
| 1-511 | i-Bu | Me | 3-Me-5-Cl | H | F | 143.2-144.7 |
| 1-512 | i-Bu | Me | 3-Me-5-Cl | CO-i-Pr | F | 1.4888(23.0) |
| 1-513 | i-Bu | Me | 3-Cl-5-Me | H | OMe | 153-161 |
| 1-514 | i-Bu | Me | 3-Cl-5-Me | CO-i-Pr | OMe | paste |
| 1-515 | i-Bu | Me | 3-Cl-5-Me | CH$_2$O-i-Pr | OMe | paste |
| 1-516 | i-Bu | Me | 3-Cl-5-Me | COOMe | OMe | amorphous |
| 1-517 | i-Bu | Me | 3-Br-5-Me | H | OMe | 172-174 |
| 1-518 | i-Bu | Me | 3-Br-5-Me | CO-i-Pr | OMe | paste |
| 1-519 | i-Bu | Me | 3-Br-5-Me | CH$_2$O-i-Pr | OMe | paste |
| 1-520 | i-Bu | Me | 3-I-5-Me | H | H | 178-183 |
| 1-521 | i-Bu | Me | 3-Br-5-Me | COOMe | OMe | paste |
| 1-522 | i-Bu | Me | 3-I-5-Me | H | OMe | amorphous |
| 1-523 | i-Bu | Me | 3-I-5-Me | COOMe | OMe | paste |
| 1-524 | i-Bu | Me | 3-I-5-Me | CO-i-Pr | OMe | paste |
| 1-525 | i-Bu | Me | 3-I-5-Me | CH$_2$OEt | OMe | 100-103 |
| 1-526 | i-Bu | Me | 3-I-5-Me | CH$_2$O-i-Pr | OMe | 100-102 |
| 1-527 | i-Bu | Me | 3,5-Me$_2$ | CH$_2$CH=CMe$_2$ | OMe | 81-83 |
| 1-528 | CH=CMe$_2$ | Me | 3,5-Me$_2$ | H | OMe | |
| 1-529 | i-Bu | Me | 5-CF$_3$ | H | OMe | 170 |
| 1-530 | i-Bu | Me | 5-CF$_3$ | CO-i-Pr | OMe | 1.4680(22.8) |
| 1-531 | i-Bu | Et | 3,5-Me$_2$ | CO-i-Pr | OMe | 1.4913(23.0) |
| 1-532 | CH=CMe$_2$ | Me | 3,5-Me$_2$ | CO-i-Pr | OMe | |
| 1-533 | i-Bu | Me | 3,5-Me$_2$ | CO-n-Pr | OEt | 1.4870(22.5) |
| 1-534 | i-Bu | Me | 3,5-Me$_2$ | H | O-n-Pr | 138-139 |
| 1-535 | i-Bu | Me | 3-I | H | OMe | 210-218 |
| 1-536 | i-Bu | Me | 3-Br | H | OMe | 203 |
| 1-537 | i-Bu | Me | 3-Cl | H | OMe | 174-182 |
| 1-538 | i-Bu | Me | 3,5-Cl$_2$ | H | OMe | 132 |
| 1-539 | i-Bu | Me | 3-I | CO-i-Pr | OMe | paste |
| 1-540 | i-Bu | Me | 3-Br | CO-i-Pr | OMe | paste |
| 1-541 | i-Bu | Me | 3-Cl | CO-i-Pr | OMe | paste |
| 1-542 | i-Bu | Me | 3-CF$_3$ | CO-i-Pr | OMe | paste |
| 1-543 | i-Bu | Me | 3,5-Cl$_2$ | CO-i-Pr | OMe | 113-114 |
| 1-544 | i-Bu | Me | 3,5-Me$_2$ | 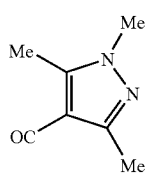 | F | amorphous |

TABLE 1-continued

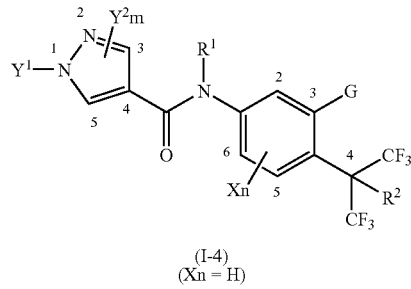

Formula (I-4)

(I-4)
(Xn = H)

| No. | G | Y¹ | Y²ₘ | R¹ | R² | Property |
|---|---|---|---|---|---|---|
| 1-545 | i-Bu | Me | 3,5-Me₂ | Me-thiophene(OC) | F | amorphous |
| 1-546 | i-Bu | Me | 3,5-Me₂ | Me-thiazole(OC)-Me | OMe | 150.4-151.2 |
| 1-547 | i-Bu | Me | 3,5-Me₂ | CH₂OAc | OMe | 94-95 |
| 1-548 | i-Bu | Me | 3,5-Me₂ | CH₂OC(=O)Et | OMe | 99 |
| 1-549 | i-Bu | Me | 3,5-Me₂ | CH₂OC(=O)-i-Pr | OMe | 112 |
| 1-550 | i-Bu | Me | 3,5-Me₂ | COSMe | OMe | |
| 1-551 | i-Bu | Me | 3,5-Me₂ | COSEt | OMe | |

TABLE 2

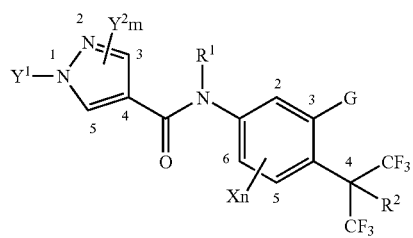

Formula (I-4)

(I-4)
(Y¹ = Me)

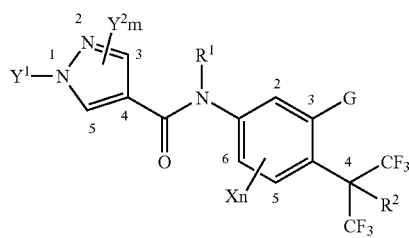

Formula (I-4)

(I-4)
(Y¹ = Me)

| No. | G | Xn | Y²ₘ | R¹ | R² | Property |
|---|---|---|---|---|---|---|
| 2-1 | Et | 6-Me | 3,5-Me₂ | H | H | |
| 2-2 | Et | 6-Me | 3,5-Me₂ | Ac | H | |
| 2-3 | Et | 6-Me | 3,5-Me₂ | H | OMe | |
| 2-4 | Et | 6-Me | 3,5-Me₂ | Ac | OMe | |
| 2-5 | Et | 6-Me | 3,5-Me₂ | H | OEt | |
| 2-6 | Et | 6-Me | 3,5-Me₂ | Ac | OEt | |
| 2-7 | Et | 6-Me | 3-CF₃-5-Me | H | H | |
| 2-8 | Et | 6-Me | 3-CF₃-5-Me | Ac | H | |
| 2-9 | Et | 6-Me | 3-CF₃-5-Me | H | OMe | |
| 2-10 | Et | 6-Me | 3-CF₃-5-Me | Ac | OMe | |
| 2-11 | Et | 6-Me | 3-CF₃-5-Me | H | OEt | |
| 2-12 | Et | 6-Me | 3-CF₃-5-Me | Ac | OEt | |
| 2-13 | n-Pr | 6-Me | 3,5-Me₂ | H | H | 128-131 |
| 2-14 | n-Pr | 6-Me | 3,5-Me₂ | Ac | H | |
| 2-15 | n-Pr | 6-Me | 3,5-Me₂ | H | OMe | 132-134 |
| 2-16 | n-Pr | 6-Me | 3,5-Me₂ | Ac | OMe | 1.4905(25.9) |
| 2-17 | n-Pr | 6-Me | 3,5-Me₂ | H | OEt | 154-155 |
| 2-18 | n-Pr | 6-Me | 3,5-Me₂ | Ac | OEt | |
| 2-19 | n-Pr | 6-Me | 3-CF₃-5-Me | H | H | |
| 2-20 | n-Pr | 6-Me | 3-CF₃-5-Me | Ac | H | |
| 2-21 | n-Pr | 6-Me | 3-CF₃-5-Me | H | OMe | 104-106 |
| 2-22 | n-Pr | 6-Me | 3-CF₃-5-Me | Ac | OMe | 1.4751(26.7) |
| 2-23 | n-Pr | 6-Me | 3-CF₃-5-Me | H | OEt | 152-153 |
| 2-24 | n-Pr | 6-Me | 3-CF₃-5-Me | Ac | OEt | |
| 2-25 | n-Pr | 6-Me | 3-Me-5-Cl | H | OMe | 127-128.5 |
| 2-26 | n-Pr | 6-Me | 3-CF₃-5-Me | COEt | OMe | 151-152 |
| 2-27 | i-Bu | 6-Cl | 3,5-Me₂ | H | OMe | 106-109 |
| 2-28 | i-Bu | 6-Cl | 3,5-Me₂ | Ac | OMe | amorphous |
| 2-29 | Et | 6-Me | 3,5-Me₂ | CO-c-Pr | OMe | 138-140 |
| 2-30 | Et | 6-Me | 3,5-Me₂ | COEt | OMe | 132-134 |
| 2-31 | Et | 6-Me | 3-CF₃-5-Me | CO-n-Pr | OMe | 1.4960(26.6) |
| 2-32 | n-Pr | 6-Me | 3-CF₃-5-Me | COOMe | OMe | 165-166 |
| 2-33 | i-Bu | 6-Me | 3,5-Me₂ | H | OMe | 126-127 |
| 2-34 | n-Pr | 6-Me | 3,5-Me₂ | CO-i-Pr | OMe | 1.4955(33.5) |
| 2-35 | n-Pr | 6-Me | 3,5-Me₂ | CO-t-Bu | OMe | 128.5-130.2 |
| 2-36 | n-Pr | 6-Me | 3,5-Me₂ | COCHEt₂ | OMe | 1.4918(32.6) |
| 2-37 | n-Pr | 6-Me | 3,5-Me₂ | COO-i-Bu | OMe | 1.4870(30.1) |
| 2-38 | i-Bu | 6-Me | 3,5-Me₂ | COEt | OMe | amorphous |
| 2-39 | Et | 6-Me | 3,5-Me₂ | CO-i-Pr | OMe | 1.4952 (32.0) |
| 2-40 | n-Pr | 6-Me | 3-Me | H | OMe | amorphous |
| 2-41 | n-Pr | 6-Me | 3-Me | CO-i-Pr | OMe | paste |
| 2-42 | n-Pr | 6-Me | 3,5-Me₂ | CO-i-Pr | OEt | 111-112 |
| 2-43 | i-Bu | 6-Me | 3,5-Me₂ | CO-i-Pr | OMe | 38-42 |
| 2-44 | n-Pr | 6-Me | 3-CF₃-5-Me | CO-i-Pr | OMe | 155 |

TABLE 2-continued

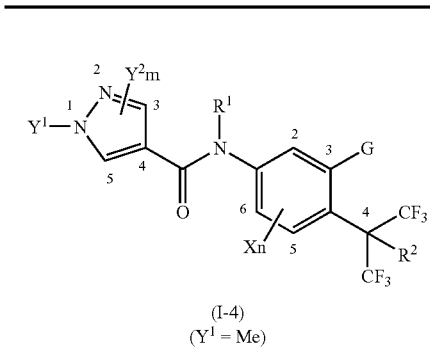

Formula (I-4)

(I-4)
($Y^1$ = Me)

| No. | G | Xn | $Y^2_m$ | $R^1$ | $R^2$ | Property |
|---|---|---|---|---|---|---|
| 2-45 | i-Bu | 6-Me | 3-$CF_3$-5-Me | H | OMe | 68-70 |
| 2-46 | n-Pr | 6-Me | 3,5-$Me_2$ | H | OH | 192-195 |

TABLE 3

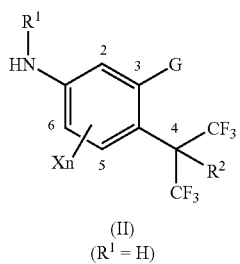

Formula (II)

(II)
($R^1$ = H)

| No | G | Xn | $R^2$ | $^1$H-NMR [$CDCl_3$/TMS, δ value (ppm)] |
|---|---|---|---|---|
| 3-1 | n-Pr | 6-Me | F | 7.09 (s, 1 H), 6.54 (s, 1 H), 3.76 (bs, 2 H), 2.63 (m, 2 H), 2.13 (s, 3 H), 1.58 (m, 2 H), 0.96 (t, 3 H) |
| 3-2 | n-Pr | 6-Me | H | 7.18 (s, 1 H), 6.54 (s, 1 H), 4.45-4.20 (br, 2 H), 4.27 (m, 1 H), 2.50 (dd, 2 H), 2.14 (s, 3 H), 1.57 (m, 2 H), 0.98 (t, 3 H) |
| 3-3 | n-Pr | 6-Me | OMe | 7.10 (s, 1 H), 6.66 (s, 1 H), 3.72 (bs, 2 H), 3.42 (s, 3 H), 2.84 (m, 2 H), 2.14 (s, 3 H), 1.61 (m, 2 H), 1.00 (t, 3 H) |
| 3-4 | Et | 6-Me | F | 7.09 (s, 1 H), 6.56 (s, 1 H), 3.78 (bs, 2 H), 2.71 (m, 2 H), 2.14 (s, 3 H), 1.19 (td, 3 H) |
| 3-5 | Et | 6-Me | OMe | 7.10 (s, 1 H), 6.68 (s, 1 H), 3.75 (bs, 2 H), 3.41 (s, 3 H), 2.91 (dd, 2 H), 2.15 (s, 3 H), 1.22 (t, 3 H) |
| 3-6 | Et | H | O-n-Pr | 7.22 (d, 1 H), 6.67 (d, 1 H), 6.52 (dd, 1 H), 3.80 (br, 2 H), 3.46 (t, 2 H), 2.92 (dd, 2 H), 1.69 (dd, 2 H), 1.21 (t, 3 H), 0.94 (t, 3 H) |
| 3-7 | n-Pr | H | O-n-Pr | 7.22 (d, 1 H), 6.66 (d, 1 H), 6.51 (dd, 1 H), 3.78 (br, 2 H), 3.47 (t, 2 H), 2.85 (m, 2 H), 1.70 (dd, 2 H), 1.60 (m, 2 H), 1.00 (t, 3 H), 0.94 (t, 3 H) |
| 3-8 | i-Bu | H | O-n-Pr | 7.24 (d, 1 H), 6.70 (d, 1 H), 6.53 (dd, 1 H), 3.79 (bs, 2 H), 3.47 (t, 2 H), 2.81 (d, 2 H), 2.10 (m, 1 H), 1.70 (m, 2 H), 0.95 (t, 3 H), 0.91 (d, 6 H) |

TABLE 4

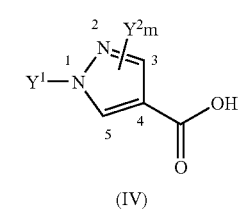

Formula (IV)

(IV)

| No | $Y^1$ | $Y^2_m$ | melting point (° C.) |
|---|---|---|---|
| 4-1 | Me | 3-Me-5-$CF_3$ | 124-125.5 |

TABLE 5

| No. | $^1$H-NMR[$CDCl_3$/TMS, δ value (ppm)] |
|---|---|
| 1-106 | 7.61(d, 2H), 7.52(d, 1H), 7.17(m, 4H), 7.11(m, 1H), 3.69(s, 3H), 3.47(s, 3H), 2.86(d, 2H), 2.39(s, 3H), 2.37(s, 3H), 1.96(m, 1H), 0.73(d, 6H) |
| 1-107 | 8.27(d, 2H), 7.83(d, 2H), 7.59(d, 1H), 7.22(d, 1H), 7.17(m, 1H), 6.97(s, 1H), 3.66(s, 3H), 3.51(s, 3H), 2.91(d, 2H), 2.36(s, 3H), 1.97(m, 1H), 0.77(d, 6H) |
| 1-116 | 8.04(s, 1H), 7.73(br, 1H), 7.72(d, 1H), 7.50(d, 1H), 7.43(dd, 1H), 4.01(s, 3H), 3.47(s, 3H), 2.93(d, 2H), 2.21(m, 1H), 0.94(d, 6H) |
| 1-124 | 7.80(dd, 2H), 7.49(d, 1H), 7.13(dd, 2H), 7.02(dd, 1H), 6.89(d, 1H), 4.40-4.31(m, 1H), 3.57(s, 3H), 2.42(d, 2H), 2.28(s, 3H), 2.22(s, 3H), 1.70-1.59(m, 1H), 0.78(d, 6H) |
| 1-156 | 7.41(d, 1H), 7.01(dd, 1H), 6.96(d, 1H), 3.98(dd, 2H), 3.56(s, 3H), 3.44(s, 3H), 2.79(d, 2H), 2.06(s, 3H), 2.00(s, 3H), 1.86(m, 1H), 1.25(dd, 3H), 0.74(d, 6H) |
| 1-160 | 7.47(d, 1H), 7.16-7.05(m, 2H), 3.67(3, 3H), 3.60(dd, 2H), 3.04(m, 1H), 2.88(d, 2H), 2.37(s, 3H), 2.25(s, 3H), 1.97(m, 1H), 1.31(t, 3H), 1.26(d, 6H), 0.77(d, 6H) |
| 1-331 | 7.48(d, 1H), 7.10(d, 1H), 7.08(s, 1H), 5.11(q, 1H), 3.64(s, 3H), 3.45(s, 3H), 2.96(dd, 1H), 2.74(dd, 1H), 2.31(s, 3H), 2.24(s, 3H), 1.92(m, 1H), 1.77(d, 3H), 0.84(d, 3H), 0.65(d, 3H) |
| 1-370 | 7.41(d, 1H), 7.28(m, 2H), 7.08(d, 1H), 6.98(m, 2H), 6.84(m, 2H), 4.98(s, 2H), 3.63(s, 3H), 3.40(s, 3H), 2.96(q, 2H), 2.18(s, 3H), 2.14(s, 3H), 1.26(t, 3H) |
| 1-403 | 7.43(d, 1H), 7.14(d, 1H), 7.18(m, 1H), 4.32(s, 2H), 3.66(s, 3H), 3.43(s, 3H), 3.39(s, 3H), 2.92(m, 2H), 2.31(s, 3H), 2.23(s, 3H), 1.51(m, 2H), 0.94(t, 3H) |
| 1-414 | 7.41(d, 1H), 7.01(m, 2H), 3.58(s, 3H), 3.48(s, 3H), 3.44(s, 3H), 2.79(d, 2H), 2.06(s, 3H), 2.00(s, 3H), 1.85(m, 1H), 0.76(d, 6H) |
| 1-415 | 7.39(d, 1H), 7.00(dd, 1H), 6.97(d, 1H), 3.88(m, 2H), 3.56(s, 3H), 3.44(s, 3H), 2.78(d, 2H), 2.05(s, 3H), 2.00(s, 3H), 1.84(m, 1H), 1.66(m, 2H), 0.95(t, 3H), 0.75(d, 6H) |
| 1-417 | 8.18(d, 2H), 7.50(d, 2H), 7.38(d, 1H), 6.95(dd, 1H), 6.88(d, 1H), 5.22(s, 2H), 3.58(s, 3H), 3.41(s, 3H), 2.73(d, 2H), 2.08(s, 3H), 1.99(s, 3H), 1.73(m, 1H), 0.70(d, 6H) |
| 1-419 | 7.33(d, 1H), 7.23(d, 2H), 6.93(dd, 1H), 6.89(d, 1H), 6.83(d, 2H), 5.06(s, 2H), 3.79(s, 3H), 3.56(s, 3H), 3.40(s, 3H), 2.73(d, 2H), 2.05(s, 3H), 2.01(s, 3H), 1.74(m, 1H), 0.70(d, 6H) |
| 1-421 | 7.40(d, 1H), 7.16(m, 2H), 5.30(s, 2H), 3.61(t, 2H), 3.59(s, 3H), 3.43(s, 3H), 2.80(d, 2H), 2.09(s, 3H), 2.04(s, 3H), 1.87(m, 1H), 1.59(m, 2H), 1.37(m, 2H), 0.91(t, 3H), 0.76(d, 6H) |
| 1-422 | 7.39(d, 1H), 7.18(m, 2H), 5.31(s, 2H), 3.91(m, 1H), 3.59(s, 3H), 3.43(s, 3H), 2.80(d, 2H), 2.08(s, 3H), 2.04(s, 3H), 1.87(m, 1H), 1.22(d, 6H), 0.77(d, 6H) |
| 1-424 | 7.39(d, 1H), 7.23(m, 2H), 5.23(s, 2H), 3.58(s, 3H), 3.43(s, 3H), 2.80(d, 2H), 2.07(s, 6H), 1.89(m, 1H), 1.26(s, 9H), 0.78(d, 6H) |
| 1-425 | 7.39(d, 1H), 7.17(m, 2H), 5.43(d, 1H), 5.22(d, 1H), 3.68(m, 1H), 3.59(s, 3H), 3.43(s, 3H), 2.80(d, 2H), 2.08(s, 3H), 2.04(s, 3H), 1.87(m, 1H), 1.46-1.63(m, 2H), 1.20(d, 3H), 0.89(t, 3H), 0.77(dd, 6H) |

TABLE 5-continued

| No. | $^1$H-NMR[CDCl$_3$/TMS, δ value (ppm)] |
|---|---|
| 1-426 | 7.42(d, 1H), 7.10(m, 2H), 5.43(s, H), 4.14(q, 2H), 3.58(s, 3H), 3.44(s, 3H), 2.80(d, 2H), 2.05(s, 3H), 2.01(s, 3H), 1.85(m, 1H), 0.76(d, 6H) |
| 1-427 | 7.40(d, 1H), 7.17(dd, 1H), 7.13(d, 1H), 5.87-5.98(m, 1H), 5.32(s, 2H), 5.29(d, 1H), 5.20(dd, 1H), 4.16(d, 2H), 3.59(s, 3H), 3.44(s, 3H), 2.80(d, 2H), 2.09(s, 3H), 2.04(s, 3H), 1.87(m, 1H), 0.76(d, 6H) |
| 1-428 | 7.39(d, 1H), 7.15(m, 1H), 5.30(s, 2H), 3.60(t, 2H), 3.59(s, 3H), 3.43(s, 3H), 2.80(d, 2H), 2.09(s, 3H), 2.04(s, 3H), 1.88(m, 1H), 1.60(m, 2H), 1.27(m, 10H), 0.88(t, 3H), 0.77(d, 6H) |
| 1-429 | 7.49(d, 1H), 7.12(d, 1H), 7.08(dd, 1H), 3.68(s, 3H), 3.46(m, 1H), 3.46(s, 3H), 2.88(d, 2H), 2.40(m, 2H), 2.35(s, 3H), 2.25(s, 3H), 1.84-2.11(m, 5H), 0.80(d, 6H) |
| 1-448 | 7.49(d, 1H), 7.06(d, 1H), 6.98(m, 1H), 3.64(s, 3H), 3.47(s, 3H), 2.86(d, 2H), 2.39(s, 3H), 1.95(m, 1H), 1.38(s, 9H), 0.76(d, 6H) |
| 1-452 | 7.49(d, 1H), 7.18(d, 1H), 7.13(m, 1H), 4.31(s, 2H), 3.71(s, 3H), 3.46(s, 3H), 3.42(s, 3H), 2.88(d, 2H), 2.32(s, 3H), 2.03(m, 1H), 0.79(d, 6H) |
| 1-514 | 7.53(d, 1H), 7.27(d, 1H), 7.16(dd, 1H), 3.72(s, 3H), 3.48(s, 3H), 2.92(d, 2H), 2.88(m, 1H), 2.43(s, 3H), 2.07(m, 1H), 1.21(d, 6H), 0.84(d, 6H) |
| 1-515 | 7.41(d, 1H), 7.21(d, 1H), 7.19(d, 1H), 5.28(s, 2H), 3.92(m, 1H), 3.63(s, 3H), 3.44(s, 3H), 2.82(d, 2H), 2.19(s, 3H), 1.94(m, 1H), 1.21(d, 6H), 0.79(d, 6H) |
| 1-516 | 7.55(d, 1H), 7.32(d, 1H), 7.16(dd, 1H), 3.79(s, 3H), 3.76(s, 3H), 3.49(s, 3H), 2.94(d, 2H), 2.47(s, 3H), 2.14(m, 1H), 0.92(d, 6H) |
| 1-518 | 7.53(d, 1H), 7.28(d, 1H), 7.18(dd, 1H), 3.74(s, 3H), 3.47(s, 3H), 2.92(m, 1H), 2.91(d, 2H), 2.42(s, 3H), 2.07(m, 1H), 1.23(d, 6H), 0.84(d, 6H) |
| 1-519 | 7.42(d, 1H), 7.22(d, 1H), 7.21(s, 1H), 5.28(s, 2H), 3.94(m, 1H), 3.63(s, 3H), 3.44(s, 3H), 2.82(d, 2H), 2.14(s, 3H), 1.95(m, 1H), 1.21(d, 6H), 0.79(d, 6H) |
| 1-521 | 7.56(d, 1H), 7.35(d, 1H), 7.19(dd, 1H), 3.81(s, 3H), 3.76(s, 3H), 3.50(s, 3H), 2.94(d, 2H), 2.47(s, 3H), 2.14(m, 1H), 0.92(d, 6H) |
| 1-522 | 8.17(br, 1H), 7.78(d, 1H), 7.47-7.53(m, 2H), 3.84(s, 3H), 3.47(s, 3H), 2.93(d, 2H), 2.62(s, 3H), 2.24(m, 1H), 0.95(d, 6H) |
| 1-523 | 7.57(d, 1H), 7.39(d, 1H), 7.22(dd, 1H), 3.84(s, 3H), 3.76(s, 3H), 3.50(s, 3H), 2.95(d, 2H), 2.46(s, 3H), 2.15(m, 1H), 0.92(d, 6H) |
| 1-524 | 7.51(d, 1H), 7.27(d, 1H), 7.20(dd, 1H), 3.74(s, 3H), 3.46(s, 3H), 2.99(m, 1H), 2.90(d, 2H), 2.37(s, 3H), 2.07(m, 1H), 1.26(d, 6H), 0.82(d, 6H) |
| 1-539 | 7.55(d, 1H), 7.16(d, 1H), 7.11(dd, 1H), 6.87(s, 1H), 3.73(s, 3H), 3.48(s, 3H), 3.31(m, 1H), 2.89(d, 2H), 2.04(m, 1H), 1.27(d, 6H), 0.79(d, 6H) |
| 1-540 | 7.55(d, 1H), 7.20(d, 1H), 7.12(dd, 1H), 7.05(s, 1H), 3.72(s, 3H), 3.49(s, 3H), 3.22(m, 1H), 2.90(d, 2H), 2.05(m, 1H), 1.26(d, 6H), 0.81(d, 6H) |
| 1-541 | 7.56(d, 1H), 7.21(d, 1H), 7.15(s, 1H), 7.12(dd, 1H), 3.72(s, 3H), 3.49(s, 3H), 3.17(m, 1H), 2.91(d, 2H), 2.05(m, 1H), 1.25(d, 6H), 0.82(d, 6H) |
| 1-542 | 7.57(d, 1H), 7.17(d, 1H), 7.09(dd, 1H), 7.06(s, 1H), 3.78(s, 3H), 3.49(s, 3H), 3.26(m, 1H), 2.90(d, 2H), 2.03(m, 1H), 1.24(d, 6H), 0.78(d, 6H) |
| 1-544 | 7.51(d, 1H), 7.16(m, 1H), 6.97(d, 1H), 3.82(s, 3H), 3.65(s, 3H), 2.63(t, 2H), 2.27(s, 3H), 2.24(s, 3H), 2.10(s, 3H), 2.00(s, 3H), 1.67(m, 1H), 0.81(d, 6H) |
| 1-545 | 7.47(d, 1H), 7.34(d, 1H), 7.11(m, 1H), 6.94(d, 1H), 6.86(d, 1H), 3.67(s, 3H), 2.60(t, 2H), 2.51(s, 3H), 2.38(s, 3H), 2.28(s, 3H), 1.73(m, 1H), 0.75(d, 6H) |
| 2-28 | 7.62(s, 1H), 7.25(s, 1H), 3.71(s, 3H), 3.50(s, 3H), 2.88(d, 2H), 2.38(s, 3H), 2.32(s, 3H), 2.24(s, 3H), 2.02(m, 1H), 0.85(d, 6H) |
| 2-38 | 7.41(s, 1H), 7.12(s, 1H), 3.72(s, 3H), 3.48(s, 3H), 2.88(d, 2H), 2.38(s, 3H), 2.30(s, 3H), 2.24(s, 3H), 2.40-2.30(m, 2H), 2.04(m, 1H), 1.14(t, 3H), 0.85(d, 6H) |
| 2-40 | 8.26(s, 1H), 7.82(s, 1H), 7.27(br, 2H), 3.90(s, 3H), 3.45(s, 3H), 2.95(m, 2H), 2.57(s, 3H), 2.32(s, 3H), 1.71(m, 2H), 1.02(t, 3H) |
| 2-41 | 7.37(s, 1H), 7.10(s, 1H), 6.30(s, 1H), 3.59(s, 3H), 3.47(s, 3H), 3.43(m, 2H), 2.92(br, 2H), 2.48(s, 3H), 2.17(s, 3H), 1.55(br, 2H), 1.28(d, 6H), 0.94(t, 3H) |

The agrohorticultural agent, in particular, agrohorticultural insecticides or acaricides, containing a substituted pyrazolecarboxanilide derivative represented by the formula (I) or salt of the present invention as an active ingredient, are suitable for controlling various insect pests such as agrohorticultural insect pests, stored grain insect pests, sanitary insect pests, nematodes, etc., which are injurious to paddy rice, fruit trees, vegetables, other crops, flowers and ornamental plants, etc. They have a marked insecticidal effect, for example, on LEPIDOPTERA including summer fruit tortrix (*Adoxophes orana fasciata*), smaller tea tortrix (*Adoxophyes* sp.), Manchurian fruit moth (*Grapholita inopinata*), oriental fruit moth (*Grapholita molesta*), soybean pod borer (*Leguminivora glycinivorella*), mulberry leafroller (*Olethreutes mori*), tea leafroller (*Caloptilia thevivora*), *Caloptilia* sp. (*Caloptilia zachrysa*), apple leafminer (*Phyllonorycter ringoniella*), pear barkminer (*Spulerrina astaurota*), common white (*Piers rapae crucivora*), tobacco budworm (*Heliothis* sp.), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.;

HEMIPTERA including aster leafhopper (*Macrosteles fascifrons*), green rice leafhopper (*Nephotettix cincticepts*), brown rice planthopper (*Nilaparvata lugens*), whitebacked rice planthopper (*Sogatella furcifera*), citrus psylla (*Diaphorina citri*), grape whitefly (*Aleurolibus taonabae*), sweetpotato whitefly (*Bemisia tabaci*), greenhouse whitefly (*Trialeurodes vaporariorum*), turnup aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unaspis yanonensis*), etc.;

TYLENCHIDA including soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc.;

DIPTERA including melon fly (*Dacus (Zeugodacus) cucurbitae*), oriental fruit fly (*Dacus (Bactrocera) dorsalis*), rice leafminer (*Agnomyza oryzae*), onion maggot (*Delia antiqua*), seedcorn maggot (*Delia platura*), soybean pod gall midge (*Asphondylia* sp.), etc.; TYLENCHIDA including root-lesion nematode (*Pratylenchus* sp.), potato cyst nematode (*Globodera rostochiensis*), root-knot nematode (*Meloidogyne* sp.), citrus nematode (*Tylenchulus semipenetrans*), *Aphelenchus* sp. (*Aphelenchus avenae*), chrysanthemum foliar (*Aphelenchoides ritzemabosi*), etc.; and ACARINA including citrus red mite (*Panonychus citri*), fruit tree red spider mite (*Panonychus ulmi*), carmine spider mite (*Tetranychus cinnabarinus*), Kanzawa spider mite (*Tetranychus Kanzawai* Kishida), two-spotted spider mite (*Tetranychus urticae* Koch), pink tea rust mite (*Acaphylla theae*), pink citrus rust mite (*Aculops pelekassi*), purple tea mice (*Calacarus carinatus*), pear rust mite (*Epitrimerus pyri*), etc.

A substituted pyrazolecarboxanilide derivative represented by the formula (I) or salts thereof of the present invention is used preferably as agrohorticultural insecticides or acaricides. However, the compound exhibits excellent control effect against various insect pests such as insect pests for forest and wood, insect pests for livestock farming, sanitary insect pests, etc. and can be used as pest control agents in various wide fields. Examples of insect pests include: Tabanidae such as *Tabanus rufidens* Bigot; Muscidae such as housefly (*Musca domestica* uicina MACQUART); Gasterophilidae such as horse bot fly (*Gasterophilus intestinalis*); Hypodermatidae such as cattle grub (*Hypoderma bovis* L.); Phoridae such as *Megaselia spiracularis*; Culicidae such as pale house mosquito (*Culex pipiens* pallens), *Anopheles sinensis*, one-striped mosquito (*Aedes albopictus*), and *Aedes japonicus*; Pulicidae such as cat flea (*Ctenocephalides felis*), dog flea (*Ctenocephalides canis*), human flea (*Pulex irritans*); Ixodidae such as *Ixodes ovatus* Neumann; Lymantriidae such as *Euproctis similes*; Rhynchophoridae such as rice weevil (*Sitophilus zeamais*); Vespidae such as *Vespa simillima* xanthoptera Cameron; Blattellidae such as German cockroach (*Blattela germanica*); Blattidae such as American cockroach (*Periplaneta americana*) and *Periplaneta japonica*; Pthiridae such as public-louse (*Phthirus pubis*); Termitidae such as Japanese termite (*Reticulitermes speratus*) and house termite (*Coptotermes formosanus*); and Ixodidae such as *Ixodes persulcatus*; and Macronyssidae such as tropical rat mite (*Ornithonyssus bacoti*).

The agrohorticultural agent, in particular, agrohorticultural insecticides or acaricides, containing a substituted pyrazolecarboxanilide derivative represented by the formula (I) or salt thereof of the present invention as an active ingredient has a marked controlling effect on the above-exemplified insect pests, which are injurious to paddy field crops, upland crops, fruit trees, vegetables and other crops, flowers and ornament plants, and the like. Therefore, the desired effect of the agrohorticultural insecticides of the present invention can be exhibited by applying the agents to paddy field, field, fruit trees, vegetables, other crops, seeds of flowers and ornament plants, paddy field water, stalks and leaves, or soil at a season at which the insect pests are expected to appear, before their appearance or at the time when their appearance is confirmed.

Plants, for which an agrohorticultural agent of the present invention can be used, are not specifically limited and include, for example, plants shown hereinbelow:

Cereals (e.g. rice (*Oryza sativa*), barley (*Hordeum vulgare*), wheat (*Triticum aestivum* L.), rye (*Secale cereale*), oat (*Avena*), maize (*Zea mays* L.), kaoliang, etc.); legume (soybean, adzuki bean, fava bean, bean, peanut, etc.); fruit trees and fruits (apple, citrus fruits, pear, grapes, peach, plum, cherry, walnut, almond, banana, strawberry, etc.); vegetables (cabbage, tomato, spinach, broccoli, lettuce, onion, welsh onion, green pepper, etc.); root vegetables (carrot, potato, sweet potato, radish, lotus root, turnip, etc.); crop for processing (cotton, flax (*Linum usitatissimum*), paper mulberry (*Broussonetia kasinoki* SIEB), paperbush (*Edgeworthia papyrifera*), rape (*Brassica napus* L.), beet (*Beta vulgaris*), hop, sugar cane (*Saccharum officinarum*), sugar beet (*Beta vulgaris* var. *saccharifera*), olive, rubber, coffee, tobacco, tea, etc.); gourd (pumpkin, cucumber, watermelon, melon, etc.); grass (orchard grass, sorghum, timothy, clover, alfalfa, etc.); grass (Korean lawn grass, bent grass, etc.); crop for spicery (lavender (*Lavandula officinalis* CHAIX), rosemary, thyme, parsley, pepper, ginger, etc.); and flowers (chrysanthemum, rose, orchid, etc.).

Recently, gene recombinant crop (herbicide resistant crop, insect pest resistant crop incorporated with insecticidal toxin generating gene, disease resistant crop incorporated with disease resistance inducer producing gene, taste improved crop, preservability improved crop, yield improved crop, etc.), insect sex pheromone (pheromone disrupting chemicals for leaf roller moths, cabbage armyworm, etc.), IPM (integrated pest management) technology using natural enemy insect have been progressed, and pesticide compositions of the present invention can be used in combination with or by systematization with such technologies.

The agrohorticultural agent of the present invention is generally prepared into conveniently usable forms according to an ordinary manner for formulation of agrochemicals.

That is, the substituted pyrazolecarboxanilide derivative represented by the formula (I) or salt of the present invention and, optionally, an adjuvant are blended with a suitable inert carrier in a proper proportion and prepared into a suitable formulation form such as a suspension, emulsifiable concentrate, soluble concentrate, wettable powder, water dispersible granule, granules, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, resins such as powdered synthetic polymers and the like, clays (e.g. kaolin, bentonite, and acid clay), talcs (e.g. talc and pyrophyllite), silica powders or flakes (e.g. diatomaceous earth, silica sand, mica and white carbon [synthetic, high-dispersion silicic acid, also called finely divided hydrated silica or hydrated silicic acid, some of commercially available products contain calcium silicate as the major component]), inorganic or mineral powders such as activated carbon, powdered sulfur, pumice, calcined diatomaceous earth, ground brick, fly ash, sand, calcium carbonate, calcium phosphate and the like, plastic carriers such as polyethylene, polypropylene, poly(vinylidene chloride) and the like, chemical fertilizers (e.g. ammonium sulfate, ammonium phosphate, ammonium nitrate, urea and ammonium chloride), and compost. These carriers may be used alone or as a mixture of two or more kinds thereof.

A material usable as the liquid carrier is selected from materials that have solubility in themselves or which, even without such solubility, are capable of dispersing an active ingredient with the aid of an adjuvant. The following are typical examples of the liquid carrier and can be used alone or as a mixture of two or more kinds thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbons (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination of two or more kinds, or in some cases, need not be used at all.

To emulsify, disperse, dissolve and/or wet a compound as active ingredient, a surfactant is used. As the surfactant, there can be exemplified polyoxyethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates and higher alcohol sulfate esters.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly(vinyl alcohol)s, turpentine, bran oil, bentonite and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products Adjuvants such as silicone oils may also be used as a defoaming agent.

Adjuvants such as 1,2-benzisothiazoline-3-one, p-chlorom-xylenol, butyl p-hydroxybenzoate may also be added as a preservative.

Further, if necessary, functional spreading agents, active enhancers such as metabolic decomposition inhibitor like piperonyl butoxide, anti-freezing agents such as propylene glycol, antioxidants such as BHT, ultraviolet absorbers, and the other additives may also be added.

The content of the compound as active ingredient may be varied as required, and the compound as active ingredient may be used in a proportion properly chosen in the range of 0.01 to 90 parts by weight per 100 parts of the agrohorticultural agents. For example, in dusts or granules, the suitable content of the compound as active ingredient is from 0.01 to 50% by weight. In emulsifiable concentrate or wettable powders, it is also from 0.01 to 50% by weight.

The agrohorticultural agent of the present invention is used to control a variety of insect pests in the following manner: it is applied to a crop on which the insect pests are expected to appear, or a site where appearance or growth of the insect pests is undesirable, as it is or after being properly diluted with or suspended in water or the like, in an amount effective for control of the insect pests.

The applying dosage of the agrohorticultural agent of the present invention is varied depending upon various factors such as a purpose, insect pests to be controlled, a growth state of a plant, tendency of insect pests appearance, weather, environmental conditions, a formulation form, an application method, an application site and application time. It may be properly chosen in the range of 0.001 g to 10 kg, preferably 0.01 g to 1 kg, (in terms of the compound as active ingredient) per 10 acres depending upon purposes.

The agrohorticultural agent of the present invention may be used in admixture with other agrohorticultural insecticides, acaricides, nematocides, fungicides, biotic pesticides or the like in order to expand both spectrum of controllable insect pest species and the period of time when effective application are possible or to reduce the dosage. Furthermore, the agrohorticultural insecticide of the present invention may be used in admixture with herbicides, plant growth regulators, fertilizers or the like, depending upon application situations.

As the other agrohorticultural insecticides, acaricides and nematocides, which are used for the above purpose, there can be exemplified agrohorticultural insecticides, acaricides and nematocides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylparathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, Spirodiclofen, Metaflumizone, Flubendiamide, DPS (NK-0795), Phosphocarb, Fenamiphos, Isoamidophos, Fosthiazate, Isazophos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Cycloprothrin, Ethofenprox, Halfenprox, Silafluofen, Flucythrinate, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, BPMC, Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatin oxide, Tricyclohexyltin hydroxide, Sodium oleate, Potassium oleate, Methoprene, Hydroprene, Binapacryl, Amitraz, Dicofol, Kersen, Chlorobenzilate, Bromopropylate, Tetradifon, Bensultap, Benzoximate, Tebufenozide, Methoxyfenozide, Pyridalyl, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, Nicotine sulfate, Nitenpyram, Acetamiprid, Thiacloprid, Imidacloprid, Thiamethoxam, Clothianidin, Dinotefuran, Fluazinam, Pyriproxyfen, Hydramethylnon, Pyrimidifen, Pyridaben, Cyromazine, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (Bacillus thuringiensis), Azadirachtin, Rotenone, Hydroxypropyl starch, Levamisole hydrochloride, Metam-sodium, Morantel tartrate, Dazomet, Trichlamide, Pasteuria penetrans, Monacrosporium-phymatophagum, etc.

As the agrohorticultural fungicides used for the same purpose as above, there can be exemplified agrohorticultural fungicides such as Sulfur, Lime sulfur, Copper sulfate basic, Iprobenfos, Edifenfos, Tolclofos-methyl, Thiram, Polycarbamate, Zineb, Maneb, Mancozeb, Propineb, Thiophanate, Thiophanate methyl, Benomyl, Iminoctadin acetate, Iminocutadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil, Himexazol, Etridiazol, Fluoroimide, Procymidone, Vinclozolin, Iprodione, Triadimefon, Bitertanol, Triflumizole, Ipconazole, Fluconazole, Propiconazole, Diphenoconazole, Myclobutanil, Tetraconazole, Hexaconazole, Tebuconazole, Thiadinil, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Thiadiazin, Captan, Probenazole, Acibenzolar-S-methyl, Fthalide, Tricyclazole, Pyroquilon, Chinomethionat, Oxolinic acid, Dithianon, Kasugamycin, Validamycin, Polyoxin, Blasticidin, Streptomycin, etc.

Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linuron, Dymron, Isouron, Bensulfuron methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benflesate, Flutiacet-methyl, Quizalofop-ethyl, Bentazon, Calcium peroxide, etc.

As to the biotic pesticides, the same effect as above can be expected by using the agrohorticultural agent of the present invention in admixture with, for example, viral formulations obtained from nuclear polyhedrosis virus (NPV), granulosis virus (GV), cytoplasmic polyhedrosis virus (CPV), entomopox virus (EPV), etc.; microbial pesticides utilized as insecticides or nematicides, such as *Monacrosporium phymatophagum, Steinernema carpocapsae, Steinernema kushidai, Pasteuria penetrans*, etc.; microbial pesticides utilized as fungicides, such as *Trichoderma lignorum, Agrobacterium radiobactor*, nonpathogenic *Erwinia carotovora, Bacillus subtilis*, etc.; and biotic pesticides utilized as herbicides, such as *Xanthomonas campestris*, etc.

In addition, the agrohorticultural agent of the present invention can be used in combination with biotic pesticides including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial pesticides such as *Beauveria brongniartii*, etc.; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one, 14-methyl-1-octadecene, etc.

EXAMPLES

The substituted pyrazolecarboxanilide derivatives represented by the formula (I), and substituted aniline derivative represented by the formula (II) and substituted pyrazolecarboxic acid represented by the formula (IV), which are intermediates therefore, of the present invention, are explained in the following by referring to Examples, which are not to be construed as limitative.

Example 1

Production of 1,3-dimethyl-5-trifluoromethylpyrazole-4-carboxylic Acid (Compound No. 4-1)

4-Iodo-1,3-dimethyl-5-trifluoromethylpyrazole (8.7 g, 30 mmol) was dissolved in tetrahydrofuran (87 ml), and a solution (1.6 M, 28 ml) of n-butyl lithium in hexane was slowly added under an argon atmosphere with cooling with dryice-acetone (not higher than −60° C.). After stirring at −70° C. for 30 min, the mixture was gradually warmed to room temperature while blowing in carbon dioxide. The reaction mixture was poured into water, the organic layer was removed, and the aqueous layer was acidified with hydrochloric acid. The aqueous layer was extracted with ethyl acetate. The organic layer was washed with water, dried over magnesium sulfate and concentrated under reduced pressure. The obtained crude crystals were washed with hexane to give the desired compound (4.67 g) as crystals.
yield 74%
Property: melting point 124-125.5° C.

Example 2

Production of N-{3-isobutyl-4-[1-methoxy-2,2,2-trifluoro-1-(trifluoromethyl)ethyl]phenyl}-1,5-dimethyl-3-trifluoromethylpyrazole-4-carboxamide (Compound No. 1-211)

1,5-Dimethyl-3-trifluoromethylpyrazole-4-carboxylic acid (2.09 g, 10 mmol) was dissolved in thionyl chloride, and the mixture was heated under reflux for 3 hr. The mixture was concentrated under reduced pressure to give 1,5-dimethyl-3-trifluoromethylpyrazole-4-carbonyl chloride. This was added to a solution of 3-isobutyl-4-[1-methoxy-2,2,2-trifluoro-1-(trifluoromethyl)ethyl]aniline (3.29 g, 10 mmol) and triethylamine (3.03 g, 30 mmol) in tetrahydrofuran (30 ml), and the mixture was heated under reflux for 2 hr. The reaction mixture was diluted with ethyl acetate, washed with water, and dried over magnesium sulfate. After concentration under reduced pressure, the obtained residue was purified by silica gel column chromatography (hexane:ethyl acetate=1:1) to give the desired compound (3.64 g) as crystals.
yield 70%
Property: melting point 138-139° C.

Example 3

Production of N-methoxymethyl-N-{3-isobutyl-4-[1-methoxy-2,2,2-trifluoro-1-(trifluoromethyl)ethyl]phenyl}-1,5-dimethyl-3-trifluoromethylpyrazole-4-carboxamide (Compound No. 1-222)

Sodium hydride (32 mg, 60%, 0.8 mmol) was suspended in tetrahydrofuran (10 ml), and a solution of N-{3-isobutyl-4-[1-methoxy-2,2,2-trifluoro-1-(trifluoromethyl)ethyl]phenyl}-1,5-dimethyl-3-trifluoromethylpyrazole-4-carboxamide (250 mg, 0.48 mmol) in tetrahydrofuran (5 ml) was added dropwise. After stirring at room temperature for 30 min, a solution of chloromethyl methyl ether (64 mg, 0.8 mmol) in tetrahydrofuran (2 ml) was added and the mixture was stirred for 5 hr. The reaction mixture was poured into diluted hydrochloric acid and extracted with ethyl acetate. The organic layer was washed with water, dried over magnesium sulfate, and concentrated under reduced pressure, and the obtained residue was purified by silica gel column chromatography (hexane:ethyl acetate=2:1) to give the desired compound (238 mg).
yield: 88%
Property: $n_D$1.4669 (22.4° C.)

Example 4

Production of 2-methyl-5-n-propyl-4-[1,2,2,2-tetrafluoro-1-(trifluoromethyl)ethyl]aniline (Compound No. 3-1)

5-n-Propyl-2-methylaniline (14.9 g, 0.1 mol) was diluted in a mixed solvent (300 ml) of tert-butyl methyl ether-water (1:1), and heptafluoroisopropyl iodide (29.6 g, 0.1 mol), tetrabutylammonium hydrogen sulfate (3.4 g, 0.01 mol), sodium hydrogen carbonate (8.4 g, 0.1 mol) and sodium dithionite (17 g, 0.1 mol) were successively added. The mixture was stirred overnight at room temperature. The reaction mixture was diluted in hexane, washed twice with 3N hydrochloric acid, and washed with aqueous sodium hydrogen carbonate and saturated brine. The organic layer was dried over magnesium sulfate, and concentrated under reduced pressure. The residue was purified by silica gel chromatography (hexane:ethyl acetate 5:1) to give the desired compound (28.5 g).
yield: 90%
Property: $^1$H-NMR [CDCl$_3$/TMS, δ value (ppm)] 7.09 (s, 1H), 6.54 (s, 1H), 3.76 (bs, 2H), 2.63 (m, 2H), 2.13 (s, 3H), 1.58 (m, 2H), 0.96 (t, 3H)

Example 5

Production of 4-[1-methoxy-2,2,2-trifluoro-1-(trifluoromethyl)ethyl]-2-methyl-5-n-propylaniline (Compound No. 3-3)

2-Methyl-5-n-propyl-4-[1,2,2,2-tetrafluoro-1-(trifluoromethyl)ethyl]aniline (1.6 g, 5 mmol) was dissolved in a 28% solution (9.6 g) of sodium methoxide in methanol, and the mixture was heated under reflux for 3 hr. After allowing to cool, the reaction mixture was poured into ice water and extracted with ethyl acetate. The organic layer was washed with water, dried over magnesium sulfate and concentrated under reduced pressure. The obtained residue was purified by silica gel column chromatography (hexane:ethyl acetate=5:1) to give the desired compound (1.31 g).
yield: 79%
Property: $^1$H-NMR [CDCl$_3$/TMS, δ value (ppm)] 7.10 (s, 1H), 6.66 (s, 1H), 3.72 (bs, 2H), 3.42 (s, 3H), 2.84 (m, 2H), 2.14 (s, 3H), 1.61 (m, 2H), 1.00 (t, 3H)

Example 6

Production of 2-methyl-5-n-propyl-4-[2,2,2-trifluoro-1-(trifluoromethyl)ethyl]aniline (Compound No. 3-2)

2-Methyl-5-n-propyl-4-[1,2,2,2-tetrafluoro-1-(trifluoromethyl)ethyl]aniline (1.6 g, 5 mmol) was dissolved in dimethyl sulfoxide (20 ml), sodium borohydride (378 mg, 10 mmol) was added by small portions, and the mixture was stirred at 60° C. for 5 hr. Ice was added to the reaction mixture by small portions, and then acetic acid was added dropwise. The reaction mixture was diluted with ethyl acetate, and the organic layer was washed 4 times with water, dried over magnesium sulfate and concentrated under reduced pressure to give the desired compound (1.47 g).
yield: 99%
Property: $^1$H-NMR [CDCl$_3$/TMS, δ value (ppm)] 7.18 (s, 1H), 6.54 (s, 1H), 4.45-4.20 (br, 2H), 4.27 (m, 1H), 2.50 (dd, 2H), 2.14 (s, 3H), 1.57 (m, 2H), 0.98 (t, 3H)

Example 7

Production of N-{4-[1-methoxy-2,2,2-trifluoro-1-(trifluoromethyl)ethyl]-2-methyl-5-n-propylphenyl}-1,3,5-trimethylpyrazole-4-carboxamide (compound No. 2-15)

1,3,5-Trimethylpyrazole-4-carbonyl chloride (172 mg, 1 mmol), 4-[1-methoxy-2,2,2-trifluoro-1-(trifluoromethyl)ethyl]-2-methyl-5-n-propylaniline (329 mg, 1 mmol) and triethylamine (303 mg, 3 mmol) were dissolved in tetrahydrofuran (10 ml), and the mixture was heated under reflux for 3 hr. The reaction mixture was diluted with ethyl acetate, and washed with water. The organic layer was dried over anhydrous magnesium sulfate and concentrated under reduced pressure. The obtained residue was purified by silica gel column chromatography (hexane:ethyl acetate=1:2) to give the desired compound (360 mg).
yield: 77%
Property: melting point 132-134° C.

Example 8

Production of N-acetyl-N-{4-[1-methoxy-2,2,2-trifluoro-1-(trifluoromethyl)ethyl]-2-methyl-5-n-propylphenyl}-1,3,5-trimethylpyrazole-4-carboxamide (Compound No. 2-16)

Sodium hydride (32 mg, 60%, 0.8 mmol) was suspended in tetrahydrofuran (10 ml), and a solution of N-{4-[1-methoxy-2,2,2-trifluoro-1-(trifluoromethyl)ethyl]-2-methyl-5-n-propylphenyl}-1,3,5-trimethylpyrazole-4-carboxamide (250 mg, 0.53 mmol) in tetrahydrofuran (5 ml) was added dropwise. After stirring at room temperature for 30 min, a solution of acetic anhydride (80 mg, 0.78 mmol) in tetrahydrofuran (2 ml) was added, and the mixture was stirred for one day. The reaction mixture was poured into diluted hydrochloric acid, and the mixture was extracted with ethyl acetate. The organic layer was washed with water, dried over magnesium sulfate and concentrated under reduced pressure, and the obtained residue was purified by silica gel column chromatography (hexane:ethyl acetate=1:3) to give the desired compound (139 mg).
yield: 52%
Property: $n_D$1.4905 (25.9° C.)

Example 9

Production of N-{2-methyl-5-n-propyl-4-[2,2,2-trifluoro-1-(trifluoromethyl)ethyl]phenyl-2-methyl-5-n-propylphenyl}-1,3,5-trimethylpyrazole-4-carboxamide (Compound No. 2-13)

In the same manner as in Example 7 except that 2-methyl-5-n-propyl-4-[2,2,2-trifluoro-1-(trifluoromethyl)ethyl]aniline was used instead of 4-[1-methoxy-2,2,2-trifluoro-1-(trifluoromethyl)ethyl]-2-methyl-5-n-propylaniline, the reaction is carried out for 3 hr to give the desired compound.
yield: 66%
Property: melting point 128-131° C.

Example 10

Production of N-{3-isobutyl-4-[1-methoxy-2,2,2-trifluoro-1-(trifluoromethyl)ethyl]phenyl}-1,3,5-trimethylpyrazole-4-carboxamide (Compound No. 1-155)

1,3,5-trimethylpyrazole-4-carbonyl chloride (3.93 g, 22.8 mmol), 3-isobutyl-4-[1-methoxy-2,2,2-trifluoro-1-(trifluoromethyl)ethyl]aniline (5.0 g, 15.2 mmol), and triethylamine (3.07 g, 30.4 mmol) were dissolved in tetrahydrofuran (100 ml), and the mixture was heated under reflux for 5 hr. The reaction mixture was diluted with ethyl acetate, and washed with water. The organic layer was dried over anhydrous magnesium sulfate and concentrated under reduced pressure. The obtained crude crystals were washed with ether to give the desired compound (5.62 g).
yield: 80%
Property: melting point 189-190° C.

Example 11

Production of N-ethoxymethyl-N-{3-isobutyl-4-[1-methoxy-2,2,2-trifluoro-1-(trifluoromethyl)ethyl]phenyl}-1,3,5-trimethylpyrazole-4-carboxamide (Compound No. 1-145)

Sodium hydride (29 mg, 60%, 0.73 mmol) was suspended in tetrahydrofuran (10 ml), and a solution of N-{3-isobutyl-4-[1-methoxy-2,2,2-trifluoro-1-(trifluoromethyl)ethyl]phenyl}-1,3,5-trimethylpyrazole-4-carboxamide (260 mg, 0.48 mmol) in tetrahydrofuran (5 ml) was added dropwise. After stirring at room temperature for 30 min, a solution of chloromethyl ethyl ether (70 mg, 0.73 mmol) in tetrahydrofuran (2 ml) was added, and the mixture was stirred for one day. The reaction mixture was poured into diluted hydrochloric acid, and the mixture was extracted with ethyl acetate. The organic layer was washed with water, dried over magnesium sulfate and concentrated under reduced pressure, and the obtained residue was purified by silica gel column chromatography (hexane:ethyl acetate=1:3) to give the desired compound (200 mg).

yield: 69%
Property: $n_D$1.4892 (22.4° C.)

Example 12

Production of N-isobutyloxycarbonyl-N-{3-isobutyl-4-[1-methoxy-2,2,2-trifluoro-1-(trifluoromethyl)ethyl]phenyl}-1,3,5-trimethylpyrazole-4-carboxamide (Compound No. 1-152)

Sodium hydride (29 mg, 60%, 0.73 mmol) was suspended in tetrahydrofuran (10 ml), and a solution of N-{3-isobutyl-4-[1-methoxy-2,2,2-trifluoro-1-(trifluoromethyl)ethyl]phenyl}-1,3,5-trimethylpyrazole-4-carboxamide (260 mg, 0.48 mmol) in tetrahydrofuran (5 ml) was added dropwise. After stirring at room temperature for 30 min, a solution of isobutyl chlorocarbonate (100 mg, 0.73 mmol) in tetrahydrofuran (2 ml) was added, and the mixture was stirred for one day. The reaction mixture was poured into diluted hydrochloric acid and extracted with ethyl acetate. The organic layer was washed with water, dried over magnesium sulfate and concentrated under reduced pressure, and the obtained residue was purified by silica gel column chromatography (hexane:ethyl acetate=1:1) to give the desired compound (280 mg).

yield: 91%
Property: $n_D$1.4829 (22.3° C.)

Example 13

Production of N-{3-isobutyl-4-[2,2,2-trifluoro-1-(trifluoromethyl)ethyl]phenyl}-1,3,5-trimethylpyrazole-4-carboxamide (Compound No. 1-123)

1,3,5-Trimethylpyrazole-4-carbonyl chloride (2.09 g, 10.0 mmol), 3-isobutyl-4-[2,2,2-trifluoro-1-(trifluoromethyl)ethyl]aniline (2.0 g, 6.69 mmol), and triethylamine (1.35 g, 13.4 mmol) were dissolved in tetrahydrofuran (60 ml), and the mixture was heated under reflux for 5 hr. The reaction mixture was diluted with ethyl acetate, and washed with water. The organic layer was dried over anhydrous magnesium sulfate and concentrated under reduced pressure, and the obtained residue was purified by silica gel column chromatography (hexane:ethyl acetate=1:3) to give the desired compound (2.41 g).

yield: 77%
Property: melting point 148-151° C.

Example 14

Production of N-acetyl-N-{3-isobutyl-4-[2,2,2-trifluoro-1-(trifluoromethyl)ethyl]phenyl}-1,3,5-trimethylpyrazole-4-carboxamide (Compound No. 1-125)

Sodium hydride (38 mg, 60%, 0.96 mmol) was suspended in tetrahydrofuran (10 ml), and a solution of N-{3-isobutyl-4-[2,2,2-trifluoro-1-(trifluoromethyl)ethyl]phenyl}-1,3,5-trimethylpyrazole-4-carboxamide (300 mg, 0.64 mmol) in tetrahydrofuran (5 ml) was added dropwise. After stirring at room temperature for 30 min, a solution of acetyl chloride (75 mg, 0.96 mmol) in tetrahydrofuran (2 ml) was added, and the mixture was stirred for one day. The reaction mixture was poured into diluted hydrochloric acid and extracted with ethyl acetate. The organic layer was washed with water, dried over magnesium sulfate and concentrated under reduced pressure, and the obtained residue was purified by silica gel column chromatography (hexane:ethyl acetate=1:3) to give the desired compound (90 mg).

yield: 28%
Property: $n_D$1.5021 (22.5° C.)

Reference Example

Production of 1
4-iodo-1,3-dimethyl-5-trifluoromethylpyrazole

Iodine (30 g) was dissolved in 60% sulfuric acid (fuming, 80 g), and 1,3-dimethyl-5-trifluoromethylpyrazole (13.12 g, 80 mmol) was slowly added under ice-cooling. The mixture was stirred at 0° C. for 2 hr. The reaction mixture was poured into ice water and extracted with ethyl acetate. The organic layer was washed with aqueous sodium thiosulfate and saturated brine, dried over magnesium sulfate and concentrated under reduced pressure. The obtained crude crystals were washed with hexane to give the desired compound (20 g) as crystals.

yield 86%
Property: $^1$H-NMR [CDCl$_3$/TMS, δ value (ppm)] 3.98 (s, 3H), 2.26 (s, 3H)

Typical formulation examples and test example of the present invention are described below but they should not be construed as limiting the scope of the invention.

As used in the examples, the terms "part" and "parts" are by weight.

Formulation Example 1

| | |
|---|---|
| Each compound listed in Table 1 or Table 2 | 10 parts |
| Xylene | 70 parts |
| N-methylpyrrolidone | 10 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Table 1 or Table 2 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Table 1 or Table 2 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Table 1 or Table 2 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Acaricidal Action on Two-Spotted Spider Mite (*Tetranychus urticae*)

Kidney bean leaf disk with a diameter of 2 cm was placed on the wetted filter paper. Ten adult females of two-spotted spider mite were inoculated on each leaf disk, and were sprayed with 50 ml of test solution, prepared by diluting a formulation containing each compound listed in Table 1 or Table 2 as an active ingredient to adjust each of the concentrations to 500 ppm, 50 ppm and 5 ppm. Two days after the treatment, the survived mites were counted. The corrected mortality was calculated by the following equation and the acaricidal activity was judged according to the criterion shown below. The experiment was carried out with two replicates under the condition at 25° C.

$$\text{Corrected mortality (\%)} = \frac{\text{Number of survived mites in untreated group} - \text{Number of survived mites in treated group}}{\text{Number of survived mites in untreated group}} \times 100$$

Criterion:
A - - - Corrected mortality 100%
B - - - Corrected mortality 99%-90%
C - - - Corrected mortality 89%-80%
D - - - Corrected mortality 79%-50%

As comparative compounds, compound Nos. 1-163 and 1-164 disclosed in JP-A-2003-48878 were used.

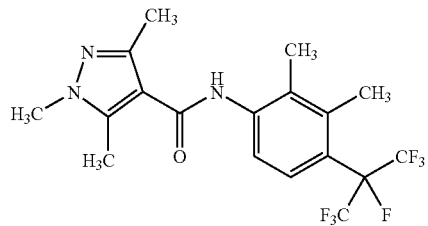

(1-163)

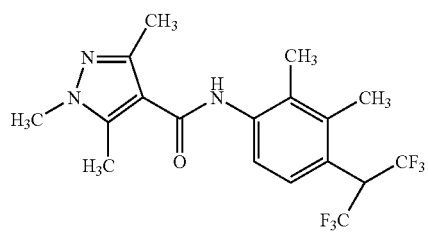

(1-164)

As a result of the above-mentioned test, the compound Nos. 1-3, 1-4, 1-6, 1-8, 1-10, 1-12, 1-13, 1-15, 1-16, 1-25 to 1-28, 1-31, 1-34 to 1-37, 1-45, 1-47 to 1-49, 1-51 to 54, 1-56, 1-57, 1-59, 1-67, 1-69 to 1-72, 1-74 to 1-76, 1-89, 1-101 to 1-114, 1-120 to 1-160, 1-176 to 1-225, 1-228, 1-234, 1-246, 1-258, 1-260, 1-266, 1-270, 1-282, 1-285, 1-294, 1-306 to 1-325, 1-327 to 1-332, 1-335 to 1-337, 1-339 to 1-342, 1-344 to 1-358, 1-361 to 1-373, 1-375 to 1-380, 1-382 to 1-384, 1-386 to 1-389, 1-391 to 1-394, 1-396, 1-399 to 1-406, 1-412 to 416, 1-420 to 1-423, 1-425 to 1-427, 1-429 to 1-433, 1-435 to 1-439, 1-441 to 1-445, 1-448, 1-450 to 1-452, 1-454 to 1-463, 1-467 to 1-470, 1-473, 1-477, 1-478, 1-482 to 1-487, 1-489 to 1-493, 1-496 to 1-502, 1-510, 1-514, 1-515, 1-518, 1-519, 1-523 to 1-527, 1-531, 1-539 to 1-541, 1-546 to 1-549, 2-13, 2-15 to 2-17, 2-21 to 2-23, 2-25, 2-34, 2-36 to 39, 2-41 to 43 and 2-45 of the present invention showed A activity at any concentration of 500 ppm, 50 ppm and 5 ppm, and the compound Nos. 1-23, 1-32, 1-78, 1-173, 1-284, 1-326, 1-334, 1-338, 1-343, 1-385, 1-397 to 1-398, 1-408, 1-410, 1-417, 1-440, 1-447, 1-449, 1-464, 1-472, 1-475, 1-476, 1-479, 1-480, 1-504 to 1-506, 1-509, 1-521, 1-529, 1-530, 1-533, 1-542, 2-26 to 2-33, 2-40 and 2-46 showed A activity at any concentration of 500 ppm and 50 ppm. In contrast, the both control compounds did not show an acaricide activity even at the concentration of 500 ppm.

INDUSTRIAL APPLICABILITY

According to the present invention, agrohorticultural agents, particularly insecticides and acaricides, having superior properties as compared to conventional techniques can be provided.

This application is based on patent application Nos. 234405/2005, 322531/2005 and 114937/2006 filed in Japan, the contents of which are hereby incorporated by reference.

While this invention has been shown and described with references to preferred embodiments thereof, it will be understood by those skilled in the art that various changes in form and details may be made therein without departing from the scope of the invention encompassed by the appended claims.

All patents, patent publications and other publications identified or referenced herein are incorporated by reference in their entirety.

The invention claimed is:

1. A substituted pyrazolecarboxanilide derivative represented by the formula (I):

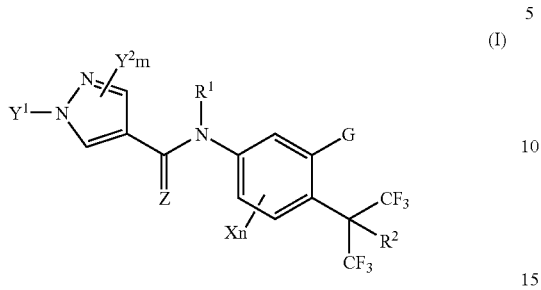

wherein $R^1$ is 1a) a hydrogen atom, 2a) a $C_1$-$C_8$ alkyl group, 3a) a halo $C_1$-$C_6$ alkyl group, 4a) a $C_1$-$C_6$ alkylcarbonyl group, 5a) a halo $C_1$-$C_6$ alkylcarbonyl group, 6a) a $C_2$-$C_6$ alkenylcarbonyl group, 7a) a halo $C_2$-$C_6$ alkenylcarbonyl group, 8a) a $C_1$-$C_6$ alkylcarbonyl $C_1$-$C_6$ alkyl group, 9a) a $C_3$-$C_6$ cycloalkyl group, 10a) a halo $C_3$-$C_6$ cycloalkyl group, 11a) a $C_3$-$C_6$ cycloalkyl $C_1$-$C_6$ alkyl group, 12a) a halo $C_3$-$C_6$ cycloalkyl $C_1$-$C_6$ alkyl group, 13a) a $C_2$-$C_6$ alkenyl group, 14a) a halo $C_2$-$C_6$ alkenyl group, 15a) a $C_2$-$C_6$ alkynyl group, 16a) a halo $C_2$-$C_6$ alkynyl group, 17a) a $C_1$-$C_{10}$ alkoxy $C_1$-$C_6$ alkyl group, 18a) a halo $C_1$-$C_6$ alkoxy $C_1$-$C_6$ alkyl group, 19a) a $C_2$-$C_6$ alkenyloxy $C_1$-$C_6$ alkyl group, 20a) a $C_1$-$C_6$ alkoxy $C_1$-$C_6$ alkoxy $C_1$-$C_6$ alkyl group, 21a) a $C_1$-$C_6$ alkylthio $C_1$-$C_6$ alkyl group, 22a) a halo $C_1$-$C_6$ alkylthio $C_1$-$C_6$ alkyl group, 23a) a $C_1$-$C_6$ alkylsulfinyl $C_1$-$C_6$ alkyl group, 24a) a halo $C_1$-$C_6$ alkylsulfinyl $C_1$-$C_6$ alkyl group, 25a) a $C_1$-$C_6$ alkylsulfonyl $C_1$-$C_6$ alkyl group, 26a) a halo $C_1$-$C_6$ alkylsulfonyl $C_1$-$C_6$ alkyl group, 27a) a mono $C_1$-$C_6$ alkylamino $C_1$-$C_6$ alkyl group, 28a) a di $C_1$-$C_6$ alkylamino $C_1$-$C_6$ alkyl group wherein the alkyl groups are the same or different, 29a) a phenyl $C_1$-$C_6$ alkoxy $C_1$-$C_6$ alkyl group, 30a) a substituted phenyl $C_1$-$C_6$ alkoxy $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 31a) a $C_1$-$C_{16}$ alkoxycarbonyl group, 32a) a $C_1$-$C_6$ alkoxy $C_1$-$C_6$ alkoxycarbonyl group, 33a) a halo $C_1$-$C_6$ alkoxycarbonyl group, 34a) a $C_2$-$C_6$ alkenyloxycarbonyl group, 35a) a $C_1$-$C_6$ alkylthiocarbonyl group, 36a) a mono $C_1$-$C_6$ alkylaminocarbonyl group, 37a) a di $C_1$-$C_6$ alkylaminocarbonyl group wherein the alkyl groups are the same or different, 38a) a $C_1$-$C_6$ alkoxycarbonyl $C_1$-$C_6$ alkyl group, 39a) a $C_1$-$C_6$ alkylsulfonyl group, 40a) a halo $C_1$-$C_6$ alkylsulfonyl group, 41a) a cyano $C_1$-$C_6$ alkyl group, 42a) a phenyl $C_1$-$C_6$ alkyl group, 43a) a substituted phenyl $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 44a) a phenylcarbonyl group, 45a) a substituted phenylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 46a) a heterocyclylcarbonyl group, 47a) a substituted heterocyclylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 48a) a phenoxycarbonyl group, 49a) a substituted phenoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 50a) a phenoxy $C_1$-$C_6$ alkylcarbonyl group, 51a) a substituted phenoxy $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 52a) a phenylsulfonyl group, 53a) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 54a) a di $C_1$-$C_6$ alkylphosphono group wherein the alkyl groups are the same or different, 55a) a di $C_1$-$C_6$ alkylphosphonothio group wherein the alkyl groups are the same or different, 56a) a N—$C_1$-$C_6$ alkyl-N—$C_1$-$C_6$ alkoxycarbonylaminothio group, 57a) a N—$C_1$-$C_6$ alkyl-N—$C_1$-$C_6$ alkoxycarbonyl $C_1$-$C_6$ alkylaminothio group, 58a) a di $C_1$-$C_6$ alkylaminothio group wherein the alkyl groups are the same or different, 59a) a $C_3$-$C_6$ cycloalkylcarbonyl group, 60a) a halo $C_3$-$C_6$ cycloalkylcarbonyl group, 61a) a $C_1$-$C_6$ alkyl $C_3$-$C_6$ cycloalkylcarbonyl group, 62a) a halo $C_1$-$C_6$ alkyl $C_3$-$C_6$ cycloalkylcarbonyl group, 63a) a phenyl $C_1$-$C_6$ alkylcarbonyl group, 64a) a substituted phenyl $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 65a) a phenyl $C_3$-$C_6$ cycloalkylcarbonyl group, 66a) a substituted phenyl $C_3$-$C_6$ cycloalkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 67a) a $C_3$-$C_6$ cycloalkyl $C_1$-$C_6$ alkylcarbonyl group, 68a) a $C_1$-$C_6$ alkoxy $C_1$-$C_6$ alkylcarbonyl group, 69a) a halo $C_3$-$C_6$ cycloalkyl $C_1$-$C_6$ alkylcarbonyl group, 70a) a phenoxy $C_1$-$C_6$ alkoxycarbonyl group, 71a) a substituted phenoxy $C_1$-$C_6$ alkoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 72a) a $C_1$-$C_6$ alkylcarbonyloxy $C_1$-$C_6$ alkyl group, 73a) a $C_1$-$C_6$ alkylcarbonyl $C_1$-$C_6$ alkylcarbonyl group, or 74a) a $C_1$-$C_6$ alkoxycarbonyl $C_1$-$C_6$ alkylcarbonyl group;

$R^2$ is 2b) a halogen atom, 3b) a $C_1$-$C_6$ alkyl group, 4b) a halo $C_1$-$C_6$ alkyl group, 5b) a cyano group, 6b) a hydroxy group, 7b) a $C_1$-$C_6$ alkoxy group, 8b) a halo $C_1$-$C_6$ alkoxy group, 9b) a $C_1$-$C_6$ alkoxy $C_1$-$C_3$ alkoxy group, 10b) a halo $C_1$-$C_6$ alkoxy $C_1$-$C_3$ alkoxy group, 11b) a $C_1$-$C_6$ alkylthio $C_1$-$C_3$ alkoxy group, 12b) a halo $C_1$-$C_6$ alkylthio $C_1$-$C_3$ alkoxy group, 13b) a $C_1$-$C_6$ alkylsulfinyl $C_1$-$C_3$ alkoxy group, 14b) a halo $C_1$-$C_6$ alkylsulfinyl $C_1$-$C_3$ alkoxy group, 15b) a $C_1$-$C_6$ alkylsulfonyl $C_1$-$C_3$ alkoxy group, 16b) a halo $C_1$-$C_6$ alkylsulfonyl $C_1$-$C_3$ alkoxy group, 17b) a mono $C_1$-$C_6$ alkylamino $C_1$-$C_3$ alkoxy group, 18b) a di $C_1$-$C_6$ alkylamino $C_1$-$C_3$ alkoxy group wherein the alkyl groups are the same or different, 19b) a $C_1$-$C_6$ alkylthio group, 20b) a halo $C_1$-$C_6$ alkylthio group, 21b) a $C_1$-$C_6$ alkylsulfinyl group, 22b) a halo $C_1$-$C_6$ alkylsulfinyl group, 23b) a $C_1$-$C_6$ alkylsulfonyl group, 24b) a halo $C_1$-$C_6$ alkylsulfonyl group, 25b) an amino group, 26b) a mono $C_1$-$C_6$ alkylamino group, 27b) a di $C_1$-$C_6$ alkylamino group wherein the alkyl groups are the same or different, 28b) a phenoxy group, 29b) a substituted phenoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 30b) a phenylthio group, 31b) a substituted phenylthio group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 32b) a phenylsulfinyl group, 33b) a substituted phenylsulfinyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 34b) a phenylsulfonyl group, 35b) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 36b) a phenyl $C_1$-$C_6$ alkoxy group, or 37b) a substituted phenyl $C_1$-$C_6$ alkoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group;

G is 1c) a $C_2$-$C_{10}$ alkyl group or 2c) a halo $C_2$-$C_{10}$ alkyl group;

Z is an oxygen atom or a sulfur atom;

X is a hydrogen atom;

$Y^1$ is 1e) a hydrogen atom, 2e) a $C_1$-$C_6$ alkyl group, 3e) a halo $C_1$-$C_6$ alkyl group, 4e) a $C_2$-$C_6$ alkenyl group, 5e) a halo $C_2$-$C_6$ alkenyl group, 6e) a $C_2$-$C_6$ alkynyl group, 7e) a halo $C_2$-$C_6$ alkynyl group, 8e) a $C_1$-$C_6$ alkoxy $C_1$-$C_6$ alkyl group, 9e) a hydroxy $C_1$-$C_6$ alkyl group, 10e) a $C_1$-$C_6$ alkylcarbonyloxy $C_1$-$C_6$ alkyl group, 11e) a $C_3$-$C_6$ cycloalkyl group, 12e) a halo $C_3$-$C_6$ cycloalkyl group, 13e) a $C_3$-$C_6$ cycloalkyl $C_1$-$C_6$ alkyl group, 14e) a halo $C_3$-$C_6$ cycloalkyl $C_1$-$C_6$ alkyl group, 15e) a $C_1$-$C_6$ alkylsulfonyl group, 16e) a halo $C_1$-$C_6$ alkylsulfonyl group, 17e) a $C_1$-$C_6$ alkylthio $C_1$-$C_6$ alkyl group, 18e) a halo $C_1$-$C_6$ alkylthio $C_1$-$C_6$ alkyl group, 19e) a $C_1$-$C_6$ alkylsulfinyl $C_1$-$C_6$ alkyl group, 20e) a halo $C_1$-$C_6$ alkylsulfinyl $C_1$-$C_6$ alkyl group, 21e) a $C_1$-$C_6$ alkylsulfonyl $C_1$-$C_6$ alkyl group, 22e) a halo $C_1$-$C_6$ alkylsulfonyl $C_1$-$C_6$ alkyl group, 23e) a mono $C_1$-$C_6$ alkylamino $C_1$-$C_6$ alkyl group, 24e) a di $C_1$-$C_6$ alkylamino $C_1$-$C_6$ alkyl group wherein the alkyl groups are the same or different, 25e) a phenyl group, 26e) a substituted phenyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group;

$Y^2$ may be the same or different and is 1f) a hydrogen atom, 2f) a halogen atom, 3f) a cyano group, 4f) a nitro group, 5f) a hydroxyl group, 6f) a mercapto group, 7f) an amino group, 8f) a carboxyl group, 9f) a $C_1$-$C_6$ alkyl group, 10f) a halo $C_1$-$C_6$ alkyl group, 11f) a $C_2$-$C_6$ alkenyl group, 12f) a halo $C_2$-$C_6$ alkenyl group, 13f) a $C_2$-$C_6$ alkynyl group, 14f) a halo $C_2$-$C_6$ alkynyl group, 15f) a tri $C_1$-$C_6$ alkylsilyl $C_2$-$C_6$ alkynyl group wherein the alkyl groups are the same or different, 16f) a phenyl $C_2$-$C_6$ alkynyl group, 17f) a $C_1$-$C_6$ alkoxy $C_1$-$C_6$ alkoxy $C_1$-$C_6$ alkyl group, 18f) a hydroxy $C_1$-$C_6$ alkyl group, 19f) a $C_1$-$C_6$ alkylcarbonyloxy $C_1$-$C_6$ alkyl group, 20f) a $C_3$-$C_6$ cycloalkyl group, 21f) a halo $C_3$-$C_6$ cycloalkyl group, 22f) a $C_3$-$C_6$ cycloalkyl $C_1$-$C_6$ alkyl group, 23f) a halo $C_3$-$C_6$ cycloalkyl $C_1$-$C_6$ alkyl group, 24f) a $C_1$-$C_6$ alkoxy group, 25f) a halo $C_1$-$C_6$ alkoxy group, 26f) a $C_1$-$C_6$ alkoxy $C_1$-$C_6$ alkoxy group, 27f) a halo $C_1$-$C_6$ alkoxy $C_1$-$C_6$ alkoxy group, 28f) a phenyl $C_1$-$C_6$ alkoxy group, 29f) a $C_1$-$C_6$ alkoxy $C_1$-$C_6$ alkyl group, 30f) a halo $C_1$-$C_6$ alkoxy $C_1$-$C_6$ alkyl group, 31f) a $C_1$-$C_6$ alkylthio group, 32f) a halo $C_1$-$C_6$ alkylthio group, 33f) a $C_1$-$C_6$ alkylsulfinyl group, 34f) a halo $C_1$-$C_6$ alkylsulfinyl group, 35f) a $C_1$-$C_6$ alkylsulfonyl group, 36f) a halo $C_1$-$C_6$ alkylsulfonyl group, 37f) a $C_1$-$C_6$ alkylthio $C_1$-$C_6$ alkyl group, 38f) a halo $C_1$-$C_6$ alkylthio $C_1$-$C_6$ alkyl group, 39f) a $C_1$-$C_6$ alkylsulfinyl $C_1$-$C_6$ alkyl group, 40f) a halo $C_1$-$C_6$ alkylsulfinyl $C_1$-$C_6$ alkyl group, 41f) a $C_1$-$C_6$ alkylsulfonyl $C_1$-$C_6$ alkyl group, 42f) a halo $C_1$-$C_6$ alkylsulfonyl $C_1$-$C_6$ alkyl group, 43f) a mono $C_1$-$C_6$ alkylamino group, 44f) a di $C_1$-$C_6$ alkylamino group wherein the alkyl groups are the same or different, 45f) a phenylamino group, 46f) a mono $C_1$-$C_6$ alkylamino $C_1$-$C_6$ alkyl group, 47f) a di $C_1$-$C_6$ alkylamino $C_1$-$C_6$ alkyl group wherein the alkyl groups are the same or different, 48f) a phenyl group, 49f) a substituted phenyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 50f) a phenoxy group, 51f) a substituted phenoxy group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 52f) a heterocyclic group, or 53f) a substituted heterocyclic group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group;

m is 1 or 2; and n is 3, or a salt thereof.

2. The substituted pyrazolecarboxanilide derivative of claim 1, wherein $R^1$ is 1a) a hydrogen atom, 2a) a $C_1$-$C_6$ alkyl group, 3a) a halo $C_1$-$C_6$ alkyl group, 4a) a $C_1$-$C_6$ alkylcarbonyl group, 5a) a halo $C_1$-$C_6$ alkylcarbonyl group, 6a) a $C_2$-$C_6$ alkenylcarbonyl group, 13a) a $C_2$-$C_6$ alkenyl group, 17a) a $C_1$-$C_{10}$ alkoxy $C_1$-$C_6$ alkyl group, 18a) a halo $C_1$-$C_6$ alkoxy $C_1$-$C_6$ alkyl group, 19a) a $C_2$-$C_6$ alkenyloxy $C_1$-$C_6$ alkyl group, 20a) a $C_1$-$C_6$ alkoxy $C_1$-$C_6$ alkoxy $C_1$-$C_6$ alkyl group, 29a) a phenyl $C_1$-$C_6$ alkoxy $C_1$-$C_6$ alkyl group, 30a) a substituted phenyl $C_1$-$C_6$ alkoxy $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 31a) a $C_1$-$C_{16}$ alkoxycarbonyl group, 32a) a $C_1$-$C_6$ alkoxy $C_1$-$C_6$ alkoxycarbonyl group, 33a) a halo $C_1$-$C_6$ alkoxycarbonyl group, 34a) a $C_2$-$C_6$ alkenyloxycarbonyl group, 35a) a $C_1$-$C_6$ alkylthiocarbonyl group, 42a) a phenyl $C_1$-$C_6$ alkyl group, 43a) a substituted phenyl $C_1$-$C_6$ alkyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 44a) a phenylcarbonyl group, 45a) a substituted phenylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 46a) a heterocyclylcarbonyl group, 47a) a substituted heterocyclylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 48a) a phenoxycarbonyl group, 49a) a substituted phenoxycarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 50a) a phenoxy $C_1$-$C_6$ alkylcarbonyl group, 51a) a substituted phenoxy $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 52a) a phenylsulfonyl group, 53a) a substituted phenylsulfonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 58a) a di $C_1$-$C_6$ alkylaminothio group wherein the alkyl groups are the same or different, 59a) a $C_3$-$C_6$ cycloalkylcarbonyl group, 61a) a $C_1$-$C_6$ alkyl $C_3$-$C_6$ cycloalkylcarbonyl group, 63a) a phenyl $C_1$-$C_6$ alkylcarbonyl group, 64a) a substituted phenyl $C_1$-$C_6$ alkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 65a) a phenyl $C_3$-$C_6$ cycloalkylcarbonyl group, 66a) a substituted phenyl $C_3$-$C_6$ cycloalkylcarbonyl group having, on the ring, one or more, the same or different substituents selected from a) a halogen atom, b) a cyano group, c) a nitro group, d) a $C_1$-$C_6$ alkyl group, e) a halo $C_1$-$C_6$ alkyl group, f) a $C_1$-$C_6$ alkoxy group, g) a halo $C_1$-$C_6$ alkoxy group, h) a $C_1$-$C_6$ alkylthio group, i) a halo $C_1$-$C_6$ alkylthio group, j) a $C_1$-$C_6$ alkylsulfinyl group, k) a halo $C_1$-$C_6$ alkylsulfinyl group, l) a $C_1$-$C_6$ alkylsulfonyl group, m) a halo $C_1$-$C_6$ alkylsulfonyl group, n) a mono $C_1$-$C_6$ alkylamino group, o) a di $C_1$-$C_6$ alkylamino group wherein the alkyl groups are the same or different, and p) a $C_1$-$C_6$ alkoxycarbonyl group, 68a) a $C_1$-$C_6$ alkoxy $C_1$-$C_6$ alkylcarbonyl group, 73a) a $C_1$-$C_6$ alkylcarbonyl $C_1$-$C_6$ alkylcarbonyl group, or 74a) a $C_1$-$C_6$ alkoxycarbonyl $C_1$-$C_6$ alkylcarbonyl group, or a salt thereof.

3. The substituted pyrazolecarboxanilide derivative of claim 1, wherein $R^2$ is 2b) a halogen atom, 6b) a hydroxy group, 7b) a $C_1$-$C_6$ alkoxy group, or 8b) a halo $C_1$-$C_6$ alkoxy group, or a salt thereof.

4. The substituted pyrazolecarboxanilide derivative of claim 1, wherein G is 1c) a $C_2$-$C_{10}$ alkyl group, or a salt thereof.

5. The substituted pyrazolecarboxanilide derivative of claim 1, wherein

Z is an oxygen atom;

$Y^1$ is 2e) a $C_1$-$C_6$ alkyl group, 3e) a halo $C_1$-$C_6$ alkyl group, or 4e) a $C_2$-$C_6$ alkenyl group; and $Y^2$ is 1f) a hydrogen atom, 2f) a halogen atom, 9f) a $C_1$-$C_6$ alkyl group, 10f) a halo $C_1$-$C_6$ alkyl group, or 31f) a $C_1$-$C_6$ alkylthio group, or a salt thereof.

6. The substituted pyrazolecarboxanilide derivative of claim 1, wherein $R^1$ is 1a) a hydrogen atom, 4a) a $C_1$-$C_6$ alkylcarbonyl group, 5a) a halo $C_1$-$C_6$ alkylcarbonyl group, 17a) a $C_1$-$C_{10}$ alkoxy $C_1$-$C_6$ alkyl group, 18a) a halo $C_1$-$C_6$ alkoxy $C_1$-$C_6$ alkyl group, 31a) a $C_1$-$C_{16}$ alkoxycarbonyl group, 33a) a halo $C_1$-$C_6$ alkoxycarbonyl group, or 68a) a $C_1$-$C_6$ alkoxy $C_1$-$C_6$ alkylcarbonyl group;

$R^2$ is 1b) a hydrogen atom, or 7b) a $C_1$-$C_6$ alkoxy group;

G is 1c) a $C_2$-$C_{10}$ alkyl group;

Z is an oxygen atom;

$Y^1$ is 2e) a $C_1$-$C_6$ alkyl group; and $Y^2$ may be the same or different and is 1f) a hydrogen atom, 2f) a halogen atom, 9f) a $C_1$-$C_6$ alkyl group, or 10f) a halo $C_1$-$C_6$ alkyl group, or a salt thereof.

7. An agrohorticultural agent comprising the substituted pyrazolecarboxanilide derivative of claim 1 or a salt thereof as an active ingredient, and a suitable inert carrier.

8. The agrohorticultural agent of claim 7, which is an agrohorticultural insecticide or acaricide.

9. A method of using an agrohorticultural agent, which comprises treating a target plant or soil with an effective amount of the agrohorticultural agent of claim 7 so as to control insect pests or acarina pests from useful plants.

10. A method of using an agrohorticultural agent, which comprises treating a target plant or soil with an effective amount of the agrohorticultural agent of claim 8 so as to control insect pests or acarina pests from useful plants.

* * * * *

UNITED STATES PATENT AND TRADEMARK OFFICE
CERTIFICATE OF CORRECTION

PATENT NO. : 8,404,861 B2
APPLICATION NO. : 11/990282
DATED : March 26, 2013
INVENTOR(S) : Takashi Furuya It is certified that error appears in the above-identified patent and that said Letters Patent is hereby corrected as shown below:

In the Claims

Claim 6, in column 66, line 58:

"$R^2$ is 1b) a hydrogen atom, or 7b) a $C_1$-$C_6$ alkoxy group;", should read

-- $R^2$ is 7b) a $C_1$-$C_6$ alkoxy group; --.

Signed and Sealed this
Thirtieth Day of July, 2013

Teresa Stanek Rea
*Acting Director of the United States Patent and Trademark Office*